US011576963B2

(12) United States Patent
Martinez-Sobrido et al.

(10) Patent No.: US 11,576,963 B2
(45) Date of Patent: Feb. 14, 2023

(54) MULTIVALENT LIVE-ATTENUATED INFLUENZA VACCINE FOR PREVENTION AND CONTROL OF EQUINE INFLUENZA VIRUS (EIV) IN HORSES

(71) Applicants: UNIVERSITY OF ROCHESTER, Rochester, NY (US); UNIVERSITY OF KENTUCKY RESEARCH FOUNDATION, Lexington, KY (US)

(72) Inventors: Luis Martinez-Sobrido, San Antonio, TX (US); Thomas Chambers, Lexington, KY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 16/975,846

(22) PCT Filed: Feb. 27, 2019

(86) PCT No.: PCT/US2019/019742
§ 371 (c)(1),
(2) Date: Aug. 26, 2020

(87) PCT Pub. No.: WO2019/168911
PCT Pub. Date: Sep. 6, 2019

(65) Prior Publication Data
US 2020/0405843 A1 Dec. 31, 2020

Related U.S. Application Data

(60) Provisional application No. 62/635,628, filed on Feb. 27, 2018.

(51) Int. Cl.
*A61K 39/145* (2006.01)
*A61P 31/16* (2006.01)
*A61K 39/295* (2006.01)

(52) U.S. Cl.
CPC .......... *A61K 39/145* (2013.01); *A61K 39/295* (2013.01); *A61P 31/16* (2018.01)

(58) Field of Classification Search
None
See application file for complete search history.

(56) References Cited

U.S. PATENT DOCUMENTS

| | | | | |
|---|---|---|---|---|
| 7,722,884 | B2 | 5/2010 | Shields | |
| 7,959,929 | B2 | 6/2011 | Crawford | |
| 8,246,962 | B2 | 8/2012 | Cho | |
| 10,478,489 | B2 | 11/2019 | Martinez-Sobrido | |
| 2009/0324640 | A1 * | 12/2009 | Kawaoka | A61K 39/12 435/235.1 |
| 2011/0150912 | A1 | 6/2011 | Perez | |
| 2018/0243401 | A1 | 8/2018 | Martinez-Sobrido | |
| 2018/0256703 | A1 | 9/2018 | Martinez-Sobrido | |
| 2019/0125860 | A1 | 5/2019 | Martinez-Sobrido | |
| 2020/0023055 | A1 | 1/2020 | Martinez-Sobrido | |

FOREIGN PATENT DOCUMENTS

| | | | |
|---|---|---|---|
| WO | 2007024947 | A2 | 3/2007 |
| WO | 2011044561 | A1 | 4/2011 |
| WO | 2013030176 | A2 | 3/2013 |
| WO | 2015010073 | A1 | 1/2015 |
| WO | 2017210528 | | 12/2017 |
| WO | WO/17/210528 | * | 12/2017 |

OTHER PUBLICATIONS

Rodriguez et al., Development of a novel equine influenza virus live-attenuated vaccine, 2018, Virology, vol. 516, pp. 76-85.*
Bryant et al., Isolation and characterisation of equine influenza viruses (H3N8) from Europe and North America from 2008 to 2009, Veterinary Microbiology, 2011, vol. 147, pp. 19-27.*
Broadbent et al., The Temperature-Sensitive and Attenuation Phenotypes Conferred by Mutations in the Influenza Virus PB2, PB1, and NP Genes Are Influenced by the Species of Origin of the PB2 Gene in Reassortant Viruses Derived from Influenza A/California/ Jul. 2009 and A/WSN/33, 2014, Journal of Virology, vol. 21.*
Rodriguez, Laura, et al. "A live-attenuated influenza vaccine for H3N2 canine influenza virus." Virology 504 (2017): 96-106.
Bucko et al., "Equine influenza: OIE—World Organisation for Animal Health", Mar. 28, 2018 (Mar. 28, 2018).
Rash, Adam, et al. "Evolution and divergence of H3N8 equine influenza viruses circulating in the United Kingdom from 2013 to 2015." Pathogens 6.1 (2017): 6.
Daly, Janet M., et al. "Equine influenza: a review of an unpredictable virus." The Veterinary Journal 189.1 (2011): 7-14.
Timoney, Peter J. "Factors influencing the international spread of equine diseases." Veterinary Clinics of North America: Equine Practice 16.3 (2000): 537-551.
Cullinane A, Elton D, Mumford J. Equine influenza—surveillance and control. Influenza Other Respir Viruses. Nov. 2010;4(6):339-44.
Paillot R. A Systematic Review of Recent Advances in Equine Influenza Vaccination. Vaccines (Basel). Nov. 14, 2014:2(4):797-831.
Paillot R, El-Hage CM. The Use of a Recombinant Canarypox-Based Equine Influenza Vaccine during the 2007 Australian Outbreak: A Systematic Review and Summary. Pathogens. Jun. 10, 2016;5(2):42.
Daly JM, Yates RJ, Browse G, Swann Z, Newton JR, Jessett D, Davis-Poynter N, Mumford JA. Comparison of hamster and pony challenge models for evaluation of effect of antigenic drift on cross protection afforded by equine influenza vaccines. Equine Vet J. Jul. 2003;35(5):458-62.
Garner MG, Cowled B, East IJ, Moloney BJ, Kung NY. Evaluating the effectiveness of early vaccination in the control and eradication of equine influenza—a modelling approach. Prev Vet Med. Apr. 1, 2011;99(1):15-27.
Chambers et al., 2009, "Influenza A viruses with truncated NS1 as modified live virus vaccines: pilot studies of safety and efficacy in horses," Equine Vet. J. 41, 87-92.
Rodriguez et al., 2017, "Influenza A Virus Studies in a Mouse Model of Infection," J. Vis. Exp, 127, e55898.

(Continued)

*Primary Examiner* — Benjamin P Blumel
(74) *Attorney, Agent, or Firm* — Riverside Law LLP

(57) ABSTRACT

The present invention provides compositions and methods related to equine live-attenuated influenza vaccines.

20 Claims, 7 Drawing Sheets

Specification includes a Sequence Listing.

(56) References Cited

OTHER PUBLICATIONS

Wilson and Robinson, 2000, "Field Safety of a Modified-Live, Cold-Adapted Intranasal Equine Influenza Vaccine (Heska TM Flu Avert TM I.N. Vaccine) in Horses," J. Equine Vet. Sci. 20, 8-10.
Lu et al., 2009, "Development and Evaluation of One-Step TaqMan Real-Time Reverse Transcription-PCR Assays Targeting Nucleoprotein, Matrix, and Hemagglutinin Genes of Equine Influenza Virus," J. Clin. Microbiol. 47, 3907-3913.
Mumford et al., 1990, "Experimental infection of ponies with equine influenza (H3N8) viruses by intranasal inoculation or exposure to aerosols," Equine Vet. J. 22, 93-98.
Townsend et al., 2001, "Efficacy of a cold-adapted, intranasal, equine influenza vaccine: challenge trials," Equine Vet. J. 33, 637-643).
Lunn et al., 2001, "Safety, efficacy, and immunogenicity of a modified-live equine influenza virus vaccine in ponies after induction of exercise-induced immunosuppression," J. Am. Vet. Med. Assoc. 218, 900-906.
Chambers et al., 2001, "A new modified live equine influenza virus vaccine: phenotypic stability, restricted spread and efficacy against heterologous virus challenge," Equine Vet. J. 33, 630-636.
Nogales et al., 2017, "Canine influenza viruses with modified NS1 proteins for the development of live-attenuated vaccines," Virology, 500, 1-10.
Nogales et al., 2016, "Rearrangement of influenza virus spliced segments for the development of live-attenuated vaccines," J. Viol, 91: 6291-6302.
Rodriguez et al., 2017, "A live-attenuated influenza vaccine for H3N2 canine influenza virus," Virology, 504, 96-106.
Chambers and Reedy, 2014, "Equine influenza serological methods," Methods Mol.Biol. 1161, 411-422.
Youngner et al., 2001, "Derivation and characterization of a live attenuated equine influenza vaccine virus," Am. J. Vet. Res. 62, 1290-1294.
Suguitan et al., 2006, "Live, attenuated influenza A H5N1 candidate vaccines provide broad cross-protection in mice and ferrets," PLoS Med. 3, e360.
Abdel-Moneim et al. 2011, "Molecular evolution of the six internal genes of H5N1 equine influenza A virus," Archives of Virology. 2011; 156: 1257-1262.
Murphy et al. 1997, "An influenza A live attenuated reassortant virus possessing three temperature-sensitive mutations in the PB2 polymerase gene rapidly loses temperature sensitivity following replication in hamsters," Vaccine, 15 (12/13): 1372-1378.
Office Action dated May 1, 2020 for U.S. Appl. No. 16/306,008 (pp. 1-14).
Shinya et al. 2007, "Adaptation of an H7N7 equine influenza A virus in mice," Journal of General Virology, 88: 847-553.
Zhou et al. 2012, "Engineering Temperature Sensitive Live Attenuated Influenza Vaccines from Emerging Viruses," Vaccine, 30 (24): 3691-3702.
Pecoraro et al., 2013, "Evaluation of virus isolation, one-step real-time reverse transcription polymerase chain reaction assay, and two rapid influenza diagnostic tests for detecting canine Influenza A virus H3N8 shedding in dogs." Journal of Veterinary Diagnostic Investigation, 25: 402-406.
Song et al., 2015, "Canine susceptibility to human influenza viruses (A/pdm 09H1N1, A/H3N2 and B)." The Journal of General Virology, 96: 254-258.
Martinez-Sobrido et al., Journal of Visualized Experiments, (2010), p. 42.
Holt et al., 2010, "Serologic prevalence of antibodies against canine influenza virus (H3N8) in dogs in a metropolitan animal shelter." Journal of the American Veterinary Medical Association, 237: 71-73.
Gonzalez et al., 2014, "Infection and pathogenesis of canine, equine, and human influenza viruses in canine tracheas." J Viral, 88: 9208-9219.

Yoon et al., 2005, "Influenza virus infection in racing greyhounds." Emerging Infectious Diseases, 11: 1974-1976.
Song et al., 2008, "Transmission of avian influenza virus (H3N2) to dogs." Emerging Infectious Diseases, 14: 741-746.
JAVMA News. 2015. Outbreak of canine influenza caused by new strain of virus. J Am Vet Med Assoc. 246:1049, 2 pages.
Jeoung et al., 2013, "A novel canine influenza H3N2 virus isolated from cats in an animal shelter." Veterinary Microbiology, 165: 281-286.
Song et al., 2011, "Interspecies transmission of the canine influenza H3N2 virus to domestic cats in South Korea, 2010." The Journal of General Virology, 92: 2350-2355.
Varghese et al., 1992, "The structure of the complex between influenza virus neuraminidase and sialic acid, the viral receptor." Proteins, 14: -327-332.
Crawford et al., 2005, "Transmission of equine influenza virus to dogs." Science, 310: 482-485.
Baker et al., 2015, "Downregulating viral gene expression: codon usage bias manipulation for the generation of novel Influenza A virus vaccines." Future Virology, 10: 715-730.
Anonymous, "4 Things Pet Owners Should Know About the Dog Flu—C2CND", (Aug. 3, 2015), pp. 1-5, URL: http://c2cnd.org/connect/4-things-pet-owners-know-dog-flu/, (Oct. 27, 2016), XP055314404.
Xiangxiang Sun et al, "Evidence of avian-like H9N2 influenza A virus among dogs in Guangxi, China", Infection, Genetics and Evolution, NL, (Dec. 1, 2013), vol. 20, doi:10.1016/j.meegid.2013. 10.012, ISSN 1567-1348, pp. 471-475, XP055314508.
Bin Zhou et al, "Engineering temperature sensitive live attenuated influenza vaccines from emerging viruses", Vaccine, Elsevier Ltd, GB, vol. 30, No. 24, doi:10.1016/J.VACCINE.2012.03.025, ISSN 0264-410X, (Mar. 12, 2012), pp. 3691-3702, (Mar. 17, 2012), XP028487806.
Notification of Transmittal of The International Search Report and The Written Opinion of the International Searching Authority, or the Declaration, dated Dec. 22, 2016, received in corresponding International Application No. PCT/ US2016/047715. 20 pages.
Communication pursuant to Article 94(3) EPC received in corresponding European Patent Application No. 16757480.5, dated Sep. 10, 2019. 11 pages.
Parrish et al., 2015, "Influenza Virus Reservoirs and intermediate Hosts: Dogs, Horses, and New Possibilities for Influenza Virus Expoure of Humans" J. Virol, 89:2990-2994.
Parrish et al., 2005, "The Origins of New Pandemic Viruses: The Acquisition of New Host Ranges by Canine Parvovirus and Influenza A Viruses" Annual review of microbiology, 59:553-586.
Belshe et al., 2000, "Correlates of Immune Protection Induced by Live, Attenuated, Cold-Adapted, Trivalent, Intranasal Influenza Virus Vaccine" The Journal of infectious diseases, 181:1133-1137.
Centers for Disease Control and Prevention, 2010, "Licensure of a High-Dose Inactivated Influenza Vaccine for Persons Aged 65 Years (Fluzone High-Dose) and Guidance for Use—United States, 2010" MMWR, 59(16):485-486.
Rimmelzwaan et al., 2007, "Influenza virus-specific cytotoxic T lymphocytes: a correlate of protection and a basis for vaccine development" Current opinion in biotechnology, 18:529-536.
Smith et al., 2009, "Origins and evolutionary genomics of the 2009 swine-origin H1N1 influenza A epidemic" Nature, 459:1122-1125.
Dundon et al., 2010, "Serologic Evidence of Pandemic (H1N1) 2009 Infection in Dogs, Italy" Emerging infectious diseases, 16:2019-2021.
Hale et al., 2008, "The multifunctional NS1 protein of influenza A viruses" The Journal of general virology, 89:2359-2376.
Lamb et al., 1980, "Mapping of the two overlapping genes for polypeptides NS1 and NS2 on RNA segment 8 of Influenza virus genome" Proceedings of the National Academy of Sciences, 77:1857-1861.
Garcia-Sastre et al., 1998, "Influenza A Virus Lacking the NS1 Gene Replicates in Interferon-Deficient Systems" Virology, 252:324-330.
Steidle et al., 2010, "Glycine 184 in Nonstructural Protein NS1 Determines the Virulence of Influenza A Virus Strain PR8 without Affecting the Host Interferon Response" J Viral, 84:12761-12770.
Geiss et al., 2002, "Cellular transcriptional profiling in influenza A virus-infected lung epithelial cells: The role of the nonstructural

(56) References Cited

OTHER PUBLICATIONS

NS1 protein in the evasion of the host innate defense and its potential contribution to pandemic influenza" Proceedings of the National Academy of Sciences, 99:10736-10741.
Falcon et al., 2005, "Attenuation and immunogenicity in mice of temperature-sensitive influenza viruses expressing truncated NS1 proteins" The Journal of general virology, 86:2817-2821.
Ferko et al., 2004, "Immunogenicity and Protection Efficacy of Replication-Deficient Influenza A Viruses with Altered NS1 Genes" J Virol, 78:13037-13045.
Quinlivan et al., 2005, "Attenuation of Equine Influenza Viruses through Truncations of the NS1 Protein" J Viral, 79:8431-8439.
Richt et al., 2009, "Attenuated Influenza Virus Vaccines with Modified NS1 Proteins" Current topics in microbiology and immunology, 333:177-195.
Steel et al., 2009, "Live Attenuated Influenza Viruses Containing NS1 Truncations as Vaccine Candidates against H5N1 Highly Pathogenic Avian Influenza" J Virol 83:1742-1753.
Vincent et al., 2007, "Efficacy of intranasal administration of a truncated NS1 modified live influenza virus vaccine in swine" Vaccine 25:7999-8009.
Richt et al., 2006, "Vaccination of Pigs against Swine Influenza Viruses by Using an NS1-Truncated Modified Live-Virus Vaccine" J Viral 80:11009-11018.
Solorzano et al., 2005, "Mutations in the NS1 Protein of Swine Influenza Virus Impair Anti-Interferon Activity and Confer Attenuation in Pigs" J Virol, 79:7535-7543.
Choi et al., 2015, "Development of a dual-protective live attenuated vaccine against H5N1 and H9N2 avian influenza viruses by modifying the NS1 gene" Archives of virology, 160:1729-1740.
Wang et al., 2008, "Characterization of influenza virus variants with different sizes of the non-structural (NS) genes and their potential as a live influenza vaccine in poultry" Vaccine, 26:3580-3586.
Baskin et al., 2007, "Functional Genomic and Serological Analysis of the Protective Immune Response Resulting from Vaccination of Macaques with an NS1-Truncated Influenza Virus" J Viral, 81:11817-11827.
Pica et al., 2012, "NS1-Truncated Live Attenuated Virus Vaccine Provides Robust Protection to Aged Mice from Viral Challenge" J Virol, 86:10293-10301.
Hai et al., 2008, "Influenza B Virus NS1-Truncated Mutants: Live-Attenuated Vaccine Approach" J Virol, 82:10580-10590.
Talon et al., 2000, "Influenza A and B viruses expressing altered NS1 proteins: A vaccine approach" Proceedings of the National Academy of Sciences, 97:4309-4314.
Deshpande et al., 2009, "Evaluation of the Efficacy of a Canine Influenza Virus (H3N8) Vaccine in Dogs Following Experimental Challenge" Veterinary therapeutics: research in applied veterinary medicine, 10:103-112.
Martinez-Sobrido et al., 2009, "Identification of Amino Acid Residues Critical for the Anti-Interferon Activity of the Nucleoprotein of the Prototypic Arenavirus Lymphocytic Choriomeningitis Virus" J Virol, 83:11330-11340.
Martinez-Sobrido et al., 2006, "Inhibition of the type I interferon response by the nucleoprotein of the prototypic arenavirus lymphocytic choriomeningitis virus" J Virol, 80:9192-9199.
Park et al., 2003, "Newcastle Disease Virus (NDV)-Based Assay Demonstrates Interferon-Antagonist Activity for the NDV V Protein and the Nipah Virus V, W, and C Proteins" J Virol, 77:1501-1511.
Newbury et al., 2016, "Prolonged intermittent virus shedding during an outbreak of canine influenza A H3N2 virus infection in dogs in three Chicago area shelters: 16 cases (Mar. to May 2015)" Journal of the American Veterinary Medical Association, 248:1022-1026.
Ramirez-Martinez et al., 2013, "Evidence of transmission and risk factors for influenza A virus in household dogs and their owners" Influenza and other respiratory viruses, 7:1292-1296.
Randall et al., 2008, "Interferons and viruses: an interplay between induction, signalling, antiviral responses and virus countermeasures" The Journal of general virology, 89:1-47.

Solorzano et al., 2010, "Alternative Live-Attenuated Influenza Vaccines Based on Modifications in the Polymerase Genes Protect against Epidemic and Pandemic Flu." Journal of Virology, 84(9): 4587-4596.
Song et al., 2007, "A New Generation of Modified Live-Attenuated Avian Influenza Viruses Using a Two-Strategy Combination as Potential Vaccine Candidates." Journal of Virology, 81(17): 9238-9248.
Subbarao et al., 1995, "Sequential addition of temperature-sensitive missense mutations into the PB2 gene of Influenza A transfectant viruses can effect an increase in temperature sensitivity and attenuation and permits the rational design of a genetically engineered live influenza a virus vaccine." Journal of Virology, 69(10): 5969-5977.
Hickman et al., 2008, An avian live attenuated master backbone for potential use in epidemic and pandemic influenza vaccines. Journal of General Virology, 89(11): 2682-2690.
Mariana Baz et al., 2014, "A live attenuated H3N8 influenza vaccine is highly immunogenic and efficacious in mice and ferrets." Journal of Virology, 89(3): 1652-1659.
Kappes et al., 2011, "Vaccination with NS-1 truncated H3N2 swine influenza virus rimes T cells and confers cross-protection against an H1N1 heterosubtypic challenge in pigs." Vaccine, 30(2): 280-288.
Voorhees et al., "Spread of Canine Influenza A9H3N2) Virus, United States," Emerging Infectious Diseases, 23 (12):1950-1957, 2017.
Chao, "A Single Amino Acid Deletion at the Amino Terminus of Influenza Virus Hemagglutinin Causes Malfolding and Blocks Exocytosis of the Molecule in Mammalian Cells," The Journal of Biological Chemistry, 267(4):2142-2148, 1992.
Murphy et al., "An influenza A live attenuated reassortant virus possessing three temperature-sensitive mutations in the PB2 polymerase gene rapidly loses temperature sensitivity following replication in hamsters," Vaccine, 15 (12/13):1372-1378, 1997.
Hanson et al., "Canine Influenza," Clinicians Brief, University of Georgia, 97-103, 2016.
Suzuki et al., "Amino Acid Substitutions of PB1 of Avian Influenza Viruses Influence Pathogenicity and Transmissibility in Chickens," Journal of Virology, 88(19):11130-11139, 2014.
Yen et al., 2009, "Pandemic influenza as a current threat." Current topics in microbiology and immunology, 333: 3-24.
Pica et al., 2013, "Toward a universal influenza virus vaccine: prospects and challenges." Annual Review of Medicine, 64: 189-202.
Wong et al., 2013, "Traditional and new influenza vaccines." Clinical Microbiology Reviews, 26: 476-492.
Belshe et al., 2007, "Live attenuated versus inactivated influenza vaccine in infants and young children." The New England Journal of Medicine, 356: 685-696.
Cox et al., 2008, "FluBlok, a recombinant hemagglutinin influenza vaccine." Influenza and other Respiratory Viruses: 2:211-219.
Osterholm et al., 2012, "Efficacy and effectiveness of influenza vaccines: a systematic review and meta-analysis" The Lancet Infectious Diseases, 12: 36-44.
Pronker et al., 2012, "Development of new generation influenza vaccines: recipes for success?" Vaccine, 30: 7344-7347.
Belongia et al., 2009, "Effectiveness of inactivated influenza vaccines varied substantially with antigenic match from the 2004-2005 season to the 2006-2007 season." Journal of Infectious Diseases, 199: 159-167.
Gorse et al., 1991, "Superiority of live attenuated compared with inactivated influenza A virus vaccines in older, Chronically ill adults." Chest, 100: 977-984.
Maassab., 1968, "Plaque formation of influenza virus at 25 degrees C." Nature, 219:645-646.
Cox et al., 1988, "Identification of sequence changes in the cold-adapted, live attenuated influenza vaccine strain, A/Ann Arbor/6/60 (H2N2)." Virology, 167:554-567.
Snyder et al., 1988, "Four viral genes independently contribute to attenuation of live influenza A/Ann Arbor/6/60 (H2N2) cold-adapted reassortant virus vaccines." J Viral, 62:488-495.
Chan et al., 2008, "The cold adapted and temperature sensitive influenza A/Ann Arbor/6/60 virus, the master donor virus for live

(56) References Cited

OTHER PUBLICATIONS attenuated influenza vaccines, has multiple defects in replication at the restrictive temperature." Virology, 380:304-311.
Cox et al., 2015, "Development of a mouse-adapted live attenuated influenza virus that permits in vivo analysis of enhancements to the safety of live attenuated influenza virus vaccine." J Viral, 89(6):3421-3426.
Jin et al., 2004, "Imparting temperature sensitivity and attenuation in ferrets to A/Puerto Rico/8/34 influenza virus by transferring the genetic signature for temperature sensitivity from cold-adapted A/Ann Arbor/6/60." J Virol, 78:995-998.
Nogales et al., 2014, "Influenza A virus attenuation by codon deoptimization of the NS gene for vaccine development." J Virol, 88: 10525-10540.
Feng et al., 2015, "Equine and Canine Influenza H3N8 Viruses Show Minimal Biological Differences Despite Phylogenetic Divergence." J Viral, 89: 6860-6873.
Nogales et al., 2015, "Replication-competent influenza A viruses expressing a red fluorescent protein." Virology, 476: 206-216.
Jin et al., 2003, "Multiple amino acid residues confer temperature sensitivity to human influenza virus vaccine strains (FluMist) derived from cold-adapted A/Ann Arbor/6/60." Virology, 306: 18-24.
Nogales et al., 2016, "Rearrangement of Influenza Virus Spliced Segments for the Development of Live-Attenuated Vaccines." J Virol, 90: 6291-6302.
Maassab, 1999, Reviews in medical virology, 9: 237-244.
Murphy et al., 2002, "Principles underlying the development and use of live attenuated cold-adapted influenza A and B virus vaccines." Viral immunology, 15: 295-323.
Kohlmeier et al., 2009, "Immunity to respiratory viruses." Annual review of immunology, 27: 61-82.
Cheng et al., 2013, The Journal of infectious diseases, 208: 594-602.
De Villiers et al., 2009, "Efficacy and safety of a live attenuated influenza vaccine in adults 60 years of age and older." Vaccine, 28: 228-234.
Katsura et al., 2012, "A replication-incompetent virus possessing an uncleavable hemagglutinin as an influenza vaccine." Vaccine, 30: 6027-6033.
Victor et al., 2012, "A replication-incompetent PB2-knockout influenza A virus vaccine vector." J Viral, 86(8): 4123-4128.
Baker et al., 2013, "Protection against lethal influenza with a viral mimic." J Virol, 87: 8591-8605.
Guo et al., 2014, "Induction of CD8 T cell heterologous protection by a single dose of single-cycle infectious influenza virus." J Viral, 88: 12006-12016.
Powell et al., 2012, "Pseudotyped influenza A virus as a vaccine forthe induction of heterotypic immunity." J Virol, 86: 13397-13406.
Uraki et al., 2013, "A novel bivalent vaccine based on a PB2-knockout influenza virus protects mice from pandemic H1N1 and highly pathogenic H5N1 virus challenges." J Viral, 87: 7874-7881.
Hayward et al., 2010, "Microevolution of canine influenza virus in shelters and its molecular epidemiology in the United States." J Virol, 84:12636-12645.
Rivailler et al., 2010, "Evolution of canine and equine influenza (H3N8) viruses co-circulating between 2005 and 2008." Virology, 408: 71-79.
Bean et al., 1992, "Evolution of the H3 influenza virus hemagglutinin from human and nonhuman hosts." J Virol, 66:1129-1138.
Both et al., 1983, "Antigenic drift in influenza virus H3 hemagglutinin from 1968 to 1980: multiple evolutionary pathways and sequential amino acid changes at key antigenic sites." J Virol, 48:52, 9 pages.

Bush et al., 1999, "Positive selection on the H3 hemagglutinin gene of human influenza virus A." Molecular biology and evolution, 16: 1457-1465.
De Jong et al., 2007, "Antigenic and genetic evolution of swine influenza A (H3N2) viruses in Europe." J Virol, 81: 4315-4322.
Epperson et al., 2013, Human infections with influenza A(H3N2) variant virus in the United States, 2011-2012. Clinical infectious diseases, 57 Suppl 1:S4-S11.
Hussain et al., 2010, "Comparison of egg and high yielding MDCK cell-derived live attenuated influenza virus for commmercial production of trivalent influenza vaccine: in vitro cell susceptibility and influenza virus replication kinetics in 3emissive and semi-permissive cells." Vaccine, 28: 3848-3855.
Sequence alignment of SEQ ID 3 of U.S. Appl. No. 16/589,247 with SEQ ID 3 of U.S. Pat. No. 10/478,489 Nov. 2019, 2 pages.
Sequence alignment of SEQ ID 4 of U.S. Appl. No. 16/589,247 with SEQ ID 4 of U.S. Pat. No. 10/478,489 Nov. 2019, 2 pages.
Alignment of SEQ ID 1 of U.S. Appl. No. 16/589,247 with SEQ ID 1 of U.S. Pat. No. 10/478,489 Nov. 2019, 5 pages.
Alignment of SEQ ID 2 of U.S. Appl. No. 16/589,247 with SEQ ID 2 of U.S. Pat. No. 10/478,489 Nov. 2019, 5 pages.
Sequence alignment of SEQ ID 1 of U.S. Appl. No. 16/589,247 with Geneseq db acc No. AFB78958 by Minke et al. in USPgPub2007048819 Mar. 2007, 6 pages.
Alignment of SEQ ID 1 of U.S. Appl. No. 16/589,247 with Geneseq db acc No. AFU64076 by Yoon et al in W02007048086 Apr. 2007, 6 pages.
Sequence alignment of SEQ ID 2 of U.S. Appl. No. 16/589,247 with Geneseq db acc No. AFU64076 by Yoon et al in W02007048086 Apr. 2007, 6 pages.
Sequence alignment of SEQ ID 3 of U.S. Appl. No. 16/589,247 with Geneseq db acc No. AFU64076 by Yoon et al in W02007048086 Apr. 2007, 3 pages.
Alignment of SEQ ID 4 of U.S. Appl. No. 16/589,247 with Geneseq db acc No. AFU64075 by Yoon et al in W02007048086 Apr. 2007, 3 pages.
International Search Report and Written Opinion, dated Sep. 27, 2017; recieved in PCT Application No. PCT/US2017/035630, 16 pages.
Su et al. 2014, "Evidence forsubclinical influenza A(H1N1)pdm09 virus infection among dogs in Guangdong Province, China," Journal of Clinical Microbiology, 52 (5): 1762-1765).
Zhang et al. 2013, "Domestic cats and dogs are susceptible to H9N2 avian influenza virus," Virus Research, 175: 52-57.
Li et al. 2010, "Avian-origin H3N2 canine influenza A viruses in Southern China," Infection, Genetics and Evolution, 10: 1286-1288.
Notice of Allowance dated Sep. 2, 2020 for U.S. Appl. No. 16/306,008 (pp. 1-5).
Anonymous: "EM_STD:MF173262", Jan. 3, 2018 (Jan. 3, 2018), XP055846097, Retrieved from the Internet: URL:http://ibis.internal.epo.org/exam/dbfetch.jsp?id=EM_STD:MF173262.
Anonymous: "UPI000E32E72B", Aug. 29, 2018 (Aug. 29, 2018), XP055846189, Retrieved from the Internet: URL:https://www.uniprot.org/uniparc/UPI000E32E72B.
Anonymous: "UPI000E331829", , Aug. 29, 2018 (Aug. 29, 2018), XP055846195, Retrieved from the Internet: URL:https://www.uniprot.org/uniparc/UPI000E331829.
Anonymous: "UPI0003800780", , Nov. 13, 2013 (Nov. 13, 2013), XP055846362, Retrieved from the Internet: URL:https://www.uniprot.org/uniparc/UPI0003800780.
Anonymous: "UPI00030935F1", , Mar. 19, 2014 (Mar. 19, 2014), XP055846369, Retrieved from the Internet: URL:https://www.uniprot.org/uniparc/UPI00030935F1.

* cited by examiner

MULTIVALENT LIVE-ATTENUATED INFLUENZA VACCINE FOR PREVENTION AND CONTROL OF EQUINE INFLUENZA VIRUS (EIV) IN HORSES

CROSS-REFERENCE TO RELATED APPLICATIONS

This application is a U.S. national phase application filed under 35 U.S.C. § 371 claiming benefit to International Patent Application No. PCT/US2019/019742, filed Feb. 27, 2019, which is entitled to priority under 35 U.S.C. § 119(e) to U.S. Provisional Patent Application No. 62/635,628, filed Feb. 27, 2018, each of which applications is hereby incorporated herein by reference in its entirety.

STATEMENT REGARDING FEDERALLY SPONSORED RESEARCH OR DEVELOPMENT

This invention was made with government support under HHSN272201400005C awarded by the National Institutes of Health. The government has certain rights in the invention.

BACKGROUND OF THE INVENTION

Equine influenza, currently caused by H3N8 EIV, is the most common and important respiratory infectious disease of horses (Daly et al., 2011, Vet J, 189: 7-14; Timoney, 2000, Vet. Clin. North Am. Equine Pract. 16, 537-551). H3N8 EIV is highly contagious and has the potential to spread rapidly through groups of naive horses in aerosolized droplets that are dispersed by coughing (Daly et al., 2011, Vet J, 189: 7-14; Timoney, 2000, Vet. Clin. North Am. Equine Pract. 16, 537-551). H3N8 EIV infections of horses have been responsible for disrupting major equestrian events and causing significant economic losses (Daly et al., 2011, Vet J, 189: 7-14; Timoney, 2000, Vet. Clin. North Am. Equine Pract. 16, 537-551). The equine population is highly mobile, and horses travel long distances by road and/or air for competitions and breeding purposes. When an infected horse is introduced into a susceptible population, the spread of H3N8 EIV can be explosive. Large outbreaks of H3N8 EIV are often associated with the congregation of horses at equestrian events. Their dispersal after these events can lead to further widespread dissemination of the virus. It is currently estimated that H3N8 EIV outbreaks result in economic losses of hundreds of millions of dollars.

In endemic countries, the significant economic losses caused by H3N8 EIV infections can be minimized by vaccination of highly mobile horses. Indeed, many racing and equestrian authorities have mandatory vaccination policies that serve as insurance for business. On the other hand, non-endemic countries rely on vaccination of imported horses and quarantine to prevent an incursion of H3N8 EIV. The majority of these non-endemic countries also require vaccination of their indigenous horse population to reduce the potential impact of an H3N8 EIV incursion.

Traditional vaccination strategies support that vaccine strains must represent viruses in circulation, and it is only through surveillance that vaccine companies decide on which antigens should be used. Thus, EIV surveillance and strain characterization are fundamental for H3N8 EIV control programs based on vaccination. Importantly, vaccine manufacturers need to have a dynamic vaccination approach that allows the rapid generation of novel vaccines to benefit the equine population (Cullinane et al., 2010, Influenza Other Respir. Virus. 4, 339-344; Paillot, 2014, Vaccines 2, 797-831; Paillot et al., 2016, Pathogens 5). Results from cross-protection studies indicate that the majority of the inactivated vaccines or the current commercially available LAIV Flu Avert I.N. would provide poor levels of protection if used in the face of an imminent outbreak because of the antigenic differences between the virus in the vaccine and currently circulating H3N8 EIV strains (Paillot et al., 2016, Pathogens 5). Notably, some recent H3N8 EIV outbreaks occurred in previously vaccinated animals, where the vaccine strain did not match the circulating virus (Daly et al., 2003, Equine Vet. J. 35, 458-462; Garner et al., 2011, Prev. Vet. Med. 99, 15-27; Timoney, 2000, Vet. Clin. North Am. Equine Pract. 16, 537-551). The frequency of H3N8 EIV outbreaks, the continuous antigenic variation (antigenic drift) of H3N8 EIV and examples of vaccine breakdown due to poorly antigenic match demonstrate the periodic need to update EIV vaccines to prevent equine influenza in the equine population. Moreover, EIV vaccines should include both clade 1 and clade 2 representative strains of the Florida sublineage, as recommended by the OIE (Paillot et al., 2016, Pathogens 5).

Thus, there is a need in the art for improved vaccines for EIV. The present invention satisfies this unmet need.

SUMMARY OF THE INVENTION

In one aspect, the present invention provides a multivalent immunological composition comprising two or more equine live-attenuated influenza viruses (LAIV), comprising: a first LAIV expressing one or more antigens of a clade 1 H3N8 equine influenza virus; and a second LAIV expressing one or more antigens of a clade 2 H3N8 equine influenza virus, wherein each LAIV comprises one or more mutations in one or more of: segment 1 and segment 2 of the viral genome.

In one embodiment, the first LAIV expresses HA, NA, or a combination thereof of A/equine/Ohio/1/2003 H3N8. In one embodiment, the first LAIV expresses HA, NA, or a combination thereof of A/equine/Texas/6/2017 H3N8. In one embodiment, the second LAIV expresses HA, NA, or a combination thereof of A/equine/Richmond/1/2007 H3N8.

In one embodiment, segment 1 comprises the nucleic acid sequence set forth in SEQ ID NO: 1. In one embodiment, segment 2 comprises the nucleic acid sequence set forth in SEQ ID NO: 3.

In one embodiment, at least one LAIV comprises one or more mutations in segment 1, which encodes mutant PB2. In one embodiment, mutant PB2 comprises a N265S point mutation. In one embodiment, mutant PB2 comprises the amino acid sequence set forth in SEQ ID NO: 2.

In one embodiment, at least one LAIV comprises one or more mutations in segment 2, which encodes mutant PB1. In one embodiment, mutant PB1 comprises one or more of: K391E point mutation, E581G point mutation, and A661T point mutation. In one embodiment, mutant PB1 comprises a K391E point mutation, a E581G point mutation, and an A661T point mutation. In one embodiment, mutant PB1 comprises the amino acid sequence set forth in SEQ ID NO: 4.

In one embodiment, each LAIV comprises one or more mutations in segment 1, which encodes mutant PB2; and one or more mutations in segment 2, which encodes mutant PB1. In one embodiment, mutant PB2 comprises a N265S point mutation and mutant PB1 comprises a K391E point mutation, a E581G point mutation, and an A661T point mutation.

In one embodiment, the composition is used for the treatment of equine influenza in a subject.

In one embodiment, segment 1 of each LAIV is derived from segment 1 of A/equine/Ohio/1/2003; and wherein segment 2 of each LAIV is derived from segment 2 of A/equine/Ohio/1/2003.

In one aspect, the present invention provides a method for inducing an immune response against a plurality of equine influenza viruses in a subject, the method comprising administering to the subject a multivalent immunological composition comprising two or more equine live-attenuated influenza viruses (LAIV), comprising: a first LAIV expressing one or more antigens of a clade 1 H3N8 equine influenza virus; and a second LAIV expressing one or more antigens of a clade 2 H3N8 equine influenza virus, wherein each LAIV comprises one or more mutations in one or more of: segment 1 and segment 2 of the viral genome.

In one embodiment, the subject does not have equine influenza, and wherein the method induces immunity against equine influenza. In one embodiment, the subject is infected equine influenza, and wherein the method induces a therapeutic immune response.

In one embodiment, the immunological composition is administered intranasally, intratracheally, orally, intradermally, intramuscularly, intraperitoneally, intravenously, or subcutaneously. In one embodiment, the subject is a horse.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A and FIG. 1B, depicts the results of experiments demonstrating the effect of temperature on the polymerase activity of A/equine/Ohio/1/2003 H3N8 (EIV) live-attenuated influenza vaccine (LAIV). FIG. 1A: Schematic representation of segments 1 (PB2) and 2 (PB1) of WT (black) and LAIV (white) EIV (A/Equine/Ohio/1/2003): Amino acid substitutions in the polymerase PB2 (N265S) and PB1 (K391E, E581G, and A661T) subunits of A/equine/Ohio/1/2003 H3N8 are indicated. FIG. 1B: Minigenome activity: E. Derm cells (12-well plate format, $5 \times 10^5$ cells/well, triplicates) were transiently co-transfected with 0.25 μg of ambisense pDZ expression plasmids encoding the minimal requirements for viral genome replication and gene transcription (PB2, PB1, PA and NP), together with 0.5 μg of a vRNA-like expression plasmid encoding Gaussia luciferase (Gluc), and 0.1 μg of a pCAGGS Cypridinia luciferase (Cluc) plasmid to normalize transfection efficiencies. Six hours after transfection, cells were placed at 33° C., 37° C. or 39° C., and 48 h post-transfection, viral replication and transcription were evaluated by luminescence (Gluc). Gluc activity was normalized to that of Cluc. Data represent the means±SDs of the results determined for triplicate assays. Normalized reporter expression is relative to minigenome activity in the absence of the pDZ NP plasmid. Data are represented as relative activity considering WT EIV polymerase activity at each temperature as 100%. *, $P<0.005$; **, $P<0.001$; NS not statistical using the Student T test.

FIG. 2A and FIG. 2B, depicts the results of experiments evaluating the in vitro characterization of EIV LAIV. FIG. 2A: Multicycle growth kinetics: MDCK cells (12-well plate format, $5 \times 10^5$ cells/well, triplicates) were infected (MOI, 0.001) with A/equine/Ohio/1/2003 H3N8 WT (black diamonds) and LAIV (white diamonds) and incubated at 33° C., 37° C. and 39° C. As internal control, MDCK cells were also infected with Flu Avert I.N. (grey triangles). Viral titers in TCS at the indicated times post-infection were determined by immunofocus assay (FFU/ml) using an anti-NP mAb(HB-65). Data represent the means+/−SDs of the results determined in triplicate wells. Dotted black lines indicate the limit of detection (200 FFU/ml). $P<0.05$: *WT vs. LAIV, **WT vs. Flu Avert I.N. using the Student T test. FIG. 2B: Plaque phenotype: MDCK cells (6-well plate format, $1 \times 10^6$ cells/well) were infected with A/equine/Ohio/1/2003 H3N8 WT and LAIV and overlaid with media containing agar. MDCK cells infected with Flu Avert I.N. were included as internal control. Plates were incubated at 33° C., 37° C. and 39° C. and three days p.i., monolayers were immunostained with an anti-NP mAb (HB-65).

FIG. 3A and FIG. 3B, depict the results of example experiments demonstrating the attenuation of EIV LAIV in mice: Female 6-to-8-week-old C57BL/6 mice (N=6) were infected intranasally (i.n.) with $1 \times 10^5$ FFU of A/equine/Ohio/1/2003 H3N8 WT or LAIV. Mice were also infected with $1 \times 10^5$ FFU with Flu Avert I.N. as internal control. Presence of viruses in lungs (FIG. 3A) and nasal mucosa (FIG. 3B) of infected mice were evaluated at days 2 (N=3) and 4 (N=3) p.i. by immunofocus assay (FFU/ml) using an anti-NP mAb (HB-65). Data represent the means±SDs. Dotted black lines indicate the limit of detection (200 FFU/ml). ND, not detected. *, $P<0.05$ using the Student T test.

FIG. 4A and FIG. 4B, depicts the results of example experiments demonstrating the induction of humoral responses by EIV LAIV in mice: Female 6-to-8-week-old C57BL/6 mice (N=6) were vaccinated (i.n.) with $1 \times 10^3$ FFU of A/equine/Ohio/1/2003 H3N8 WT or LAIV. Mice were also mock (PBS) vaccinated or vaccinated (i.n.) with $1 \times 10^3$ FFU of Flu Avert I.N. as negative and positive controls, respectively. At 14 days post-vaccination, mice were bled and sera were collected and evaluated individually for the presence of total antibodies by ELISA (FIG. 4A) and neutralizing antibodies by HAI (FIG. 4B) against A/equine/Ohio/1/2003 H3N8. OD, optical density. Data represent the means+/−SDs of the results for 6 individual mice. ND, not detected. *, $P<0.05$ wt vs. LAIV; **, $P<0.005$ wt vs. Flu Avert I.N. using the Student T test.

FIG. 6A and FIG. 6B, depicts the results of example experiments demonstrating the attenuation of EIV LAIV in horses: One-to-two years-old horses of both sexes (N=4) were inoculated i.n. with $4 \times 10^8$ FFU of A/equine/Ohio/1/2003 H3N8 LAIV. FIG. 6A: Graphic representation of the individual rectal temperatures measured in each horse before (day 0) and during 3 days after vaccination. FIG. 6B: The virus content in nasopharyngeal swabs were determined by quantitative (q)RT-PCR and represented as quantification cycle threshold (Ct). The swabs were taken before (day 0) and during 3 days post-vaccination for each horse nostril. Data represent the means from each horse in each time post-vaccination ±SDs. Dotted black line indicates the limit of detection (Ct=40).

FIG. 7A and FIG. 7B, depicts the results of example experiments demonstrating the protection efficacy of EIV LAIV against EIV challenge in horses: One-to-two years-old horses of both sexes (N=4) were vaccinated by i.n. intubation with $4 \times 10^8$ FFU of A/equine/Ohio/1/2003 H3N8 LAIV. Another group of horses (N=2) were used as a control (unvaccinated). At 27 days post-vaccination, horses were challenged by aerosolized with $1 \times 10^7$ EID50 units per $m^3$ of wild-type EIV (Kentucky/2014 strain) into a tented stall (37.5 $m^3$) for 45 min. FIG. 7A: Rectal temperatures were measured daily by 10 days after challenge. FIG. 7B: Virus content in nasopharyngeal swabs taken during 7 days post-challenge was analyzed by (q)RT-PCR and represented as cycle threshold (Ct). Dotted black line indicates the limit of detection (Ct=40).

DETAILED DESCRIPTION

Figure 1:
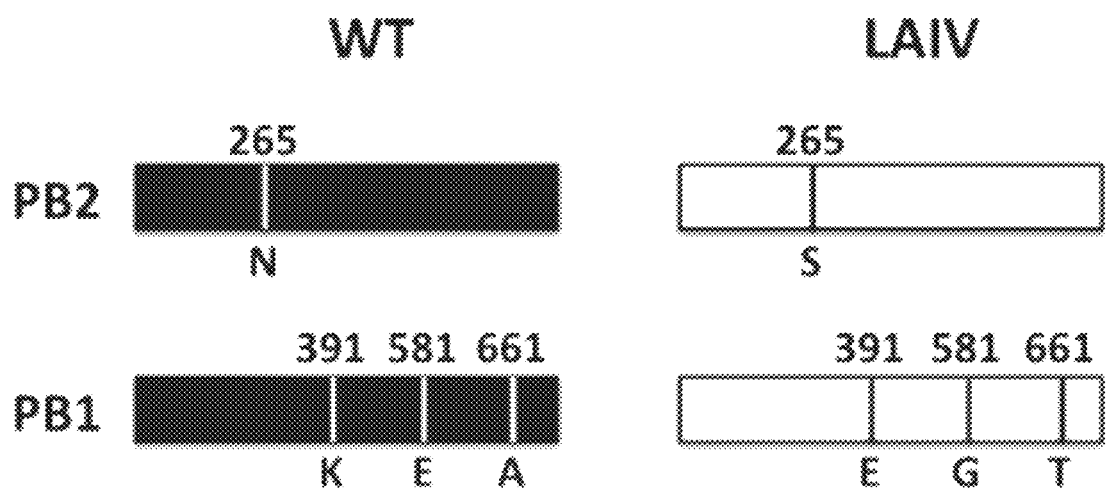
FIG. 1, comprising
Figure 1:
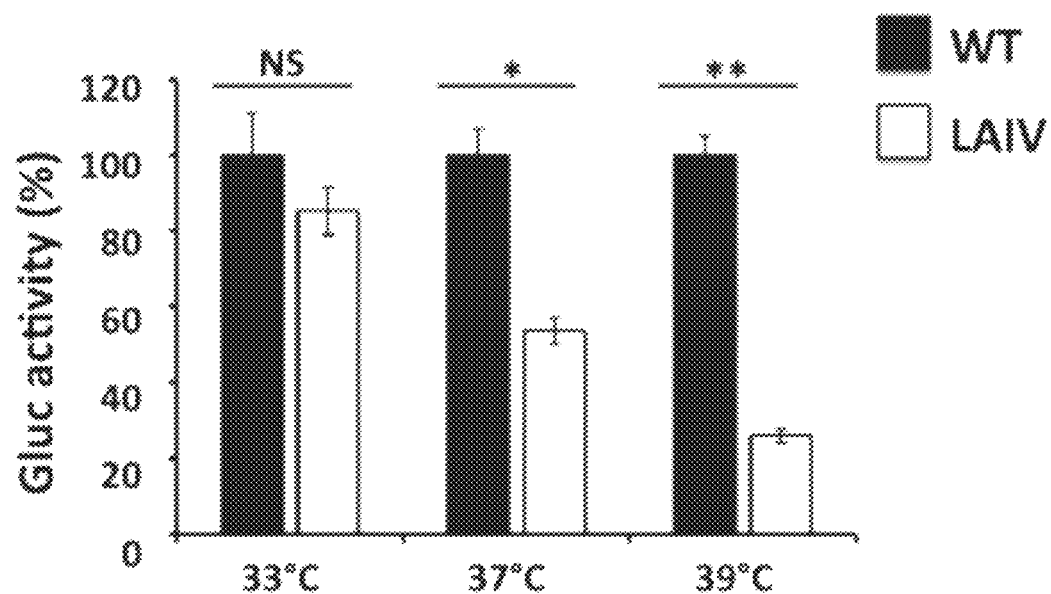

The present invention relates to compositions and methods for the treatment and prevention of equine influenza virus (EIV) and EIV-related pathology. The invention provides multivalent immunological compositions that provide protection against a plurality of EIV strains or clades. For example, in one embodiment the multivalent immunological composition provides protection against clade 1 H3N8 EIV and clade 2 H3N8 EIV.

The present invention is based in part upon the discovery that various mutations in segment 1 and segment 2 of the EIV genome, thereby encoding mutant PB2 and PB1 protein, render the virus to be temperature-sensitive. For example, it is described herein that such mutations result in EIV exhibiting reduced viral replication at normal and elevated body temperature as compared to wildtype EIV. However, the temperature-sensitive EIV is able to induce a EIV-specific immune response. Thus, the temperature-sensitive EIV described herein is a live-attenuated influenza vaccine (LAIV), sometimes referred to herein as EIV LAIV. Importantly, the presently described EIV LAIV is more effective in treating EIV compared to the commercially available vaccine.

Described herein is the development of an effective and safe LAIV for the prevention and control of H3N8 EIV in horses. Reverse genetic approaches along with modifications in the viral PB2 (N265S) and PB1 (K391E, E581G, and A661T) polymerase subunits of influenza A/equine/Ohio/1/2003 H3N8 virus was used to make a cold-adapted, temperature sensitive EIV H3N8 LAIV. Compared to current inactivated vaccines, the presently described cold-adapted, temperature sensitive LAIV approach provides better and long-lasting protection against disease caused by H3N8 EIV, because LAIV induces faster and stronger production of both innate and adaptive humoral and T-cell immune responses in the target tissues of the respiratory tract. Also, in certain instances the LAIV is administered through nasal spray, which avoids the swelling and muscle soreness associated with intramuscular infections of inactivated vaccines. Moreover, in some embodiments, a single immunization with the cold-adapted, temperature sensitive LAIV is sufficient, compared to the multiple doses required with the current inactivated vaccines, to confer full protection against H3N8 EIV in a shorter period of time. Further, the present LAIV technology would provide better cross protection against antigenically different EIV H3N8 strains than that provided by the current inactivated vaccines, diminishing the chance of H3N8 EIV outbreaks.

Compared to the only available EIV H3N8 LAIV, the present technology also offers a number of advantages. The mutations introduced in the PB2 and PB1 polymerase subunits of influenza A/equine/Ohio/1/2003 H3N8 are different than those generated by cold-adaptation of the current influenza A/equine/Kentucky/1/91 H3N8 LAIV; but able to confer similar cold-adapted, temperature sensitive phenotype to the virus. Moreover, the use of state-of-the-art reverse genetic techniques facilitates, similar to the case of human LAIV, the fast and accurate development of LAIV candidates for the treatment of currently circulating Florida clade 1 and 2 subtypes, or newly introduced H3N8 EIV strains. Thus, the present LAIV approach is more effective than the currently available LAIV to treat H3N8 EIV infections in horses because of strain match.

In certain embodiments, the invention relates to multivalent immunological composition comprising two or more EIV LAIVs. For example, in certain embodiments, the H3N8 LAIV described herein, based upon influenza A/equine/Ohio/1/2003 (a clade 1 strain), is used as a maser donor virus (MDV) to express antigens from different strains. For example, in one embodiment, the multivalent immunological composition comprises a first temperature sensitive LAIV and a second temperature sensitive LAIV, each comprising mutant segment 1 and/or mutant segment 2, where the first LAIV expresses one or more antigens of a first influenza strain and where the second LAIV expresses one or more antigens of a second influenza strain. The invention also encompasses multivalent immunological compositions comprising 3 or more, 4 or more, 5 or more, or 10 or more LAIVs, each LAIV expressing one or more antigens of a different influenza strain. The multivalent composition can be used to express antigens, such as HA and NA glycoproteins, from antigenically different clades or strains, thereby providing broad protection against a variety of circulating clades or strains.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

As used herein, the term "autologous" is meant to refer to any material derived from the same individual to which it is later to be re-introduced into the individual.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

The term "normal temperature" or "normal body temperature" as used herein refers to the temperature of a healthy subject. For example, in certain instances the "normal body temperature" in a human subject is in the range of about 36° C. to about 38° C. In certain instances, in an equine subject, "normal body temperature" is in the range of about 37.5° C. to about 38.7° C.

The term "elevated temperature" or "elevated body temperature" as used herein refers to a temperature in a subject that is greater than the "normal body temperature" of a subject of a given organism. In certain instances "elevated body temperature" may be indicative of a fever, infection, or other illness. In certain instances, elevated body temperature in a human subject is greater than about 37° C. In certain instances, elevated body temperature in an equine subject is greater than about 38.9° C.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides immunological compositions and methods useful for the inhibition, prevention and treatment of equine influenza and equine influenza related diseases and disorders. In one embodiment, the immunological composition comprises a live-attenuated virus (LAV). In one embodiment, the immunological composition is a multivalent composition comprising a plurality of LAVs, each expressing one or more antigens of different strains or clades of a virus, for example different strains or clades of influenza virus.

In one embodiment, the present invention provides a temperature-sensitive LAV of an equine influenza virus. For example, it is demonstrated herein that one or more mutations in segment 1 and/or segment 2 of the EIV genome renders the virus to be temperature-sensitive. The temperature-sensitive EIV LAIV of the present invention exhibits reduced viral replication, as compared to wildtype EIV, at both normal body temperature and at elevated or fever temperatures. However, the temperature sensitive EIV LAIV provides antigen-specific immune responses and protection against EIV. In one embodiment, the EIV LAIV provides at least the same antigen-specific immune responses and protection against EIV compared to wildtype EIV. In certain embodiments, the EIV LAIV provides greater antigen-specific immune responses and protection against EIV as compared to inactivated EIV.

In one embodiment, the composition comprises an EIV LAIV having one or more mutations in segment 1 and/or segment 2 of the viral genome. For example, in one embodiment, the EIV LAIV encodes mutant PB2 and/or mutant PB1. In certain embodiments, mutant PB2 comprises a N265S point mutation. In certain embodiments, mutant PB1 comprises at least one of a K391E point mutation, a E581G point mutation, or A661T point mutation.

In certain embodiments, the EIV LAIV described herein is used as a master donor virus (MDV), having one or more mutations in segment 1 and/or segment 2 of the viral genome, to express one or more antigens of different strains or clades of influenza virus. In one embodiment, the MDV comprises mutant H3N8 segment 1 and/or segment 2, as described herein. In certain embodiments, the MDV can be used to generate an LAIV which is protective against other pathogens. For example, in certain embodiments, an LAIV against another influenza strain can be generated by using the MDV to express one or more viral proteins (e.g., HA or NA) of the other strain. For example, in one embodiment, the composition comprises a multivalent immunological composition comprising a plurality of LAIVs, each designed to express one or more antigens of a different clade or strain of influenza virus.

In one embodiment, the composition comprises a first LAIV expressing one or more antigens of a clade 1 H3N8 influenza virus and a second LAIV expressing one or more antigens of a clade 2 H3N8 influenza virus.

In one embodiment, the composition comprises a LAIV expressing one or more antigens of clade 1 A/equine/Ohio/1/2003 H3N8. In one embodiment, the composition comprises a LAIV expressing one or more antigens of clade 2 A/equine/Richmond/1/2007 H3N8. In one embodiment, the composition comprises an LAIV expressing one or more antigens of clade 1 A/equine/Texas/6/2017 H3N8.

In one embodiment, the composition comprises a first LAIV expressing one or more antigens of A/equine/Ohio/1/2003 H3N8 and a second LAIV expressing one or more antigens of A/equine/Richmond/1/2007 H3N8.

In one embodiment, the composition comprises a first LAIV expressing one or more antigens of A/equine/Texas/6/2017 H3N8 and a second LAIV expressing one or more antigens of A/equine/Richmond/1/2007 H3N8.

In certain embodiments, the present invention provides a method for treating or preventing EIV and EIV-related pathology, comprising administering a composition comprising an EIV LAIV. In certain embodiments, the method comprises intranasal delivery of the EIV LAIV.

In general, wild-type influenza viruses contain a segmented genome with 8 segments as described in Table 1 below:

TABLE 1

| Segment | Gene Product |
| --- | --- |
| 1 | PB2 (Polymerase (basic) protein 2) |
| 2 | PB1 (Polymerase (basic) protein 1) |
| 3 | PA (Polymerase (acidic) protein) |
| 4 | HA (Hemagglutinin) |
| 5 | NP (Nucleoprotein) |
| 6 | NA (Neuraminidase) |
| 7 | M1 (Matrix protein 1) and M2 (Matrix protein 2) |
| 8 | NS1 (non-structural protein 1) and NEP/NS2 (non-structural protein 2) |

In certain embodiments, the present invention provides an immunological composition comprising segment 1 and/or segment 2, wherein segment 1 and/or segment 2 comprise one or more mutations. For example, in certain embodiments, the immunological composition comprises an LAIV, comprising one or more mutations in segment 1 and/or segment 2. In one embodiment, the immunological composition comprises an EIV LAIV, comprising one or more mutations in segment 1 and/or segment 2.

The present invention also provides methods of preventing, inhibiting, and treating EIV and EIV-related diseases and disorders. In one embodiment, the methods of the invention induce immunity against EIV by generating an immune response directed to EIV. In one embodiment, the methods of the invention induce production of EIV-specific antibodies. In one embodiment, the methods of the invention prevent EIV-related pathology. In one embodiment, the methods of the invention comprise administering an immunological composition comprising a LAIV, wherein the LAIV comprises one or more mutations in segment 1 and/or segment 2, to a subject in need thereof. In one embodiment, the methods comprise administering an immunological composition to a subject in need thereof, thereby inducing immunity to EIV.

Compositions

The present invention provides immunological compositions that when administered to a subject in need thereof, elicit an immune response directed against equine influenza virus (EIV). In some embodiments, the composition includes polypeptides, nucleotides, vectors, or vaccines. Further, when the compositions are administered to a subject, they elicit an immune response that serves to protect the inoculated subject against equine influenza. As exemplified herein, the composition can be obtained in large quantities for use as a vaccine.

In one embodiment, the present invention provides compositions that are useful as immunomodulatory agents, for example, in stimulating immune responses and in preventing equine influenza and equine influenza-related pathology.

Live-attenuated viruses can be used as immunostimulatory agents to induce the production of EIV-specific antibodies and protect against equine influenza and equine influenza-related pathology. Therefore, in one embodiment, the composition of the invention comprises a live-attenuated EIV (EIV LAIV), wherein the EIV LAIV comprises one or more mutations in the viral genome to render the EIV LAIV temperature sensitive. For example, in one embodiment, the EIV LAIV comprises one or more mutations in segment 1 of the viral genome. The one or more mutations in segment 1 of the viral genome encode a mutant PB2 protein. In one embodiment, the EIV LAIV comprises one or more mutations in segment 2 of the viral genome. The one or more mutations in segment 2 of the viral genome encode a mutant PB1 protein. In one embodiment, the EIV LAIV comprises one or more mutations in segment 1 and one or more mutations in segment 2.

In one embodiment, the EIV LAIV is based upon the genome of Influenza A/equine/Ohio/1/2003 H3N8. Wild-type nucleic acid sequences for each segment of Influenza A/equine/Ohio/1/2003 H3N8 and wildtype amino acid sequences for the encoded proteins are summarized in Table 2 below:

TABLE 2

Wildtype sequences for Influenza A/equine/Ohio/1/2003 H3N8

| Segments | Gene Products |
| --- | --- |
| Segment 1 (SEQ ID NO: 5) | PB2 (SEQ ID NO: 6) |
| Segment 2 (SEQ ID NO: 7) | PB1 (SEQ ID NO: 8) |
| Segment 3 (SEQ ID NO: 9) | PA (SEQ ID NO: 10) |
| Segment 4 (SEQ ID NO: 11) | HA (SEQ ID NO: 12) |

TABLE 2-continued

Wildtype sequences for Influenza A/equine/Ohio/1/2003 H3N8

| Segments | Gene Products | |
|---|---|---|
| Segment 5 (SEQ ID NO: 13) | NP (SEQ ID NO: 14) | |
| Segment 6 (SEQ ID NO: 15) | NA (SEQ ID NO: 16) | |
| Segment 7 (SEQ ID NO: 17) | M1 (SEQ ID NO: 18) | M2 (SEQ ID NO: 19) |
| Segment 8 (SEQ ID NO: 20) | NS1 (SEQ ID NO: 21) | NEPN52 (SEQ ID NO: 22) |

In one embodiment, the composition comprises one or more mutations in the nucleic acid sequences of segment 1, encoding PB2, and/or segment 2, encoding PB1. Thus, in certain embodiments, the composition encodes mutant PB1 and/or mutant PB2. As described herein, the one or more mutations renders the virus to be temperature-sensitive, exhibited reduced viral replication at normal or elevated temperatures.

In some embodiments, the invention provides a composition comprising one or more mutations in segment 1. For example, in one embodiment, the composition comprises segment 1 having one or more mutation which results in the production of mutant PB2 having a point mutation at amino acid residue 265. For example, in one embodiment, the mutant PB2 comprises the amino acid sequence of SEQ ID NO: 6, except having a point mutation at amino acid residue 265. For example, in one embodiment, the mutant PB2 comprises a N265S point mutation, where the mutant PB2 comprises a serine at amino acid residue 265.

In one embodiment, the composition comprises a nucleic acid sequence encoding a mutant PB2 having an amino acid sequence of SEQ ID NO: 2. In one embodiment, the composition comprises a nucleic acid sequence encoding a mutant PB2 that is substantially homologous to SEQ ID NO: 2. For example, in certain embodiments, the composition comprises a nucleic acid sequence that encodes a mutant PB2 that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 2. In one embodiment, the composition comprises a nucleic acid sequence encoding a mutant PB2 that is substantially homologous to SEQ ID NO: 2, where mutant PB2 that is substantially homologous to SEQ ID NO: 2 comprises the N265S point mutation.

In one embodiment, the composition comprises a mutant segment 1 comprising the nucleotide sequence of SEQ ID NO: 1. In one embodiment, the composition comprises nucleotide sequence that is substantially homologous to SEQ ID NO: 1. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 1. In one embodiment, the composition comprises a nucleotide sequence that is substantially homologous to SEQ ID NO: 1, where the mutant PB2 encoded by the nucleotide sequence that is substantially homologous to SEQ ID NO: 1 comprises the N265S point mutation.

In some embodiments, the invention provides a composition comprising one or more mutations in segment 2. For example, in one embodiment, the composition comprises segment 2 having one or more mutation which results in the production of mutant PB1 having a point mutation at one or more of: amino acid residue 391, amino acid residue 581, and amino acid residue 661. For example, in one embodiment, the mutant PB2 comprises the amino acid sequence of SEQ ID NO: 8, except having a point mutation at one or more of: amino acid residue 391, amino acid residue 581, and amino acid residue 661. For example, in one embodiment, the mutant PB1 comprises a K391E point mutation, where the mutant PB1 comprises a glutamic acid at amino acid residue 391. In one embodiment, the mutant PB1 comprises a E581G point mutation, where the mutant PB1 comprises a glycine at amino acid residue 581. In one embodiment, the mutant PB1 comprises a A661T point mutation, where the mutant PB1 comprises a threonine at amino acid residue 661.

In one embodiment, the composition comprises a nucleic acid sequence encoding a mutant PB1 having an amino acid sequence of SEQ ID NO: 4. In one embodiment, the composition comprises a nucleic acid sequence encoding a mutant PB1 that is substantially homologous to SEQ ID NO: 4. For example, in certain embodiments, the composition comprises a nucleic acid sequence that encodes a mutant PB1 that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 4. In one embodiment, the composition comprises a nucleic acid sequence encoding a mutant PB1 that is substantially homologous to SEQ ID NO: 4, where mutant PB1 that is substantially homologous to SEQ ID NO: 4 comprises one or more of the K391E point mutation, E581G point mutation, and A661T point mutation.

In one embodiment, the composition comprises a mutant segment 2 comprising the nucleotide sequence of SEQ ID NO: 3. In one embodiment, the composition comprises nucleotide sequence that is substantially homologous to SEQ ID NO: 3. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 3. In one embodiment, the composition comprises a nucleotide sequence that is substantially homologous to SEQ ID NO: 3, where the mutant PB1 encoded by the nucleotide sequence that is substantially homologous to SEQ ID NO: 3 comprises one or more of the K391E point mutation, E581G point mutation, and A661T point mutation.

In certain embodiments, the composition comprises one or more mutations in segment 1 and one or more mutations in segment 2. For example, in certain embodiments, the composition comprises segment 1 having a N265S point mutation, and segment 2 having one or more of K391E point mutation, E581G point mutation, and A661T point mutation.

In certain embodiments, the composition comprises one or more mutations in the nucleic acid sequences of segment 1 and/or segment 2, while comprising wildtype nucleic acid sequences for the rest of the segmented genome. For example, in one embodiment, the EIV LAIV comprises one or more mutations in segment 1 and comprises wildtype segment 2, segment 3, segment 4, segment 5, segment 6, segment 7, and segment 8. In one embodiment, the EIV LAIV comprises one or more mutation is segment 2 and comprises wildtype segment 1, segment 3, segment 4, segment 5, segment 6, segment 7, and segment 8. In one embodiment, the EIV LAIV comprises one or more mutations in segment 1 and segment 2 and comprises wildtype segment 3, segment 4, segment 5, segment 6, segment 7, and segment 8.

In certain embodiments, the composition comprises one or more mutations in segment 1 and/or segment 2, in combination with one or more mutations in one or more other segments of the viral genome.

In one embodiment, the composition comprises a LAIV comprising mutant segment 1, mutant segment 2, or a combination thereof based upon A/equine/Ohio/1/2003 H3N8, and comprising segment 4 and segment 6 of A/equine/Ohio/1/2003 H3N8 thereby providing protection against clade 1 H3N8.

The nucleotide sequence of segment 4 of A/equine/Ohio/1/2003 H3N8 is provided by SEQ ID NO: 11. The amino acid sequence of HA protein of A/equine/Ohio/1/2003 H3N8 is provided by SEQ ID NO: 12.

The nucleotide sequence of segment 6 of A/equine/Ohio/1/2003 H3N8 is provided by SEQ ID NO: 15. The amino acid sequence of NA protein of A/equine/Ohio/1/2003 H3N8 is provided by SEQ ID NO: 16.

In one embodiment, the composition comprises a LAIV comprising mutant segment 1, mutant segment 2, or a combination thereof based upon A/equine/Ohio/1/2003 H3N8, and comprising segment 4, encoding HA of A/equine/Ohio/1/2003 H3N8, and segment 6, encoding NA of A/equine/Ohio/1/2003 H3N8, wherein HA of A/equine/Ohio/1/2003 H3N8 comprises SEQ ID NO: 12 and wherein NA of A/equine/Ohio/1/2003 H3N8 comprises SEQ ID NO: 16.

In one embodiment, the composition comprises a LAIV comprising mutant segment 1, mutant segment 2, or a combination thereof based upon A/equine/Ohio/1/2003 H3N8, and comprising segment 4 of A/equine/Ohio/1/2003 H3N8, and segment 6 of A/equine/Ohio/1/2003 H3N8, wherein segment 4 of A/equine/Ohio/1/2003 H3N8 comprises SEQ ID NO: 11 and wherein segment 6 of A/equine/Ohio/1/2003 H3N8 comprises SEQ ID NO:15.

In certain embodiments, the composition comprises a mutant segment 1, mutant segment 2, or combination thereof, as described herein, in combination with one or more nucleotide sequences encoding another antigen. For example, in certain embodiments, the composition comprises a mutant segment 1, mutant segment 2, or combination thereof, as described herein, in combination with one or more nucleotide sequences encoding one or more antigens of another virus or strain. For example, in certain aspects, the H3N8 EIV LAIV described herein, comprising a mutant segment 1, mutant segment 2, or combination thereof can be used as a master donor virus (MDV). For example, an MDV comprising an H3N8 comprising a mutant segment 1, mutant segment 2, or combination thereof described herein, can be modified to comprise one or more nucleotide sequences encoding one or more of PB2, PB1, PA, NP, HA, NA, M1, M2, NS1, or NEP/NS2 from another influenza strain. As such a composition comprising an H3N8 comprising a mutant segment 1, mutant segment 2, or combination thereof described herein can provide protection against a different strain, when the composition expresses an antigen of the different strain. For example, in one embodiment, a composition comprises the backbone of a H3N8 EIV LAIV comprising a mutant segment 1, mutant segment 2, or combination thereof described herein, further comprising one or more nucleotide sequences encoding one or more of PB2, PB1, PA, NP, HA, NA, M1, M2, NS1, or NEP/NS2 from another influenza strain. In one embodiment, the composition comprises the backbone of a H3N8 EIV LAIV comprising a mutant segment 1, mutant segment 2, or combination thereof described herein, further comprising one or more nucleotide sequences encoding one or more HA or NA of a different influenza strain. For example, the composition comprising the backbone of a H3N8 EIV LAIV described herein, may be modified to express one or more viral proteins of a newly emergent strain, thereby providing protection against the newly emergent strain.

In one embodiment, the composition comprises segment 1, segment 2, segment 3, segment 5, segment 7, and segment 8 of H3N8 EIV LAIV, described herein, comprising one or more point mutations in one or more of segment 1 and segment 2, where the composition further comprises segment 4 and segment 6, of a different EIV strain.

In one embodiment, the composition comprises a mutant segment 1 of H3N8, mutant segment 2 of H3N8, or a combination thereof, further comprising segment 4, segment 6, or a combination thereof of a different EIV strain. In certain aspects, the mutant segment 1, mutant segment 2, or combination thereof of H3N8 provides for the temperature sensitive attenuated phenotype of the EIV LAIV, while the segment 4, segment 6, or combination thereof, of the different EIV strain, encodes HA, NA, or combination thereof of the different EIV strain to elicit a specific immune response to the different EIV strain in the subject.

In one embodiment, the composition comprises a multivalent vaccine comprising a plurality of EIV LAIV described herein. For example, in one embodiment, the composition comprises a first EIV LAIV, comprising mutant segment 1, mutant segment 2, or combination thereof of H3N8, where the first EIV LAIV comprises segment 4, segment 6, or a combination thereof of H3N8; and the composition further comprises a second EIV LAIV, comprising mutant segment 1, mutant segment 2, or combination thereof of H3N8, where the second EIV LAIV comprises segment 4, segment 6, or a combination thereof of a different EIV strain. In certain embodiments, the composition induces an immune response against both H3N8 and the other EIV strain.

Exemplary EIV strains that may be included in the multivalent vaccine include, but is not limited to, 2006-2007 European strain Newmarket/2003-like and the Florida clade 1 strains South Africa/03-like, Ohio/03-like and Notss/09-like, and the Florida clade 2 strains Richmond/07-like, Lancashire/10-like or Hants/10-like.

In one embodiment, the composition comprises a LAIV comprising mutant segment 1, mutant segment 2, or a combination thereof based upon A/equine/Ohio/1/2003 H3N8, but further comprising segment 4 and segment 6 of A/equine/Richmond/1/2007 H3N8; thereby providing protection against clade 2 H3N8.

The nucleotide sequence of segment 4 of A/equine/Richmond/1/2007 H3N8 is provided by SEQ ID NO: 23. The amino acid sequence of HA protein of A/equine/Richmond/1/2007 H3N8 is provided by SEQ ID NO: 24.

The nucleotide sequence of segment 6 of A/equine/Richmond/1/2007 H3N8 is provided by SEQ ID NO: 25. The amino acid sequence of NA protein of A/equine/Richmond/1/2007 H3N8 is provided by SEQ ID NO: 26.

In one embodiment, the composition comprises a LAIV comprising mutant segment 1, mutant segment 2, or a combination thereof based upon A/equine/Ohio/1/2003 H3N8, but further comprising segment 4, encoding HA of A/equine/Richmond/1/2007 H3N8, and segment 6, encoding NA of A/equine/Richmond/1/2007 H3N8, wherein HA of A/equine/Richmond/1/2007 H3N8 comprises SEQ ID NO: 24 and wherein NA of A/equine/Richmond/1/2007 H3N8 comprises SEQ ID NO: 26.

In one embodiment, the composition comprises a LAIV comprising mutant segment 1, mutant segment 2, or a combination thereof based upon A/equine/Ohio/1/2003 H3N8, but further comprising segment 4 of A/equine/Richmond/1/2007 H3N8, and segment 6 of A/equine/Richmond/1/2007 H3N8, wherein segment 4 of A/equine/Richmond/1/2007 H3N8 comprises SEQ ID NO: 23 and wherein segment 6 of A/equine/Richmond/1/2007 H3N8 comprises SEQ ID NO: 25.

In one embodiment, the composition comprises (1) a first LAIV comprising mutant segment 1, mutant segment 2, or a combination thereof based upon the A/equine/Ohio/1/2003 H3N8, and further comprising segment 4 and segment 6 of A/equine/Ohio/1/2003 H3N8, and (2) a second LAIV comprising mutant segment 1, mutant segment 2, or a combination thereof based upon A/equine/Ohio/1/2003 H3N8, but further comprising segment 4 and segment 6 of A/equine/Richmond/1/2007 H3N8; thereby providing protection against clade 1 and clade 2 H3N8.

In one embodiment, the composition comprises a first LAIV comprising mutant segment 1, mutant segment 2, or a combination thereof based upon the A/equine/Ohio/1/2003 H3N8, and further comprising segment 4, encoding HA of A/equine/Ohio/1/2003 H3N8, and segment 6, encoding NA of A/equine/Ohio/1/2003 H3N8, wherein HA of A/equine/Ohio/1/2003 H3N8 comprises SEQ ID NO: 12 and wherein NA of A/equine/Ohio/1/2003 H3N8 comprises SEQ ID NO: 16. In one embodiment, the composition comprises a second LAIV comprising mutant segment 1, mutant segment 2, or a combination thereof based upon A/equine/Ohio/1/2003 H3N8, but further comprising segment 4, encoding HA of A/equine/Richmond/1/2007 H3N8, and segment 6, encoding NA of A/equine/Richmond/1/2007 H3N8, wherein HA of A/equine/Richmond/1/2007 H3N8 comprises SEQ ID NO: 24 and wherein NA of A/equine/Richmond/1/2007 H3N8 comprises SEQ ID NO: 26.

In one embodiment, the composition comprises a first LAIV comprising mutant segment 1, mutant segment 2, or a combination thereof based upon the A/equine/Ohio/1/2003 H3N8, and further comprising segment 4 of A/equine/Ohio/1/2003 H3N8, and segment 6 of A/equine/Ohio/1/2003 H3N8, wherein segment 4 of A/equine/Ohio/1/2003 H3N8 comprises SEQ ID NO: 11 and wherein segment 6 of A/equine/Ohio/1/2003 H3N8 comprises SEQ ID NO: 15. In one embodiment, the composition comprises a second LAIV comprising mutant segment 1, mutant segment 2, or a combination thereof based upon A/equine/Ohio/1/2003 H3N8, but further comprising segment 4 of A/equine/Richmond/1/2007 H3N8, and segment 6 of A/equine/Richmond/1/2007 H3N8, wherein segment 4 of A/equine/Richmond/1/2007 H3N8 comprises SEQ ID NO: 23 and wherein segment 6 of A/equine/Richmond/1/2007 H3N8 comprises SEQ ID NO: 25.

In one embodiment, the composition comprises a LAIV comprising mutant segment 1, mutant segment 2, or a combination thereof based upon A/equine/Ohio/1/2003 H3N8, but further comprising segment 4 and segment 6 of A/equine/Texas/6/2017 H3N8; thereby providing protection against clade 1 H3N8.

The nucleotide sequence of segment 4 of A/equine/Texas/6/2017 H3N8 is provided by SEQ ID NO: 27. The amino acid sequence of HA protein of A/equine/Texas/6/2017 H3N8 is provided by SEQ ID NO: 28.

The nucleotide sequence of segment 6 of A/equine/Texas/6/2017 H3N8 is provided by SEQ ID NO: 29. The amino acid sequence of NA protein of A/equine/Texas/6/2017 H3N8 is provided by SEQ ID NO: 30.

In one embodiment, the composition comprises a LAIV comprising mutant segment 1, mutant segment 2, or a combination thereof based upon A/equine/Ohio/1/2003 H3N8, but further comprising segment 4, encoding HA of A/equine/Texas/6/2017 H3N8, and segment 6, encoding NA of A/equine/Texas/6/2017 H3N8, wherein HA of A/equine/Texas/6/2017 H3N8 comprises SEQ ID NO: 28 and wherein NA of A/equine/Texas/6/2017 H3N8 comprises SEQ ID NO: 30.

In one embodiment, the composition comprises a LAIV comprising mutant segment 1, mutant segment 2, or a combination thereof based upon A/equine/Ohio/1/2003 H3N8, but further comprising segment 4 of A/equine/Texas/6/2017 H3N8, and segment 6 of A/equine/Texas/6/2017 H3N8, wherein segment 4 of A/equine/Texas/6/2017 H3N8 comprises SEQ ID NO: 27 and wherein segment 6 of A/equine/Texas/6/2017 H3N8 comprises SEQ ID NO: 29.

In one embodiment, the composition comprises (1) a first LAIV comprising mutant segment 1, mutant segment 2, or a combination thereof based upon the A/equine/Ohio/1/2003 H3N8, and further comprising segment 4 and segment 6 of A/equine/Texas/6/2017 H3N8, and (2) a second LAIV comprising mutant segment 1, mutant segment 2, or a combination thereof based upon A/equine/Ohio/1/2003 H3N8, but further comprising segment 4 and segment 6 of A/equine/Richmond/1/2007 H3N8; thereby providing protection against clade 1 and clade 2 H3N8.

In one embodiment, the composition comprises a first LAIV comprising mutant segment 1, mutant segment 2, or a combination thereof based upon the A/equine/Ohio/1/2003 H3N8, and further comprising segment 4, encoding HA of A/equine/Texas/6/2017 H3N8, and segment 6, encoding NA of A/equine/Texas/6/2017 H3N8, wherein HA of A/equine/Texas/6/2017 H3N8 comprises SEQ ID NO: 28 and wherein NA of A/equine/Texas/6/2017 H3N8 comprises SEQ ID NO: 30. In one embodiment, the composition comprises a second LAIV comprising mutant segment 1, mutant segment 2, or a combination thereof based upon A/equine/Ohio/1/2003 H3N8, but further comprising segment 4, encoding HA of A/equine/Richmond/1/2007 H3N8, and segment 6, encoding NA of A/equine/Richmond/1/2007 H3N8, wherein HA of A/equine/Richmond/1/2007 H3N8 comprises SEQ ID NO: 24 and wherein NA of A/equine/Richmond/1/2007 H3N8 comprises SEQ ID NO: 26.

In one embodiment, the composition comprises a first LAIV comprising mutant segment 1, mutant segment 2, or a combination thereof based upon the A/equine/Ohio/1/2003 H3N8, and further comprising segment 4 of A/equine/Texas/6/2017 H3N8, and segment 6 of A/equine/Texas/6/2017 H3N8, wherein segment 4 of A/equine/Texas/6/2017 H3N8 comprises SEQ ID NO: 27 and wherein segment A/equine/Texas/6/2017 H3N8 comprises SEQ ID NO: 29. In one embodiment, the composition comprises a second LAIV comprising mutant segment 1, mutant segment 2, or a combination thereof based upon A/equine/Ohio/1/2003 H3N8, but further comprising segment 4 of A/equine/Richmond/1/2007 H3N8, and segment 6 of A/equine/Richmond/1/2007 H3N8, wherein segment 4 of A/equine/Richmond/1/2007 H3N8 comprises SEQ ID NO: 23 and wherein segment 6 of A/equine/Richmond/1/2007 H3N8 comprises SEQ ID NO: 25.

In certain embodiments, the composition comprises a polynucleotide encoding mutant PB2 and/or mutant PB1. The polynucleotide can be RNA or DNA. In one embodiment, the composition comprises a DNA vaccine.

The nucleic acid sequences include both the DNA sequence that is transcribed into RNA and the RNA sequence that is translated into a polypeptide. According to other embodiments, the polynucleotides of the invention are inferred from the amino acid sequence of the polypeptides of the invention. As is known in the art several alternative polynucleotides are possible due to redundant codons, while retaining the biological activity of the translated polypeptides.

Further, the invention encompasses an isolated nucleic acid comprising a nucleotide sequence having substantial homology to a nucleotide sequence of an isolated nucleic acid encoding a polypeptide disclosed herein. Preferably, the nucleotide sequence of an isolated nucleic acid encoding a polypeptide of the invention is "substantially homologous," that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a polypeptide of the invention.

It is to be understood explicitly that the scope of the present invention encompasses homologs, analogs, variants, fragments, derivatives and salts, including shorter and longer polypeptides and polynucleotides, as well as polypeptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the immunologic activity of the original molecule. Specifically any active fragments of the active polypeptides as well as extensions, conjugates and mixtures are included and are disclosed herein according to the principles of the present invention.

The invention should be construed to include any and all isolated nucleic acids which are homologous to the nucleic acids described and referenced herein, provided these homologous nucleic acids encode polypeptides having the biological activity of the polypeptides disclosed herein.

The skilled artisan would understand that the nucleic acids of the invention encompass a RNA or a DNA sequence encoding a polypeptide of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). Procedures for the introduction of amino acid changes in a polypeptide or polypeptide by altering the DNA sequence encoding the polypeptide are well known in the art and are also described in these, and other, treatises.

According to yet another embodiment, composition of the invention, comprising the nucleic acid sequences or combination of nucleic acid sequences of the present invention, is capable of generating an EIV-specific immune response. In another embodiment, the composition of the invention, comprising the nucleic acid sequences or combination of nucleic acid sequences of the present invention, is capable of generating EIV-specific antibodies. In certain embodiments, the composition is able to protect against EIV, including H3N8 EIV. In certain embodiments, the composition is able to protect against a plurality of clades or strains of EIV.

In one embodiment, the composition of the invention comprises a polypeptide, or a fragment of a polypeptide, a homolog, a variant, a derivative or a salt of a polypeptide having the sequence of any one or more of SEQ ID NO: 2 and SEQ ID NO: 4.

The invention should also be construed to include any form of a polypeptide having substantial homology to the polypeptides disclosed herein. Preferably, a polypeptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the polypeptides disclosed herein.

According to yet another embodiment, composition of the invention, comprising the polypeptide or combination of polypeptides of the present invention, is capable of generating an EIV-specific immune response. In another embodiment, the composition of the invention, comprising the polypeptide or combination of polypeptides of the present invention, is capable of generating EIV-specific antibodies. In certain embodiments, the composition is able to protect against EIV, including H3N8 EIV.

The present invention should also be construed to encompass "mutants," "derivatives," and "variants" of the polypeptides of the invention (or of the DNA encoding the same) which mutants, derivatives and variants are polypeptides which are altered in one or more amino acids (or, when referring to the nucleotide sequence encoding the same, are altered in one or more base pairs) such that the resulting polypeptide (or DNA) is not identical to the sequences recited herein, but has the same biological property as the polypeptides disclosed herein.

Live Attenuated Virus (LAV)

The invention relates in part to the generation, selection and identification of live attenuated viruses (LAV) that generate a EIV-specific immune response, and the use of such viruses in vaccine and pharmaceutical formulations.

As described herein, in certain embodiments the EIV LAIV comprises one or more mutations in segment 1 and/or one or more mutations in segment 2 that render the virus to be temperature-sensitive. For example, in one embodiment, the temperature-sensitive EIV LAIV exhibits reduced viral replication at normal and elevated temperatures. However, the temperature-sensitive EIV LAIV induces EIV-specific immune responses and antibody production, and is thus able to protect against EIV and EIV-related pathology.

Any mutant virus or strain which has at least one mutation can be selected and used in accordance with the invention. In one embodiment, naturally occurring mutants or variants, or spontaneous mutants can be selected that include at least one mutation in segment 1 and/or segment 2, as described elsewhere herein. In another embodiment, mutant viruses can be generated by exposing the virus to mutagens, such as ultraviolet irradiation or chemical mutagens, or by multiple passages and/or passage in non-permissive hosts. Screening in a differential growth system can be used to select for those mutants having at least one mutation in segment 1 and/or segment 2, as described elsewhere herein. For viruses with segmented genomes, the attenuated phenotype can be transferred to another strain having a desired antigen by reassortment, (i.e., by coinfection of the attenuated virus and the desired strain, and selection for reassortants displaying both phenotypes).

In another embodiment, mutations can be engineered into an influenza virus, including, but not limited to H3N8 EIV using "reverse genetics" approaches. In this way, natural or other mutations which confer the attenuated phenotype can be engineered into vaccine strains. For example, deletions, insertions, or substitutions of the coding region of segment 1, encoding PB2, and/or segment 2, encoding PB1 can be engineered. Deletions, substitutions or insertions in the non-coding region of segment 1 and/or segment 2 are also contemplated. To this end, mutations in the signals responsible for the transcription, replication, polyadenylation and/or packaging of segment 1 and/or segment 2 can be engineered.

In certain instances, the reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. In some instances, a more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152, 845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain.

In an alternate embodiment, a combination of reverse genetics techniques and reassortant techniques can be used to engineer attenuated viruses having the desired epitopes. For example, an attenuated virus (generated by natural selection, mutagenesis or by reverse genetics techniques) and a strain carrying the desired vaccine epitope (generated by natural selection, mutagenesis or by reverse genetics techniques) can be co-infected in hosts that permit reassortment of the segmented genomes. Reassortants that display both the attenuated phenotype and the desired epitope can then be selected.

The attenuated virus of the present invention can itself be used as the active ingredient in vaccine or pharmaceutical formulations. In certain embodiments, the attenuated virus can be used as the vector or "backbone" of recombinantly produced vaccines. To this end, the "reverse genetics" technique can be used to engineer mutations or introduce foreign epitopes into the attenuated virus, which would serve as the "parental" strain. In this way, vaccines can be designed for immunization against strain variants, or in the alternative, against completely different infectious agents or disease antigens.

For example, in one embodiment, the immunological composition of the invention comprises a live attenuated virus, engineered to express one or more epitopes or antigens of EIV along with epitopes or antigens of another pathogen. For example, the attenuated virus can be engineered to express neutralizing epitopes of other preselected strains. Alternatively, epitopes of other viruses can be built into the attenuated mutant virus. Alternatively, epitopes of non-viral infectious pathogens (e.g., parasites, bacteria, fungi) can be engineered into the virus.

In one embodiment, the attenuated viruses selected for use in the invention is capable of inducing a robust anti-EIV response in the host—a feature which contributes to the generation of a strong immune response when used as a vaccine, and which has other biological consequences that make the viruses useful as pharmaceutical agents for the prevention and/or treatment of other viral infections, or other diseases.

The attenuated viruses, which induce a EIV-specific immune response in hosts, may also be used in pharmaceutical formulations for the prophylaxis or treatment of other influenza infections, or influenza-related pathology. In this regard, the tropism of the attenuated virus can be altered to target the virus to a desired target organ, tissue or cells in vivo or ex vivo. Using this approach, the EIV-specific immune response can be induced locally, at the target site, thus avoiding or minimizing the side effects of systemic treatments. To this end, the attenuated virus can be engineered to express a ligand specific for a receptor of the target organ, tissue or cells.

Vaccine

In certain aspects, the immunological composition is useful as a vaccine, where the immunological composition induces an immune response to the antigen in a cell, tissue or mammal. Preferably, the vaccine induces a protective immune response in the mammal. As used herein, an "immunological composition" may comprise, by way of examples, a live-attenuated virus (LAV), an antigen (e.g., a polypeptide), a nucleic acid encoding an antigen (e.g., an antigen expression vector), or a cell expressing or presenting an antigen or cellular component. In particular embodiments the immunological composition comprises or encodes all or part of any polypeptide antigen described herein, or an immunologically functional equivalent thereof. In other embodiments, the immunological composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" refers to a substance that induces anti-EIV immunity or suppresses EIV upon inoculation into an animal.

The invention encompasses vaccine formulations comprising live attenuated virus (LAV), wherein the LAV is a live attenuated equine influenza virus (referred to herein as EIV LAIV). For example, in certain embodiments, the EIV LAIV is temperature-sensitive, exhibiting reduced viral replication at normal and elevated temperatures, as compared to wildtype EIV. In one embodiment, the vaccine comprises a EIV LAIV comprising one or more mutations in segment 1 and/or segment 2, and a suitable excipient. The virus used in the vaccine formulation may be selected from naturally occurring mutants or variants, mutagenized viruses or genetically engineered viruses. Attenuated strains of EIV can also be generated via reassortment techniques, or by using a combination of the reverse genetics approach and reassortment techniques. Naturally occurring variants include viruses isolated from nature as well as spontaneous occurring variants generated during virus propagation. The attenuated virus can itself be used as the active ingredient in the vaccine formulation. Alternatively, the attenuated virus can be used as the vector or "backbone" of recombinantly produced vaccines. To this end, recombinant techniques such as reverse genetics (or, for segmented viruses, combinations of the reverse genetics and reassortment techniques) may be used to engineer mutations or introduce foreign antigens into the attenuated virus used in the vaccine formulation. In this way, vaccines can be designed for immunization against strain variants, or in the alternative, against completely different infectious agents or disease antigens.

In one embodiment, the vaccine formulation comprises a plurality of mutant EIV. In one embodiment, the vaccine formulation comprises a bivalent vaccine comprising H3N8 EIV LAIV, described herein, in combination with a second LAIV, where the second LAIV is based upon the H3N8 EIV LAIV backbone but engineered to express HA and NA viral proteins of another strain. For example, in one embodiment, the first LAIV expresses HA and NA of A/equine/Ohio/1/2003 H3N8, and the second LAIV expresses HA and NA of a different clade or strain of influenza virus. In one embodiment, the first LAIV expresses HA and NA of A/equine/Ohio/1/2003 H3N8, and the second LAIV expresses HA and NA of A/equine/Richmond/1/2007 H3N8, thereby inducing an immune response against clade 1 A/equine/Ohio/1/2003 H3N8 and clade 2 A/equine/Richmond/1/2007 H3N8.

In one embodiment, the vaccine formulation may comprise one or more of the EIV LAIV, described herein, in combination with other mutant EIV that induce an anti-EIV immune response. In one embodiment, the present invention comprises a method of generating a EIV LAIV, comprising contacting a host cell with a polynucleotide comprising the nucleic acid sequences of segment 1 and/or segment 2, having one or more mutations, described elsewhere herein.

Propagation of the virus in culture is known to persons in the art. Briefly, the virus is grown in the media compositions in which the host cell is commonly cultured. Suitable host cells for the replication of EIV include, e.g., Vero cells, BHK cells, MDCK cells, 293 cells COS cells, and CEK cells, including 293T cells, COS7 cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) Culture of Animal Cells: Manual of Basic Technique, Alan R. Liss, New York; Paul (1975) Cell and Tissue Culture, 5$^{th}$ ed., Livingston, Edinburgh; Adams (1980) Laboratory Techniques in Biochemistry and Molecular Biology-Cell Culture for Biochemists, Work and Burdon (eds.) Elsevier, Amsterdam. Additional details regarding tissue culture procedures of particular interest in the production of influenza virus in vitro include, e.g., Merten et al. (1996) Production of influenza virus in cell cultures for vaccine preparation. In Cohen and Shafferman (eds) Novel Strategies in Design and Production of Vaccines, which is incorporated herein in its entirety. Additionally, variations in such procedures adapted to the present invention are readily determined through routine experimentation.

Cells for production of a virus can be cultured in serum-containing or serum free medium. In some case, e.g., for the preparation of purified viruses, it is desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Virtually any heterologous gene sequence may be constructed into the viruses of the invention for use in vaccines. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Many methods may be used to introduce the vaccine formulations described above, these include but are not limited to introduction intranasally, intratracheally, orally, intradermally, intramuscularly, intraperitoneally, intravenously, and subcutaneously. It may be preferable to introduce the virus vaccine formulation via the natural route of infection of the pathogen for which the vaccine is designed, or via the natural route of infection of the parental attenuated virus.

A vaccine of the present invention, comprising an EIV LAIV, could be administered once. Alternatively, a vaccine of the present invention, comprising an EIV LAIV, could be administered twice or three or more times with a suitable interval between doses. Alternatively, a vaccine of the present invention, comprising an EIV LAIV, could be administered as often as needed to an animal, preferably a mammal.

Methods

The invention provides a method for treating or preventing equine influenza infection or an EIV-related disease or disorder. In one embodiment, the method comprises administering an immunological composition comprising a live-attenuated virus (LAV), wherein the LAV is an EIV LAIV. In one embodiment, the method comprises administering an immunological composition comprising an EIV LAIV comprising one or more mutations in segment 1 and/or segment 2, to a subject in need thereof. In one embodiment, the method comprises administering a multivalent immunological composition comprising a plurality of LAIVs, each expressing one or more antigens of a different clade or strain of influenza virus, thereby treating or preventing and EIV-related disease or disorder associated with each clade or strain of influenza virus.

As described herein, in certain embodiments, the EIV LAIV is temperature sensitive, exhibiting decreased viral replication at normal and elevated temperatures, as compared to wildtype EIV. For example, in certain embodiments, the viral replication of EIV LAIV is 2-fold less, 3-fold less, 5-fold less, 10-fold less, 15-fold less, 20-fold less, 50-fold less, 100-fold less, 500-fold less, or 1000-fold less, than wild type EIV at normal or elevated body temperature.

In certain embodiments, the EIV LAIV induces an enhanced immune response as compared to an inactivated EIV. For example, in certain embodiments, the induced immune response of EIV LAIV is 2-fold more, 3-fold more, 5-fold more, 10-fold more, 15-fold more, 20-fold more, 50-fold more, 100-fold more, 500-fold more, or 1000-fold more, than inactivated EIV. The immune response induced the EIV LAIV can be measured using standard assays. For example, in certain embodiments, the immune response induced by EIV LAIV is measured by detecting the amount of EIV-specific antibodies produced in the subject following administration of EIV LAIV.

The therapeutic compositions of the invention may be administered prophylactically or therapeutically to subjects suffering from, or at risk of, or susceptible to, developing the disease or condition. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

In certain embodiments, the subject is a mammal. For example, the subject may include, but is not limited to, a human, primate, cow, horse, sheep, pig, dog, cat, or rodent. In one embodiment, the subject is a horse. The method may be used to treat or prevent EIV or EIV-related pathology in any breed or species of horse. In certain embodiments, the relative amount of active ingredient in a single dose, or the frequency of doses, will vary depending on the age, sex, weight, or breed of subject (e.g. horse).

The composition may be combined with an adjuvant. An adjuvant refers to a compound that enhances the immune response when administered together (or successively) with the immunological composition. Examples of suitable adjuvants include cholera toxin, *salmonella* toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

Administration

In one embodiment, the methods of the present invention comprise administering an immunological composition of the invention directly to a subject in need thereof. Administration of the composition can comprise, for example, intranasal, intramuscular, intravenous, peritoneal, subcutaneous, intradermal, as well as topical administration.

Furthermore, the actual dose and schedule can vary depending on whether the compositions are administered in combination with other pharmaceutical compositions, or depending on inter-individual differences in pharmacokinetics, drug disposition, and metabolism. One skilled in the art can easily make any necessary adjustments in accordance with the exigencies of the particular situation.

The regimen of administration may affect what constitutes an effective amount. The therapeutic formulations may be administered to the subject either prior to or after a diagnosis of infection or disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less.

Pharmaceutical Compositions

The present invention envisions treating or preventing EIV or EIV-related pathology in a mammal by the administration of a therapeutic composition of the invention to a mammal in need thereof. Administration of the composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

The present invention encompasses pharmaceutical compositions comprising an EIV LAIV to be used as anti-viral agents or as agents against EIV-related diseases and disorders. The pharmaceutical compositions have utility as an anti-viral prophylactic and may be administered to a subject at risk of getting infected or is expected to be exposed to a virus. For example, subjects traveling to parts of the world where EIV is prevalent can be administered a pharmaceutical composition of the invention. In certain embodiments, subjects who are expected to be in contact with other subjects at risk, can be administered a pharmaceutical composition of the invention.

The EIV LAIV of the invention may be engineered using the methods described herein to express proteins or peptides which would target the viruses to a particular site. In one embodiment, where the site to be targeted expresses a receptor to a growth factor, e.g., VEGF, EGF, or PDGF, the EIV LAIV may be engineered to express the appropriate growth factor or portion(s) thereof. Thus, in accordance with the invention, the EIV LAIV may be engineered to express any target gene product, including peptides, proteins, such as enzymes, hormones, growth factors, antigens or antibodies, which will function to target the virus to a site in need of anti-viral, antibacterial, anti-microbial or anti-cancer activity.

Methods of introduction include but are not limited to intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, the pharmaceutical composition is a veterinary pharmaceutical composition suitable for administration to a veterinary subject, including but not limited to an equine subject. Exemplary equine subjects include any member of genus *equus*, including but not limited to horses, zebras, asses, and donkeys.

In certain embodiments, the veterinary pharmaceutical composition is "palatable," meaning an oral veterinary composition that is readily accepted by equines, including horses, without any coaxing or with some coaxing.

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249:1527-1533).

The pharmaceutical compositions of the present invention comprise a therapeutically effective amount of the attenuated virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

The amount of the pharmaceutical composition of the invention which will be effective in the treatment or prevention of a particular disease or disorder will depend on the nature of the disease or disorder, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Development of a Novel Equine Influenza Virus Live-Attenuated Vaccine H3N8 equine influenza virus (EIV) is an important and significant respiratory pathogen of horses. EIV is enzootic in Europe and North America, mainly due to the suboptimal efficacy of current vaccines. Described herein is the generation of a temperature sensitive (ts) H3N8 EIV live-attenuated influenza vaccine (LAIV) using reverse-genetics approaches. The EIV LAIV was attenuated (att) in vivo and able to induce, upon a single intranasal administration, protection against H3N8 EIV wild-type (WT) challenge in both a mouse model and the natural host, the horse. Notably, since the EIV LAIV was generated using reverse genetics, the vaccine can be easily updated against drifting or emerging strains of EIV using the safety backbone of the EIV LAIV as master donor virus (MDV). The EIV LAIV was generated by introducing in the polymerase basic 2 (PB2) and polymerase basic 1 (PB1) viral proteins of A/equine/Ohio/1/2003 H3N8 (Florida sublineage clade 1) the mutations responsible for the ts, ca and att phenotype of A/Ann Arbor/6/60 H2N2 LAIV (Cox et al., 1988; Snyder et al., 1988), the master donor virus (MDV) of the human LAIV (FluMist, MedImmune) and assessed its safety and efficacy in both mice and horses. These results demonstrate the feasibility of implementing a novel EIV LAIV approach for the prevention and control of currently circulating H3N8 EIVs in horse populations.

The materials and methods employed in these experiments are now described.

Cells and Viruses

Human embryonic kidney 293 T cells (293T; ATCC CRL-11268), Madin-Darby canine kidney cells (MDCK; ATCC CCL-34) and equine dermal cells (E. Derm NBL-6; ATCC CCL-57) were grown in Dulbecco's modified Eagle's medium (DMEM; Mediatech, Inc.) supplemented with 10% fetal bovine serum (FBS), and 1% PSG (penicillin, 100 units/ml; streptomycin 100 µg/ml; L-glutamine, 2 mM) at 37° C. with 5% $CO_2$ (Nogales et al., 2014, J. Virol. 88, 10525-10540).

Recombinant wild-type (WT) and live attenuated (LAIV) H3N8 EIVs were generated using A/equine/Ohio/1/2003 plasmid-based reverse techniques (Martinez-Sobrido and Garcia-Sastre, 2010, J. Vis. Exp.) and grown in MDCK cells at 33° C. The commercially available A/equine/Kentucky/1/1991 H3N8 LAIV (Flu Avert I.N., Merck) was also grown in MDCK cells at 33° C. The A/equine/Kentucky/2014 H3N8, used in horse challenge experiments, was grown in embryonated hen eggs. For infections, virus preparations were diluted in phosphate buffered saline (PBS) containing 0.3% bovine albumin (BA) and 1% penicillin and streptomycin (PS) (PBS/BA/PS). After 1hour viral adsorption at room temperature (RT), MDCK cells were maintained with post-infection (p.i.) DMEM media supplemented with 0.3% BA, 1% PSG, and 1 µg/ml of N-tosyl-L-phenylalanine chloromethyl ketone (TPCK)-treated trypsin (Sigma). Viral titers were determined by immunofocus assay (fluorescent forming units, FFU/ml) in MDCK cells at 33° C. as previously described (Nogales et al., 2014, J. Virol. 88, 10525-10540) using the anti-NP monoclonal antibody (mAb) HB-65 (ATCC HB-65, HL16-L10-4R5).

Plasmids

For the generation of H3N8 EIV LAIV, the PB2 and PB1 genes of A/equine/Ohio/1/2003 H3N8 were subcloned in a pUC19 plasmid (New England BioLabs) to introduce the is mutations PB2 N265S and PB1 K391E, E581G, and A661T by site-directed mutagenesis. The presence of the introduced mutations was confirmed by sequencing. PB2- and PB1-LAIV viral segments were subcloned from pUC19 into the ambisense pDZ plasmid like the other A/equine/Ohio/1/2003 H3N8 viral genes (PB2- and PB1-WT, PA, HA, NP, NA, M and NS) for virus rescue. pDZ is an ambisense vector that contains a human RNA polymerase I promoter and a mouse terminator sequence that encodes the negative sense genomic RNA and, in opposite orientation to the polymerase I unit, contains a polymerase II transcription cassette (chicken β-actin promoter and polyA) that encode the viral proteins from the same viral gene (Chambers et al., 2009, Equine Vet. J. 41, 87-92).

Minigenome Assay

To analyze the ability of A/equine/Ohio/1/2003 H3N8 WT and LAIV polymerases to replicate and transcribe at different temperatures (33° C., 37° C., and 39° C.) E. Derm cells (12-well plate format, $5 \times 10^5$ cells/well, triplicates) were co-transfected in suspension, using Lipofectamine 2000 (Invitrogen), with 0.25 µg of each of the A/equine/Ohio/1/2003 H3N8 WT or LAIV ambisense pDZ-PB2 or PB2-LAIV, pDZ-PB1 or PB1-LAIV, pDZ-PA and pDZ-NP plasmids, together with 0.5 µg of a reporter minigenome (MG) viral (v) RNA-like expression plasmid encoding Gaussia luciferase (Gluc) driven by a murine RNA polymerase I promoter (mpPol-I Gluc), and 0.1 µg of a mammalian expression pCAGGS plasmid encoding Cypridina luciferase (Cluc) to normalize transfection efficiencies (Cheng et al., 2015; Nogales et al., 2016b). Cells transfected in the absence of the pDZ-NP plasmid were included as negative control and empty pDZ plasmid was used to keep the amount of transfected plasmid DNA constant in the negative control. At 48 h post-transfection, Gluc and Cluc expression levels were determined using the Biolux Gaussia and Cypridina Luciferase Assay kits (New England BioLabs) and quantified with a Lumicount luminometer (Packard). Reporter gene activation (Gluc) was normalized to that of Cluc and is reported as fold induction over the level of induction for the negative control (absence of NP). The mean values and standard deviations (SDs) were calculated and statistical analysis was performed using a two-tailed Student t-test with Microsoft Excel software. Data are represented as relative activity considering A/equine/Ohio/1/2003 H3N8 WT polymerase activity at each temperature as 100%.

Virus Rescue

Viral rescue of A/equine/Ohio/1/2003 H3N8 WT and LAIV was performed as previously described (Nogales et al., 2014, J. Virol. 88, 10525-10540). Briefly, co-cultures (1:1) of 293 T and MDCK cells (6-well plate format, $1 \times 10^6$ cells/well, triplicates) were co-transfected in suspension, using Lipofectamine 2000, with 1 µg of the eight-ambisense A/equine/Ohio/1/2003 H3N8 pDZ-PB2 or PB2-LAIV, -PB1 or PB1-LAIV, -PA, -HA, -NP, -NA, -M, and -NS plasmids. At 12 h post-transfection, the medium was replaced with p.i. DMEM medium supplemented with 0.5 µg/ml TPCK-treated trypsin. Tissue culture supernatants (TCS) were collected at three days post-transfection, clarified, and used to infect fresh monolayers of MDCK cells. Then, at three days p.i., recombinant viruses were plaque purified and scaled up using MDCK cells at 33° C. (Martinez-Sobrido and Garcia-Sastre, 2010, J. Vis. Exp.).

Virus Growth Kinetics

Multicycle viral growth kinetics was assessed by infecting MDCK cells (12-well plate format, $5 \times 10^5$ cells/well, triplicates) with A/equine/Ohio/1/2003 H3N8 WT and LAIV at a multiplicity of infection (MOI) of 0.001. MDCK cells were also infected with Flu Avert I.N. using an MOI of 0.001 as a control because it constitutes a is H3N8 EIV. After 1 h viral adsorption at RT, infection medium was replaced by p.i. DMEM medium supplemented with 0.5 µg/ml TPCK-treated trypsin and plates were incubated at different temperatures (33° C., 37° C. and 39° C.). TCS were collected at the indicated times p.i. and viral titers in TCS were determined by immunofocus assay (FFU/ml) in MDCK cells as indicated before (Nogales et al., 2014, J. Virol. 88, 10525-10540). The mean values and SDs were calculated using Microsoft Excel software.

Plaque Assay

Confluent monolayers of MDCK cells (6-well plate format, $1 \times 10^6$ cells/well), were infected with the indicated viruses for 1 h at RT, overlaid with agar, and incubated at 33° C., 37° C., or 39° C. At three days p.i., the cells were fixed for 1 h at RT with 4% paraformaldehyde (PFA) and the overlays were removed. Cells were then permeabilized (0.5% Triton X-100 in PBS) for 15 minutes at RT and prepared for immunostaining using the anti-NP mAb HB-65 and vector kits (Vectastain ABC vector kits and DAB HRP substrate kit; Vector) according to the manufacturer's specifications.

Mouse Experiments

Six-to-eight-week-old female C57BL/6 mice were purchased from the National Cancer Institute (NCI) and maintained under specific pathogen-free conditions. To evaluate the in vivo attenuation of EIV LAIV, six mice were anesthetized intraperitoneally (i.p.) with 2,2,2-tribromoethanol (Avertin; 240 mg/kg of body weight) and then inoculated intranasally (i.n.) with 30 µl of a virus preparation containing $10^5$ FFU of EIV WT or LAIV diluted in PBS (Rodriguez et al., 2017a). As a control, a group of mice (N=6) was also inoculated i.n. with $10^5$ FFU of Flu Avert I.N. Virus replication was determined by measuring viral titers in the lungs and nasal mucosa of infected mice at days 2 (N=3) and day 4 (N=3) p.i. To that end, mice from each group were euthanized by administration of a lethal dose of Avertin and exsanguination, and the lungs and nasal mucosa were recovered and homogenized (Rodriguez et al., 2017a). Virus titers in both tissues were determined by immunofocus assay (FFU/ml) as indicated before (Nogales et al., 2014, J. Virol. 88, 10525-10540; Rodriguez et al., 2017, J. Vis. Exp).

For the vaccination and challenge experiments, 6-8-week-old female C57BL/6 mice (N=6) were anesthetized and vaccinated i.n. with PBS or $10^3$ FFU of EIV WT, LAIV or Flu Avert I.N. (A/equine/Kentucky/1/1991 H3N8 LAIV). At fourteen days post-vaccination, mouse sera were collected by submandibular bleeding to evaluate the presence of total antibodies by enzyme-linked immunosorbent assay (ELISA) and neutralizing antibodies by hemagglutination inhibition (HAI) assay. Twenty-four hours after mice bleeding, mice were challenged i.n. with $10^5$ FFU of A/equine/Ohio/1/2003 H3N8 WT. After challenge, viral replication in mouse lungs was evaluated at days 2 (N=3) and 4 (N=3) p.i. as described above (Rodriguez et al., 2017, J. Vis. Exp).

Horse Experiments

Male and female one-to-two-year-old horses of mixed breed (mainly Standardbred-quarter horse crosses) were used. Horses were raised as part of a closed herd, and had not been previously vaccinated for EIV. All horses were seronegative for EIV H3N8, as measured by hemagglutination inhibition assay (HAI) prior to the start of the study (data not shown). To evaluate the in vivo attenuation of A/equine/Ohio/1/2003 H3N8 LAIV, horses (N=4) were inoculated by i.n. intubation with 2 ml of a virus preparation containing $4×10^8$ FFU of A/equine/Ohio/1/2003 H3N8 LAIV diluted in PBS. This dose, the maximum available and similar to that used in the pilot studies of the Flu Avert I.N. LAIV by Heska Corp. (Wilson and Robinson, 2000, J. Equine Vet. Sci. 20, 8-10), was chosen so as to provide the greatest likelihood of revealing any clinical signs induced by the LAIV. Viral attenuation was tested daily by the observation of clinical signs, measurement of rectal temperatures and by determining the presence of virus in nasopharyngeal swabs that were taken prior to vaccination (day 0) and daily for three days thereafter. The presence of virus in nasal swabs was determined by quantitative (q)RT-PCR as described before (Lu et al., 2009, J. Clin. Microbiol. 47, 3907-3913).

For the vaccination and challenge experiments, one-to-two years-old horses (N=4) were vaccinated by i.n. inoculation with 2 ml of a virus preparation containing $4×10^8$ FFU of A/equine/Ohio/1/2003 H3N8 LAIV. Another group of horses (N=2) were used as a control (unvaccinated). To avoid exposure of control horses to shed EIV LAIV, the latter were pastured separately. At 27 days post-vaccination, all horses (N=6) were brought into a BSL-2 isolation barn. The challenge virus, a heterologous Florida clade 1 EIV strain, A/equine/Kentucky/2014 H3N8, was aerosolized using a DeVillbis Ultra-Neb 99 nebulizer, and pumped into a tented stall (37.5 $m^3$) to a density of $1×10^7$ 50% egg infectious dose ($EID_{50}$) units per $m^3$, where it was inhaled by the horses for 45 minutes (Mumford et al., 1990, Equine Vet. J. 22, 93-98; Townsend et al., 2001, Equine Vet. J. 33, 637-643). The challenge dose of virus was similar to that used in previous experimental infection of horses (Lunn et al., 2001, J. Am. Vet. Med. Assoc. 218, 900-906). Horses were observed daily thereafter and rectal temperatures, clinical signs, and nasopharyngeal swabs were taken prior to viral challenge (day 0) and daily for seven days. qRT-PCR was performed on each nasopharyngeal swab as described above, and non-quantitative virus detection was also done on each swab by injection into embryonated eggs as described before (Chambers et al., 2001, Equine Vet. J. 33, 630-636). Infectious virus content of the nasopharyngeal swab samples from day 2 and day 3 post-challenge was determined by $EID_{50}$ titration.

ELISA

For the evaluation of the virus-specific antibodies levels present in the sera of vaccinated mice, ELISAs were performed as previously described (Nogales et al., 2016, J. Virol., 90: 6291-6302; Nogales et al., 2017, Virology, 500, 1-10; Nogales et al., 2016, J. Viol, 91; Rodriguez et al., 2017, J. Vis. Exp.; Rodriguez et al., 2017, Virology, 504, 96-106). Briefly, 96-well plates were coated with cell lysates from mock- or EIV-infected MDCK cells and incubated overnight (O/N) at 4° C. Animal sera were assayed as two-fold dilutions (starting dilution of 1:100) and titers determined as described previously.

HAI Assay

To evaluate the presence of EIV neutralizing antibodies, mouse sera were treated with receptor-destroying enzyme (RDE; Denka Seiken) for 16 h at 37° C. and heat inactivated for 30 min at 56° C. The sera were then serially 2-fold diluted (starting dilution of 1:50) in 96-well V-bottom plates and mixed 1:1 with 4 hemagglutinating units (HAU) of A/equine/Ohio/1/2003 H3N8 during 30 min at RT. The HAI titers were determined by adding 0.5% turkey red blood cells to the virus-antibody mixtures for 30 min on ice (Nogales et al., 2016b). The geometric mean titers and SDs from individual mice (N=6) were calculated from the last well where hemagglutination was inhibited. HAI for equine sera was performed in essentially the same manner except that equine sera were pre-treated with trypsin-periodate as described (Chambers and Reedy, 2014, Methods Mol. Biol. 1161, 411-422) to remove non-specific inhibitors of hemagglutination, and chicken red blood cells were used.

The results of the experiments are now described.

Generation and Characterization of A/Equine/Ohio/1/2003 H3N8 (EIV) LAIV

The commercially available EIV LAIV (Flu Avert I.N.) is made of an EIV strain that circulated over 25 years ago (A/equine/Kentucky/1/1991 H3N8) and has never been updated (Youngner et al., 2001, Am. J. Vet. Res. 62, 1290-1294). In order to generate an updated EIV LAIV, four of the five mutations responsible for the ts, ca and att phenotypes of the human A/Ann Arbor/6/60 H2N2 LAIV (FluMist) (Cox et al., 1988; Snyder et al., 1988) were introduced into the PB2 (N265S) and PB1 (K391E, E581G, A661T) genes of A/equine/Ohio/1/2003 H3N8 (EIV) (FIG. 1A), a clade 1 Florida sublineage strain recommended by the OIE to be included in the EIV vaccine (Paillot et al., 2016, Pathogens, 5). The A/equine/Ohio/1/2003 H3N8 NP viral segment already contains a Gin position 43. A minigenome replication assay was then performed in E. Derm cells at different temperatures (33° C., 37° C. or 39° C.) to analyze if the mutations introduced into the PB2 and PB1 genes of A/equine/Ohio/1/2003 H3N8 conferred a ts phenotype to the viral polymerase complex. At 33° C., both A/equine/Ohio/1/2003 H3N8 WT and LAIV polymerases induced similar levels of Gluc expression (FIG. 1B). However, Gluc expression was significantly reduced at 37° C. and even more at 39° C. (FIG. 1B).

Based on the ts phenotype observed in the minigenome assay (FIG. 1), it was next assessed if the introduced mutations in the viral PB2 and PB1 polymerase subunit of A/equine/Ohio/1/2003 H3N8 would result in a virus with impaired growth kinetics at restrictive (37-39° C.) but not at permissive (33° C.) temperatures. Thus, WT and LAIV A/equine/Ohio/1/2003 H3N8 (referred to henceforth as EIV WT and EIV LAIV, respectively) were rescued using previously described reverse-genetic techniques (Martinez-Sobrido and Garcia-Sastre, 2010, J. Vis. Exp.; Nogales et al., 2014, J. Virol. 88, 10525-10540). The viral replication kinetics of both viruses were determined by evaluating viral titers in MDCK cells infected at low (0.001) multiplicity of infection (MOI) at different temperatures (33° C., 37° C. or 39° C.) (FIG. 2A). Flu Avert I.N. was also included as a control. At 33° C., both EIV WT and LAIV, and Flu Avert I.N., grew with similar kinetics and reached peak titers at 48 h p.i. At 37° C. and 39° C., EIV WT replication was similar to that observed at 33° C. The titers of EIV LAIV and Flu Avert I.N. were significantly reduced or not detected at 37° C. and 39° C., respectively, as compared to EIV WT (FIG. 2A). The plaque phenotype of EIV WT and LAIV, and Flu Avert I.N. were also analyzed at the same temperatures (33° C., 37° C. or 39° C.) (FIG. 2B). EIV WT plaque size was similar at 33° C. and 37° C., and slightly reduced at 39° C. in accordance with the minimal reduction in viral titers observed in the kinetics at that temperature (FIG. 2A). In the case of EIV LAIV and Flu Avert I.N., the size of the plaques at 33° C. was similar to that of EIV WT, but at high temperatures, the plaque size was strongly reduced (37° C.) or plaques were not detected (39° C.), corroborating the growth kinetic results (FIG. 2A). Altogether, these results demonstrate that amino acid substitutions in the PB2 and PB1 polymerase subunits of A/equine/Ohio/1/2003 H3N8 confer a is phenotype.

Attenuation of EIV LAIV in Mice

Figure 2:
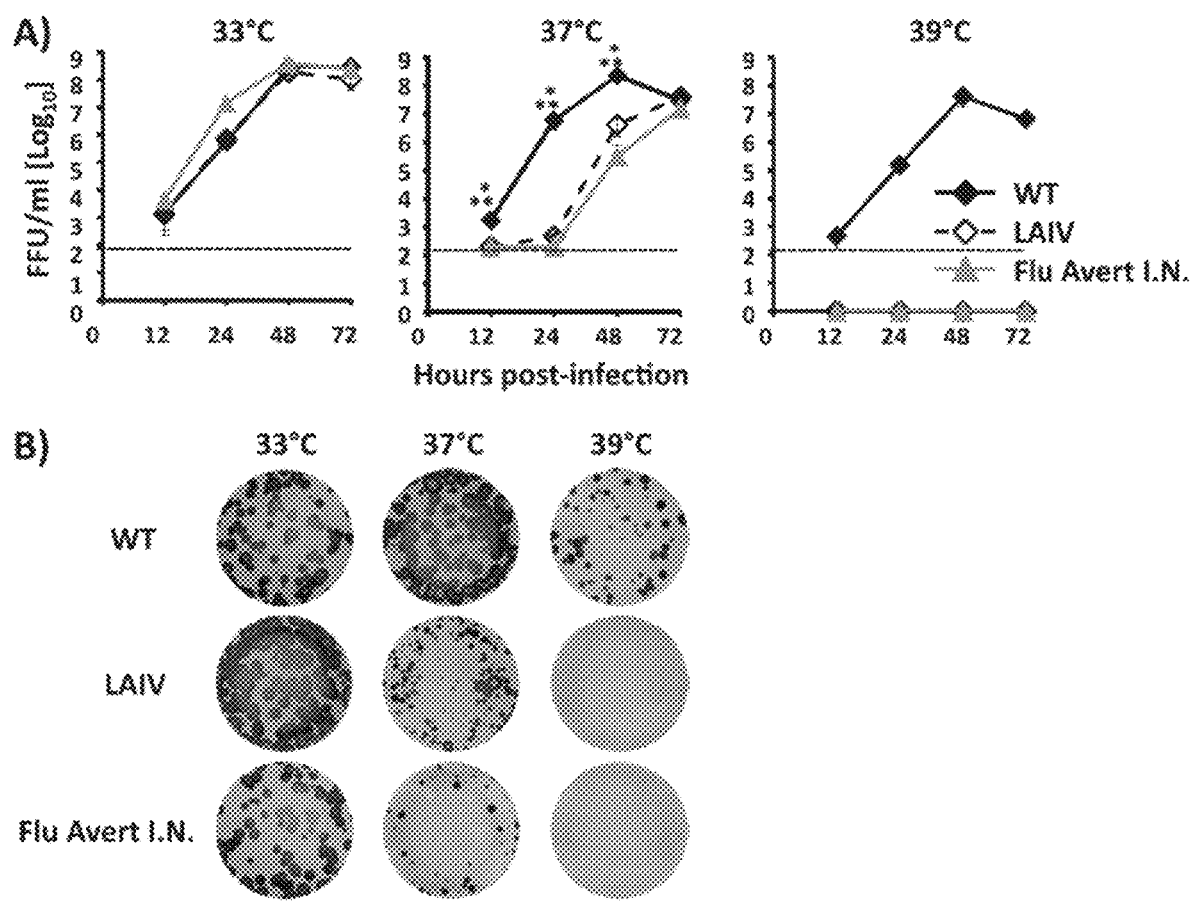
FIG. 2, comprising
Figure 3:
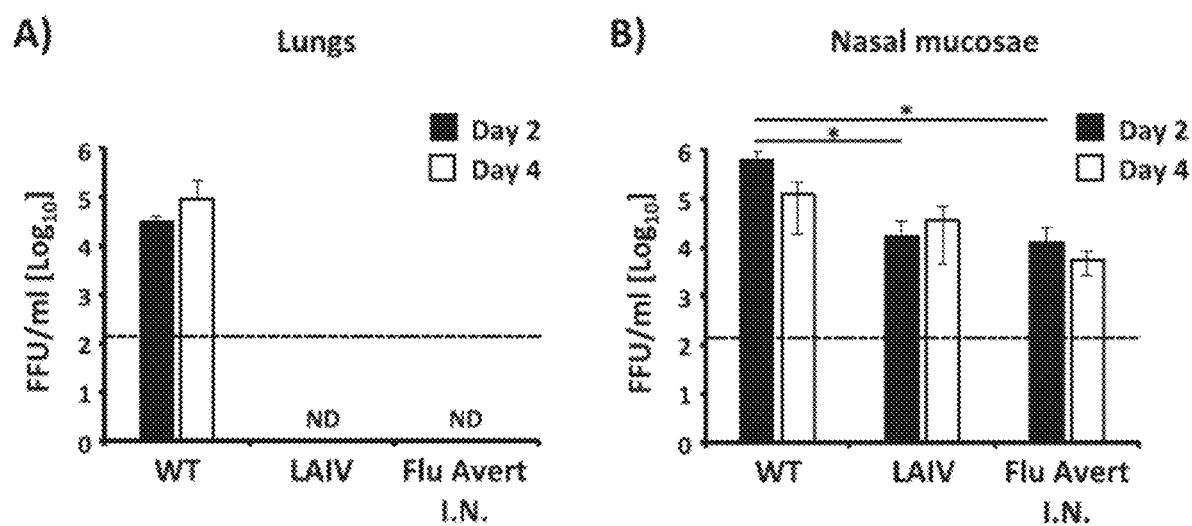
FIG. 3, comprising

After elucidating that the growth kinetics (FIG. 2A) and the plaque size (FIG. 2B) of EIV LAIV were affected at high temperatures (37° C. and 39° C.) but not at low temperatures (33° C.), its ability to replicate in vivo in a mouse model of influenza infection was analyzed (FIG. 3). To that end, mice (N=3/time point) were infected i.n. with $10^5$ FFU of EIV WT or LAIV. Mice were also infected with $10^5$ FFU of Flu Avert I.N. as an internal control. Since no signs of infection were detected in mice after infection with EIV WT, replication of EIV WT and LAIVs were determined by evaluating viral titers from the lungs (FIG. 3A) and nasal mucosa (FIG. 3B) at days 2 and 4 p.i. It was decided to use this high dose ($10^5$ FFU) to better evaluate the safety profile of the new EIV LAIV in comparison with its WT counterpart. Notably, viral titers were only detected in the lungs of mice infected with EIV WT at both times p.i. (FIG. 3A), but no virus was detected in the lungs of mice infected with EIV LAIV or Flu Avert I.N. (FIG. 3A). On the other hand, viral replication was detected in the nasal mucosa of mice infected with the three viruses (FIG. 3B), although the viral titers obtained in mice infected with EIV LAIV and Flu Avert I.N. were significantly lower at both times p.i. as compared to EIV WT. These results indicate that the EIV LAIV was also attenuated in vivo at high temperatures (lungs) but able to replicate in the nasal mucosa where the temperature is lower. Importantly, the same in vivo is phenotype was observed with Flu Avert I.N.

Mice Immunized with EIV LAIV are Protected Against H3N8 EIV WT Challenge

Figure 4:
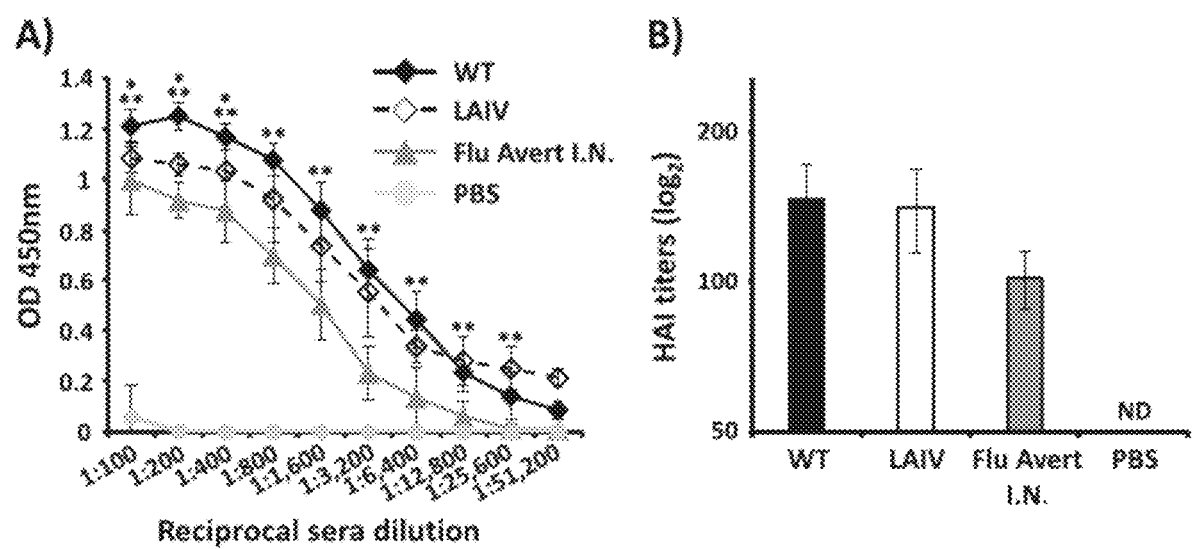
FIG. 4, comprising

To evaluate the immunity induced by EIV LAIV, groups of mice (N=6) were vaccinated i.n. with $10^3$ FFU of WT and LAIV EIVs, mock vaccinated with PBS or vaccinated i.n. with $10^3$ FFU of Flu Avert I.N. as negative and positive controls, respectively. The $10^3$ FFU/mouse dose was chosen because based on the safety results (FIG. 3). Further, it is previous studies related to the development of LAIVs against H3N8 (Nogales et al., 2016, J. Virol. 91) and H3N2 (Rodriguez et al., 2017, Virology 504, 96-106) CIVs, this dose induced strong humoral and cellular responses, as well as complete protection against challenge with WT CIVs. Humoral immune responses were evaluated in mouse sera collected 14 days post-vaccination. Antibody responses against total EIV proteins were evaluated by ELISA musing cell extracts from virus-infected MDCK cells (FIG. 4A) (Nogales et al., 2016, J. Virol. 91; Rodriguez et al., 2017, Virology 504, 96-106). Sera from mice vaccinated with EIV LAIV elicited high serum IgG titers against EIV proteins, close to those obtained in the sera from mice infected with EIV WT, while a significant lower titer of antibodies was observed in the sera from mice immunized with Flu Avert I.N. (FIG. 4A). Additionally, HAI assays were performed to evaluate the presence of neutralizing antibodies in sera from vaccinated mice (FIG. 4B). HAI titers against EIV were higher in the sera from mice vaccinated with EIV LAIV than those observed in mice vaccinated with Flu Avert I.N and were similar to those obtained in EIV WT infected mice (FIG. 4B).

Figure 5:
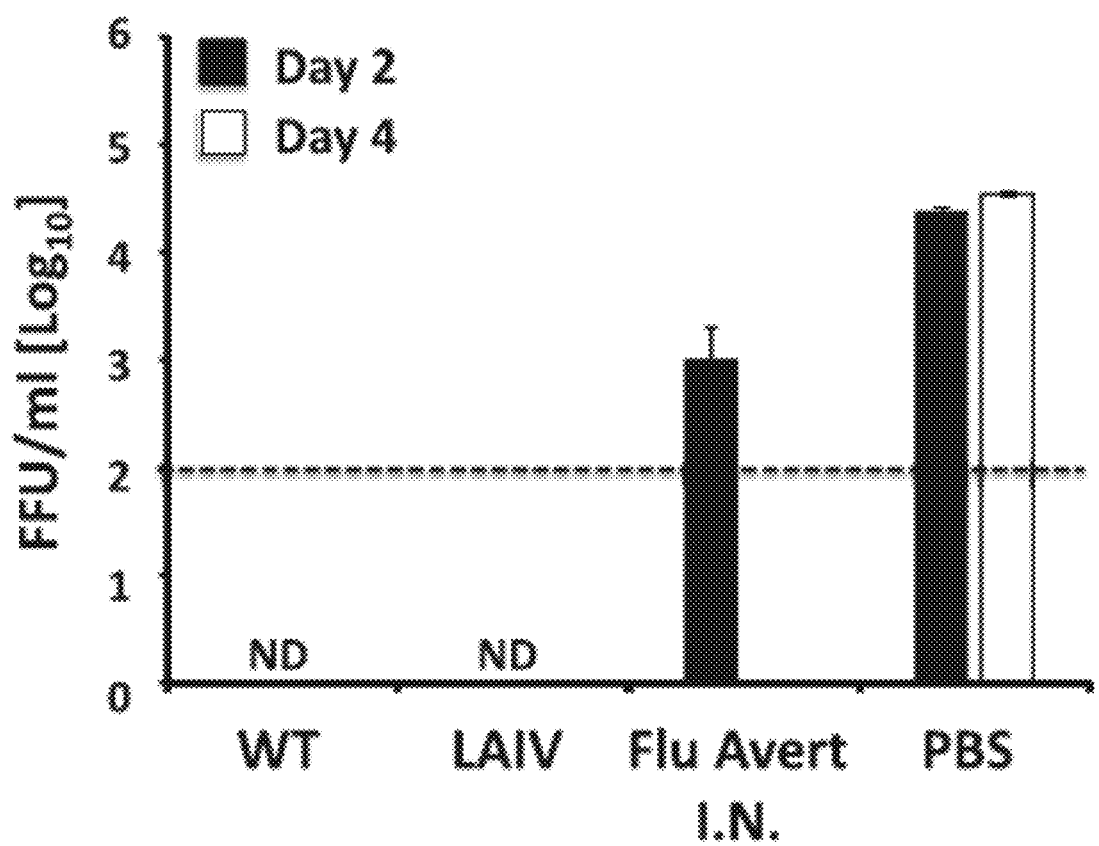
FIG. 5 depicts the results of example experiments demonstrating the protection of EIV LAIV against EIV challenge in mice: Female 6- to-8-week-old C57BL/6mice (N=6) were vaccinated with $1 \times 10^3$ FFU of A/equine/Ohio/1/2003 H3N8 WT or LAIV. Mice were also mock (PBS) vaccinated or vaccinated (i.n.) with $1 \times 10^3$ FFU of Flu Avert I.N. as negative and positive controls, respectively. At 15 days post-vaccination, mice were challenged with $1 \times 10^5$ FFU of A/equine/Ohio/1/2003 H3N8 WT and viral titers at days 2 (N=3) and 4 (N=4) post-challenge were evaluated from lung homogenates by immunofocus assay (FFU/ml) using an anti-NP mAb (HB-65). Dotted black line indicates the limit of detection (200 FFU/ml). Data represent the means±SDs. ND, not detected.

Next, experiments were performed to evaluate the protection efficacy induced by the EIV LAIV against homologous A/equine/Ohio/1/2003 H3N8 WT challenge (FIG. 5). Mice (N=6) were vaccinated i.n. with $10^3$ FFU of WT and LAIV EIVs, Flu Avert I.N., or mock vaccinated with PBS. Fifteen days after vaccination, mice were challenged with $10^5$ FFU of A/equine/Ohio/1/2003 H3N8 WT and viral titers in the lungs of infected mice (N=3/group) were determined 2 and 4 days after challenge (FIG. 5). Mock-vaccinated (PBS) mice exhibited lung viral titers of ~$3\times10^4$ FFU/ml at days 2 and 4 post-challenge, whereas mice vaccinated with WT or LAIV EIVs showed no detectable virus in the lungs at those times (FIG. 5). Contrarily, A/equine/Ohio/1/2003 H3N8 WT was detected in the lungs of mice vaccinated with Flu Avert I.N. at day 2 post-challenge (~$1\times10^3$ FFU/ml), but not at day 4 post-challenge (FIG. 5). These results indicate that the EIV LAIV induced better protection than Flu Avert I.N. against a challenge with A/equine/Ohio/1/2003 H3N8 WT in mice, probably because of the antigenic match.

Attenuation of EIV LAIV in Horses

Figure 6:
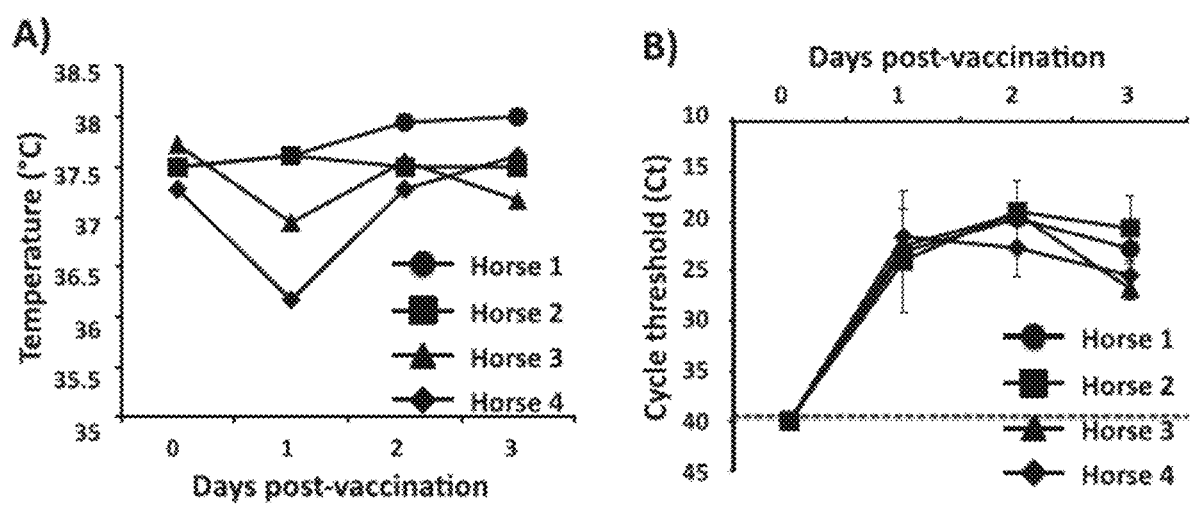
FIG. 6, comprising
Figure 7:
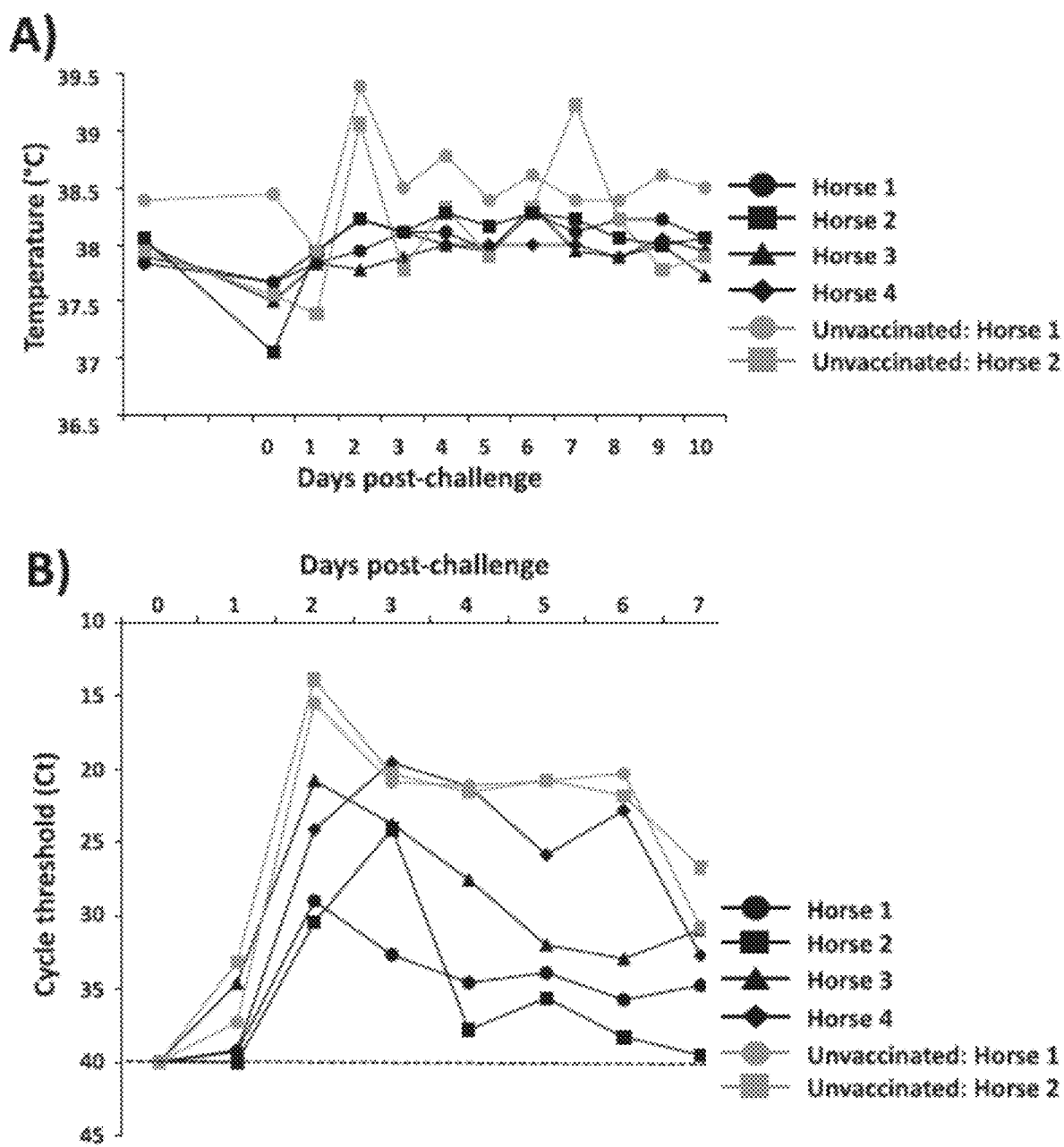
FIG. 7, comprising

The safety and the protection efficacy induced by the EIV LAIV was next evaluated in horses, its natural host. To this end, four horses were infected i.n. with $4\times10^8$ FFU of EIV LAIV and monitored for clinical signs such as cough, nasal discharge, respiration and depression, rectal temperature as well as viral shedding during the first 3 days after infection (FIG. 6). None of the horses showed significant adverse effects. Three of the four horses showed a slight, bilateral serous nasal discharge at days 2 and 3 p.i. and a single incidence of coughing was observed, however rectal temperatures remained normal (37.5° C.±0.2 on day of vaccination, 37.6° C.±0.4 on Day+3) (FIG. 6A). To measure the presence of EIV LAIV in nasopharyngeal swabs collected at days 0-3 p.i., a qRT-PCR was performed on each swab (one swab for each nostril of each horse per day). Virus shedding was detected in all nasopharyngeal swabs collected on days 1-3 p.i. showing a peak at day 2 p.i. (FIG. 6B), indicative of viral replication. The horses were observed daily for an additional 25 days although further swabbing past day 3 p.i. to ascertain the duration of shedding was not done. During that period, one horse was euthanized for an unrelated problem (equine protozoal myelitis). Similar safety observations, including slight serous nasal discharge in 2/4 horses, were obtained from the yearling horses that were subsequently challenged (FIG. 7). Following vaccination, all horses showed seroconversion as their HAI antibody titers increased from undetected (<10) to 20 (in three horses of both the safety and challenge trials) or 10 (in the 4th horse of both trials) and, as expected, no HAI antibodies were detected in the sera from the unvaccinated control group. These results demonstrate the safety profile of the EIV LAIV in horses and their ability to replicate in the upper respiratory track, necessary for the induction of immunity, including HA-specific antibody responses.

Horses Immunized with EIV LAIV are Protected Against Challenge with Heterologous EIV H3N8 WT In order to evaluate the protection efficacy induced by the EIV LAIV in its natural host, a group of horses (N=4) was vaccinated as previously indicated with $4\times10^8$ FFU of EIV LAIV, or mock vaccinated (N=2), as negative control (FIG. 7). Twenty-seven days after vaccination, horses were challenged by exposure to aerosolized wild-type virus ($1\times10^7$ $EID_{50}$ units per $m^3$ of A/equine/Kentucky/2014 H3N8 WT into a tented stall (37.5 $m^3$)) for 45 min. A/equine/Kentucky/14 (H3N8) virus, a Florida clade 1 strain is heterologous yet antigenically similar to the EIV LAIV. During the first 10 days after challenge, horses were monitored for rectal temperatures (FIG. 7A), presence of clinical symptoms of infection (cough, nasal discharge, respiration, depression and swelling of lymph nodes) and virus shedding (FIG. 7B). Both unvaccinated controls, but none of the four horses vaccinated with EIV LAIV exhibited a characteristic spike of pyrexia on day two post-challenge (FIG. 7A), and also one of the unvaccinated horses (number 2) was noted as lethargic on day two post-challenge. Body temperatures of the two control horses returned to normal or near-normal range on days three to six post-challenge, but the unvaccinated horse number 2 had a second fever spike on day seven post-challenge (FIG. 7A). Both unvaccinated horses had cough on days three (horse number 2) and seven (horse number 1) different days post-challenge, while coughing was not observed in any of the vaccinates. Nasal discharge was observed in both control animals on day eight (unvaccinated horse 1) or day two (unvaccinated horse 2) post-challenge. Notably, none of the vaccinated horses had cough or nasal discharge. Another clinical symptom observed in the unvaccinated horses was inspiratory wheeze on day six (unvaccinated horse 1) and day four (unvaccinated horse 2) post-challenge, but not in the vaccinated horses. Swelling of submandibular or parotid lymph nodes was observed in three out of four vaccinates as well as both controls; however, the severity and duration were greater in the controls. Late in the study (at day 11 post-challenge) an independent veterinary assessment led to both control horses, but none of the vaccinates, being treated with antibiotics to promote full recovery. From a clinical standpoint, therefore, vaccinated horses appeared to be protected from challenge with wild-type EIV.

A/equine/Kentucky/2014 H3N8 WT virus shedding in nasopharyngeal swabs was evaluated by inoculation of embryonated chicken eggs and also by direct qRT-PCR (FIG. 7B). When the nasopharyngeal swabs from vaccinated horses were inoculated in eggs, live virus was detectable at least one time post-challenge, with an average of 2.25 days up to maximum of five days post-challenge. $EID_{50}$ titrations of infectious virus content in the swab material collected at day two or three post-challenge showed titers between $1.7 \times 10^2$ and $3.16 \times 10^3$ $EID_{50}$ units/ml. On the other side, both unvaccinated horses shed detectable live virus for five and six days post-challenge, and viral titers in the allantoic fluid at two days post-inoculation were $1.7 \times 10^5$ (number 2) and $4.6 \times 10^7$ (number 1) $EID_{50}$ units/ml. Thus, the EIV LAIV did not achieve sterilizing immunity against an heterologous challenge after a single dose, but live virus shedding appeared to be reduced by at least three orders of magnitude comparing with the unvaccinated horses. These results were confirmed when the presence of virus by qRT-PCR in the daily nasopharyngeal swabs was evaluated (FIG. 7B). In both horses' groups (vaccinated or unvaccinated) there was detectable virus amplification continuously from day one post-challenge (or day two for the vaccinated horse 2) through day seven when swabbing was discontinued. The peaks shedding in unvaccinated horses were greater than the values obtained in vaccinated horses with a difference between 5 and 15 cycles suggesting about 500 to 1500 times greater target concentration than in vaccinated horses. By 14 days following viral challenge, all horses exhibited 16-32-fold increases in serum HAI antibody titers. Altogether, the results show that the EIV LAIV induced protection against a heterologous challenge whit A/equine/Kentucky/2014 H3N8 WT.

H3N8 EIV LAIV

Described herein is the development of a more effective LAIV for the prevention and control of equine influenza using reverse genetics. This is the first time than an i.n. competitive is LAIV based on reverse genetic techniques has been developed for the prevention and control of H3N8 EIV in horses. To generate the H3N8 EIV LAIV, the mutations responsible for the ca, ts and att phenotypes of the human MDV A/Ann Arbor/6/60 H2N2 LAIV (Cox et al., 1988, Virology 167, 554-567; Snyder et al., 1988, J. Virol. 62, 488-495) were introduced in the PB2 and PB1 viral genes from A/equine/Ohio/1/2003 H3N8, a strain recommended by the OIE to be part of EIV vaccines (clade 1 of Florida sublineage) (OIE, 2017) (FIG. 1). In vitro, the recombinant A/equine/Ohio/1/2003 H3N8 LAIV (EIV LAIV) replicated efficiently at low temperature (33° C.), which is important for vaccine production, but was restricted in replication at higher (37° C. and 39° C.) temperatures, imperative for its safe implementation as LAIV (FIG. 2). In a mouse model of influenza infection, the EIV LAIV was attenuated in the lower respiratory tract (lungs) but not in the upper respiratory tract (nasal mucosa) when compared to its WT counterpart (FIG. 3). Importantly, the phenotype observed with the EIV LAIV in vivo and in vitro was the same as that observed with the currently available H3N8 EIV LAIV, Flu Avert I.N. Notably, the EIV LAIV was able to induce, upon a single i.n. immunization dose, complete protection against challenge with A/equine/Ohio/1/2003 H3N8 WT, contrary to Flu Avert I.N. that only showed partial protection (FIG. 5). This partial protection observed with Flu Avert I.N. is probably due to the fact that Flu Avert I.N. is based on a virus that is antigenically distant from current EIV circulating strains, including that used in the present study (A/equine/Ohio/1/2003). The analysis of humoral responses showed that the titer of total (FIG. 4A), as well as neutralizing (FIG. 4B), antibodies against A/equine/Ohio/1/2003 H3N8 WT was higher in sera from mice immunized with the EIV LAIV than in sera from mice vaccinated with Flu Avert I.N. In horses, its natural host, the EIV LAIV was safe since horses did not develop any symptoms of infection including fever (FIG. 6A), and was able to replicate in the upper respiratory track since the virus was detected in nasal swabs (FIG. 6B), where the temperatures is low, which is essential to induce mucosal immunity. Serum antibody titers in horses following vaccination were low, which was also reported with the Flu Avert I.N. LAIV in horses following a single dose (Lunn et al., 2001, J. Am. Vet. Med. Assoc. 218, 900-906; Townsend et al., 2001, Equine Vet. J. 33, 637-643). Those authors argued that other indices of immunological response, such as local mucosal immunity, appear to be more relevant than serum antibody levels (Lunn et al., 2001, J. Am. Vet. Med. Assoc. 218, 900-906; Townsend et al., 2001, Equine Vet. J. 33, 637-643). Importantly, in the horse vaccination and challenge experiment with the heterologous A/equine/Kentucky/2014 H3N8 WT virus (Florida clade 1 strain), none of the horses vaccinated with the EIV LAIV showed clinical symptoms of infection after challenge, with the exception of swelling of submandibular or parotid lymph nodes but with a lower severity and duration than the observed in unvaccinated horses. It is true than in all horses (vaccinated or unvaccinated) the challenged A/equine/Kentucky/2014 H3N8 WT virus was detected in nasopharyngeal swabs by qRT-PCR (FIG. 7B) and by growth in embryonated chicken eggs, but in both systems the virus detected was three orders of magnitude lower in vaccinated horses. All these results indicate that the EIV LAIV induces protection against a A/equine/Kentucky/2014 H3N8 WT heterologous challenge.

Compared to current H3N8 EIV IIVs, the H3N8 EIV LAIV approach presents several advantages. First, the H3N8 EIV LAIV is administered intranasally and mimics the natural route of viral infection, therefore inducing mucosal immune responses at the site of infection (Kohlmeier and Woodland, 2009, Annu Rev. Immunol. 27, 61-82; Murphy and Coelingh, 2002, Viral Immunol. 15, 295-323). Second, a significantly lower amount of virus in the H3N8 EIV LAIV is required to induce superior protection than that required with H3N8 EIV IIVs (Nogales et al., 2016, J. Virol. 91; Rodriguez et al., 2017, Virology 504, 96-106). Third, LAIVs have been shown to stimulate more robust systemic humoral response (Cheng et al., 2013, J. Infect. Dis. 208, 594-602; De Villiers et al., 2009, Vaccine 28, 228-234; Katsura et al., 2012, Vaccine 30, 6027-6033; Nogales et al., 2016, J. Virol. 91; Rodriguez et al., 2017, Virology 504, 96-106; Victor et al., 2012, J. Virol) and elicit cellular immunity (Cheng et al., 2013, J. Infect. Dis. 208, 594-602; Katsura et al., 2012, Vaccine 30, 6027-6033), leading to recruitment of influenza-specific CD8 T cells in the target tissues of the respiratory tract (Baker et al., 2013, J. Virol. 87, 8591-8605; Guo et al., 2014, J. Virol. 88, 12006-12016; Katsura et al., 2012, Vaccine 30, 6027-6033; Nogales et al., 2016, J. Virol. 91; Powell et al., 2012, J. Virol. 86, 13397-13406; Rodriguez et al., 2017; Uraki et al., 2013, J. Virol. 87, 7874-7881). Fourth, a single immunization with the H3N8 EIV LAIV would be sufficient to confer at least partial protection against H3N8 EIV WT in a shorter period of time, compared with the multiple doses required with the current inactivated vaccines. Finally, the H3N8 EIV LAIV would provide better cross protection against antigenically distinct H3N8 EIV strains than that provided by EIV IIVs, diminishing the chance of EIV outbreaks. Some of the above advantages are shared by the only commercially available H3N8 EIV LAIV, Flu Avert I.N. (Chambers et al., 2001, Equine Vet. J. 33, 630-636). However, the present technology also offers a number of additional advantages. First, the mutations introduced in the PB2 and PB1 polymerase subunits of A/equine/Ohio/1/2003 H3N8 have been previously described to be responsible for the ts, ca and att phenotype in the MDV of the human A/Ann Arbor/6/60 H2N2 LAIV (FluMist) (Cox et al., 1988, Virology 167, 554-567; Snyder et al., 1988, J. Virol. 62, 488-495) which have a proven history of safety, immunogenicity and protection efficacy not only against human viruses, but also against avian and equine influenza viruses (Baz et al., 2015, J. Virol. 89, 1652-1659; Suguitan et al., 2006, PLoS Med. 3, e360). Second, same ts and ca mutations were also introduced in other influenza A viruses inducing the same attenuated phenotype (Cox et al., 2015, J. Virol. 89, 3421-3426; Jin et al., 2004, J. Virol. 78, 995-998; Nogales et al., 2016, J. Virol. 91; Rodriguez et al., 2017, Virology 504, 96-106; Zhou et al., 2012, Vaccine 30, 3691-3702). Third, the use of state-of-the-art reverse genetic techniques will facilitate, similar to the case of the human LAIV, the fast and accurate development of LAIV candidates for the control of currently circulating clades 1 and 2 strains of the Florida sublineage, or newly introduced EIV strains in the case of a new outbreak in the horse population. To that end, the temperature sensitive A/equine/Ohio/1/2003 H3N8 LAIV could be used as a MDV to produce updated LAIV by the introduction of HA and NA from antigenically different circulating H3N8 EIV strains or newly introduced EIVs in the horse population, including EIVs with panzootic potential.

Example 2: Development of Bivalent and/or Multivalent EIV LAIVs

The LAIV approach described in Example 1 was utilized to develop a bivalent H3N8 EIV LAIV. Ohio/03 LAIV was used as master donor virus (MDV) to generate a recombinant clade 2 A/Equine/1/2007 H3N8 LAIV (Rich/07 LAIV). A virus containing the six internal genes (PB2, PB1, PA, NP, M and NS) from Ohio/03 LAIV, and the HA and NA genes of A/Equine/1/2007 H3N8 WT (Rich/07 WT) was generated. This bivalent EIV LAIV is made up of blended clade 1 Ohio/03 and clade Rich/07 monovalent LAIVs. Proper construction of the Rich/07 recombinant virus was confirmed by extraction of total RNA; followed by PCR amplification of the HA and NA genes; restriction endonuclease digestion and agarose gel separation of PCR products, and sequencing (data not shown). The two viruses in the bivalent EIV LAIV were characterized individually in vitro by assessing growth kinetics in MDCK cells as well as by plaque assays using an anti-NP antibody (data not shown). This bivalent LAIV follows the current OIE recommendations of including representative strains of the clades 1 and 2 of Florida sublineages of H3N8 EIVs.

Based on the multiple advantages over H3N8 EIV IIVs, this novel platform represents an easier and faster approach for the feasibility of implementing a safe and more effective LAIV for the prevention and control of H3N8 EIVs in the equine population, reducing the burden of current and future influenza disease in horses.

Currently, there are two clades (1 and 2) of the Florida sublineage of EIV circulating in horses and the OIE recommends including both clades in EIV vaccines. Examples of EIV strains to be included in the vaccine as currently recommended by the OIE include the Florida clade 2 strain Newmarket/2003-like and the Florida clade 1 strains South Africa/03-like, Ohio/03-like and Nottinghamshire/09-like, and the Florida clade 2 strains Richmond/07-like, Lancashire/10-like or Hants/10-like. To generate a bivalent EIV LAIV, the safety backbone of the A/equine/Ohio/1/2003 H3N8 (EIV) LAIV as a master donor virus (MDV) and the hemagglutinin (HA) and Neuraminidase (NA) of the other EIV strain was used. To that end, reverse genetic approaches employing the internal genes of A/equine/Ohio/1/2003 H3N8 (EIV) LAIV (PB2, PB1, PA, NP, M and NS) and the surface glycoproteins genes (HA and NA) of the other EIV strain, were utilized. Reverse genetic and experimental approaches to generate LAIVs against other EIV strains are similar to the methods described in Example 1 for the generation of A/equine/Ohio/1/2003 H3N8 LAIV. The EIV clade 1 LAIV is combined with the EIV clade 2 LAIV in a blended bivalent EIV LAIV. Multivalent EIV LAIVs can also be developed using the same experimental approach as described for the bivalent LAIV, where the A/equine/Ohio/1/2003 H3N8 (EIV) LAIV is used as a MDV to express HA and NA of other EIV strains.

Example 3: Evaluation of a Clade 1 and Clade 2 Bivalent EIV LAIV Vaccine in Horses One-to-two years-old influenza-seronegative horses of both sexes were mock-vaccinated (N=6) or vaccinated (N=12) with a EIV bivalent LAIV vaccine ($3 \times 10^8$ FFU of each A/equine/Ohio/1/2003 [Clade 1] and A/equine/Richmond/1/2007 [Clade 2] LAIV) using a prime-boost regimen with the second dose given 29 days after the first. The A/equine/Richmond/1/2007 [Clade 2] LAIV was based upon using the temperature-sensitive A/equine/Ohio/1/2003 LAIV as a master donor virus, where the A/equine/Richmond/1/2007 [Clade 2] LAIV comprises the temperature-sensitive A/equine/Ohio/1/2003 backbone but modified to express A/equine/Richmond/1/2007 HA and NA, as described above. Two additional seronegative sentinel horses were added after the first vaccinations. Individual rectal temperature and viral shedding were measured in each horse before and the following 3 days after each vaccination. Fifty-six days post-vaccination (prime), sera samples were collected, and presence of hemagglutinating and neutralizing antibodies (Ab) was assessed by HAI and microneutralization assays, respectively. Fifty-seven days post-vaccination (prime), vaccinated (N=12), mock-vaccinated (N=6), and sentinel (N=2) horses were challenged with either $1\times10^7$ EID$_{50}$ of Richmond/2007 WT (Rich/07 WT; N=6 vaccinated/N=3 mock-vaccinated) or Kentucky/2014 H3N8 WT (KY/14 WT [Clade 1]; N=6 vaccinated/N=3 mock-vaccinated/N=2 sentinel) to assess protection against clade 1 and 2 EIV, respectively. During 8 days after challenge, rectal temperatures and virus shedding were evaluated. All vaccinations and all challenge inoculations were performed on horses individually by using the Flexi-Neb II nebulizer/nose mask.

For the Clade 2 challenge, the 6 vaccinates showed a mild temperature increase for 1 day, whereas the 3 controls spiked a fever for 3 days. During the Clade 1 challenge, no temperature increases were noted in the 6 vaccinates and 1 sentinel, whereas the 3 controls exhibited a slight fever on 2 days and the second sentinel spiked a fever for 3 days. Cumulative clinical scores were tallied for each group and were based on the scores assigned to each animal following daily observations of respiratory rate, nasal discharge, coughing, and anorexia, with a maximum score possible of 7. For the Clade 2 challenge, the 6 vaccinates had a mean clinical score of <1 whereas the 3 controls had a mean of 3.3 for days 2-8 (low of 1.7 to high of 5). The Clade 1 challenge showed similarities where the 6 vaccinates and 1 sentinel had a mean score of <1, the 3 controls had a mean of 2.5 for day 1-8 (low of 0.3 and high of 3.3), and the second sentinel had a mean of 2.7 for day 2-8 (low of 1 high of 5). Overall this data indicates that there was a difference noted in clinical scores between vaccinates and controls for both virus challenges.

Shedding of the challenge virus was also assessed via nasopharyngeal swabs and inoculation of embryonated chicken eggs. When the nasopharyngeal swabs from vaccinated horses were inoculated in eggs, live virus was detectable at least one time post-challenge in every animal, except for 1 in the group challenged with KY/14 WT. EID$_{50}$ titrations of infectious virus content in the swab material collected at day two post-challenge from vaccinated horses showed log titers between 1.750 and 4 in the Rich/07 WT challenged group, and between 0 and 2 in the KY/14 WT challenged group. On the other hand, unvaccinated horses in both groups shed detectable live virus for six or seven days post-challenge, and log titers in the allantoic fluid at two days post-inoculation were between 6.500 and 6.667 in the Rich/07 WT challenged group, and between 4.625 and 7 in the KY/14 WT challenged group. Thus, live virus shedding appeared to be reduced by at least three orders of magnitude or more when vaccinated horses were compared with the unvaccinated ones. Altogether, the results show that the bivalent EIV LAIV vaccine induced protection in horses against both Clade 1 and Clade 2 virus challenges.

Example 4: Development of Bivalent EIV LAIVs Containing a Recent Clade 1 Virus In order to generate a more up-to-date EIV LAIV which fulfills the OIE recommendations, a bivalent EIV LAIV based on the clade 1 A/equine/Texas/6/2017 (TX/17) HA and NA was generated. A strategy identical to that described in Example 2 is used—i.e. a recombinant virus containing the six internal genes (PB2, PB1, PA, NP, M and NS) from Ohio/03 LAIV is used as a master donor virus (MDV), into which the HA and NA genes from more recent clade 1 TX/17 are separately cloned. Proper generation of the TX/17 recombinant virus is similarly confirmed as was done for the Ohio/03 and Rich/07 recombinant viruses. This LAIV offers a further advantage in that it contains a more recently circulating viral strain of clade 1 of the Florida sublineage of H3N8 EIV.

Example 5: Safety and Efficacy of a Bivalent Modified-Live Equine Influenza Virus Vaccine Administered to Horses Intranasally The objective of the study is to evaluate the safety and efficacy of a Clade 1, Clade 2, and Clade 1 and 2 combination modified-live equine influenza virus vaccine, administered intranasally as a single dose to horses. On Day 28, horses are challenged with a virulent strain of equine influenza virus via nebulization, and observed for 21 days post-challenge.

| Treatment Group | IVP/CP | Vaccination (Day 0) | Challenge (Day 28) | End of Study (Day 49) |
|---|---|---|---|---|
| T01 | Placebo | 1 ml; IN | Heterologous EIV strain; IN | Nasal swab; rectal temperature; CO; blood collection |
| T02 | EIV Clade 1 modified-live virus | | | |
| T03 | EIV Clade 2 modified-live virus | | | |
| T04 | EIV Clade 1 and Clade 2 modified-live viruses | | | |

IN = intranasal
CO = clinical observations
Placebo = Phosphate Buffered Saline (PBS)

Animals are allocated to treatment groups using a completely random design. Animals have an acclimation period of at least 7 days prior to the Vaccination Phase 1 housing before vaccination. Animals are relocated to the Challenge Phase housing at least 2 days prior to challenge. Horses are given an appropriate antibiotic (ceftiofur [Excede®] or equivalent) and anthelmintic (moxidectin [Quest®] or equivalent) prior to arrival as approved by the Sponsor and Clinical Representative. The study is valid if animals in T01 control group remain seronegative for EIV (HAI assay titer <8) until the time of challenge, and 75% (6 out of 8) of the T01 animals exhibit clinical disease following challenge (as defined below).

Rectal temperatures of individual animals are taken and recorded from Day −3 through Day 4. If animals have rectal temperatures >102.5° F. prior to Day 0, initiation of the study is delayed to allow body temperatures to return to normal (at least 2 consecutive days with temperatures ≤102.5° F.). If an individual animal is febrile (rectal temperature >102.5° F.) on Day 4, rectal temperature is taken and recorded daily for that animal until the temperature returns to ≤102.5° F. On Day 0, rectal temperatures are measured approximately 30 minutes post-vaccination. All horses must have a normal rectal temperature (≤102.5° F.) for two consecutive days (Day 26 and 27) prior to challenge.

Sick, injured or moribund animals may be treated or removed, as deemed necessary, by a veterinarian after consultation with the Investigator and Clinical or Sponsor Representative. All treatments are documented. Following challenge, horses should not be treated with antibiotics, anti-inflammatory, or other therapeutics that may mask clinical signs or progression of disease. If an animal becomes moribund (recumbent and unable to rise for food and/or water), the animal is euthanized. If possible, the Investigator and Clinical or Sponsor Representative is notified prior to euthanizing any animal. If a delay in consulting the Clinical or Sponsor Representative would cause undue suffering or distress to the animal, the Investigator may choose to euthanize the animal immediately, and inform the Clinical Representative as soon as possible (within 24 hours). Euthanasia is conducted in accordance with the current AVMA Guidelines on Euthanasia (June 2007), and is documented.

A necropsy is performed on animals who die or are euthanized during the study and, if possible, the cause of death determined. Necropsy findings and samples collected are documented.

Blood (1×12.5 mL SST) is collected from individual animals via jugular venipuncture on Days −1, 7, 14, 27, 35, 42, and 49. The samples are labeled, and processed to serum. Serum is divided into 2×1 mL aliquots, with the remaining balance of serum placed in a third aliquot. Sample collection is recorded.

Nasal swabs are collected from individual animals on Days −1, 1-14, 27 (pre-challenge), and 29 through the completion of the study. A single swab is used to collect material from a single nostril and placed into viral transport media. Samples are labeled with a unique sample ID and placed on ice at the time of collection. Nasal swab samples are stored frozen (≤−70° C.) until tested. Sample collection are recorded.

Individual animals are vaccinated with their allotted IVP/CP on Day 0. The IVP/CP is administered as a 1 mL dose into a single nostril using an appropriate sized syringe and nasal cannula. Vaccination is recorded.

Individual animals are observed at least once daily for abnormal clinical signs including, but not limited to, nasal discharge, lethargy, tachypnea (rapid respiration; >40 breaths per min [bpm]) and trembling, on Days −1, 0 (approximately 30 minutes post-vaccination), and 1 through 7. Post-vaccination clinical observations are recorded. On Day 0, post-vaccination clinical observations are recorded approximately 30 minutes after vaccination.

Individual animals are challenged intranasally by means of a horse mask wet nebulizer (Aeromask® ES) on Day 28. Horses may be administered a sedative, such as xylazine or butorphanol per label. Each animal receives an intranasal challenge with a heterologous virulent EIV strain. Challenge is recorded.

Individual animals are observed at least once daily for at least 30 minutes by qualified (i.e. trained) personnel for depression, respiratory effort, cough, and nasal discharge. Each clinical sign is scored per a clinical scoring system. Challenge phase clinical scores are recorded on Days 27 through the completion of the study. On Day 28 (day of challenge), challenge phase clinical observations take place approximately 30 minutes post-challenge.

Should any animal show clinical signs of an unrelated disease, the animal may be removed from the challenge phase of the study upon recommendation by the ARS veterinarian after consultation with the Clinical Representative and/or Sponsor.

Efficacy of the vaccines are determined based on the following laboratory tests:

1) HAI (Hemagglutination Inhibition): Serum samples are pre-treated with potassium periodate and heat inactivated to remove any non-specific inhibitors. Serial dilutions of treated serum are mixed with equal volumes of viral suspensions containing 8 HA units and observed for HA activity.

2) VI (Virus Isolation): Results are reported as positive/negative (qualitative). Nasal swabs are tested for the presence of EIV by virus isolation. Swabs are at room temperature, express, and the media filtered (using 0.45 micron syringe filter). Nasal swab aliquots are tested using embryonated eggs. Briefly, 100 μL of sample are inoculated into 9 to 11-day old embryonated chicken eggs. The eggs are allowed to incubate at 36° C. for 72 hours, with observations 1 day post-incoculation for embryo death. Any egg that dies within the first 24 hours is discarded. At 72 hours post-inoculation, all remaining eggs are placed at 4° C. overnight, and allantoic fluid is harvested and tested by HA.

3) qPCR: Nasal swabs are thawed and RNA extracted. The RNA is quantified using real-time PCR with primers and probe targeting a conserved EIV HA region.

4) RIM (Rapid Immuno-Migration): A commercially available test kit (FLU DETECT® Swine Influenza Virus Type A Antigen Test Kit; Zoetis, USA) is used to screen horses for shedding of Type A Influenza Virus post-vaccination. Manufacturer's instructions are followed. Results are used to determine at what time point vaccinated horses can be comingled during the challenge phase. Results are placed in the study file.

At the conclusion of the study, animals are humanely euthanized, and either buried or chemically digested per site SOPs.

Frequency distributions of post-challenge clinical scores is calculated by treatment and time-point that data is collected. Frequency distribution of ever having each of the post-challenge clinical observations is calculated for each treatment group.

An animal is considered to have clinical disease if it has a rectal temperature ≥103.0° F. (any day post-challenge) and has at least one clinical score for either depression, respiratory effort, cough (score of 1), or nasal discharge (score of 2) on any day post-challenge. The pyrexia and positive clinical score do not have to occur on the same day. Duration and amount of virus shedding data is analyzed as supporting data for vaccine efficacy. Frequency distributions of whether an animal is ever considered diseased or not post-challenge (presence of clinical disease after challenge) is calculated by treatment.

Diseased/not diseased is analyzed with a general linear mixed model with a binomial distribution and logit link function if possible. The fixed effect in the model is treatment with no random effects in the model. The least squares means, standard errors and 90% confidence limits is calculated for each treatment group and back-transformed. Fisher's Exact Test is used to analyze the data if it is not possible to use a generalized mixed model. Contrasts are used to compare treatment group T01 to treatment groups T02-T04.

Regarding virus isolation, frequency distributions of whether an animal shed virus is calculated for each treatment and time point. Duration of virus shedding post-challenge is determined for each animal, and is calculated as (last time point present minus first time point present)+1. Duration of virus shedding is set to zero for animals that have no time points with positive virus isolation. The minimum, maximum, median and quartile non-parametric statistics (5-number summary) is calculated for duration of virus shed for each treatment group.

The duration of virus shedding is analyzed with a general linear mixed model. The fixed effect in the model is treatment and the random effect is the residual. Treatment least squares means, standard errors, 90% confidence limits, minimum and maximums is calculated. Contrasts are used to compare treatment group T01 to treatment groups T02-T04.

Regarding qPCR, the area under the curve (AUC) is calculated for each animal during the challenge phase. Prior to analysis with a general linear mixed model, the AUCs are natural logarithm transformed. The fixed effect in the model is treatment and the random effect is residual. Treatment least squares means, standard errors and 90% confidence limits are back-transformed. Treatment minimums and maximums are also calculated.

If necessary, the challenge VI data are logarithm transformed prior to analysis with a general linear mixed model for repeated measurements. The fixed effects in the model are treatment, time point, and treatment by time point interaction. The fixed effects in the model are animal within treatment, and residual. Treatment least squares means, standard errors, and 90% confidence limits for each time point are back-transformed if necessary. Treatment minimums and maximums are also calculated for each time point. Contrasts are used to compare treatment group T01 to treatment groups T02-T04 at each time point.

Descriptive statistics (mean, standard deviation, minimum and maximum) of temperatures taken during the vaccination phase including temperatures taken previous to the day of challenge are calculated for each treatment group and time point. Challenge phase temperatures, including the day of challenge, are analyzed using the same model as defined in the VI analysis section. Treatment least squares means, standard errors, 90% confidence limits, minimums and maximums are calculated for each time point. Treatments are compared at each time point using contrasts.

Frequency distributions of post-vaccination clinical observations (depression, trembling, tachypnea, nasal discharge, and other) are calculated for each treatment group and time point. Frequency distribution of ever having each of the post-vaccination clinical observations are calculated for each treatment group.

Example 6: Temperature Sensitive Live Attenuated Equine Influenza Virus Based on A/Equine/Ohio/1/2003 H3N8

Mutated Segment 1 or PB2:
1. Mutated Nucleotide Sequence of Segment 1 (PB2):
In bold are indicated the nucleotide changes resulting in N265S amino acid change in PB2 protein. Underlined a ClaI restriction site introduced in the modified PB2 segment.

(SEQ ID NO: 1)

```
agcgaaagcaggtcaaatatattcaatatggagagaataaaagaactgagagatctgatgttacaatcccgcacccgcg agatactaacaaaaactactgtggaccacatggccataatcaagaaatacacatcaggaagacaagagaagaaccctgc acttaggatgaaatggatgatggcaatgaaatacccaatcacggcagataagaggataatggagatgattcctgagaga aatgaacagggacaaacccttggagcaaaacgaacgatgctggctcagaccgcgtaatggtatcacctctggcagtga catggtggaataggaatggaccaacaacaagcacaattcattatccaaaagtctacaaaacttattttgaaaaggttga aagattgaaacacggaacctttggccccgttcattttaggaatcaagtcaagataagacgaagagttgatgtaaaccct ggtcacgcggacctcagtgccaaagaagcacaagatgtgatcatggaagttgttttcccaaatgaagtgggagccagaa ttctaacatcggaatcacaactaacaataaccaaagagaaaaaggaagaacttcaggactgcaaaattgctcccttgat ggtagcatacatgctagaaagagagttggtccgaaaaacaaggttcctcccagtagcaggcggaacaagcagtgtatac attgaagtgttgcatctgactcagggaacatgctgggagcaaatgtacaccccaggaggagaagttagaaacgatgata ttgatcaaagtttaattattgcagcacgatcgatagtgagaagagcaacagtatcagcagatccactagcatccctact ggaaatgtgccacagtacacagattggtggaataaggatggtagacatccttaagcagaatccaacagaggaacaagct gtggatatatgcaaagcagcaatgggattgagaattagctcatcattcagctttggtggattcaccttcaaaagaacaa gtggatcatcagtcaagagagaagaagaaatgcttacgggcaaccttcaaacattgaaaataagaatgcatgagggcta tgaagaattcacaatggtcggaagaagagcaacagctattctcagaaaggcaaccagaagattgattcaattgatagta agtgggagagatgaacaatcaattgctgaagcaataattgtagccatggtgttttcgcaagaagattgcatgataaaag cagttcgaggcgatttgaactttgttaatagagcaaatcagcgtttgaacccccatgcatcaactcttgaggcatttcca aaaagatgcaaaagtgcttttccaaaattggggaattgaacccatcgacaatgtaatggggatgattggaatattgcct gacatgaccccaagcaccgagatgtcattgagaggagtgagagtcagcaaaatgggagtggatgagtactccagcactg agagagtggtggtgagcattgaccgttttttaagagttcgggatcaaaggggaaacatactactgtccctgaagaagt cagtgaaacacaaggaacgaaaagctgacaataatttattcgtcatcaatgatgtgggagattaatggtcccgaatca gtgttggtcaatacttatcaatggatcatcaggaactgggaaattgtaaaaattcagtggtcacaggacccccacaatgt tatacaataagatagaatttgagccattccaatccctggtccctagggccaccagaagccaatacagcggtttcgtaag aaccctgtttcagcaaatgcgagatgtacttggaacatttgatactgctcaaataataaaactcctccctttttgccgct gctcctccggaacagagtaggatgcagttctcttctttgactgttaatgtaagaggttcgggaatgaggatacttgtaa
```

-continued

```
gaggcaattccccagtgttcaactacaataaagccactaaaaggctcacagtcctcggaaaggatgcaggtgcgcttac tgaggacccagatgaaggtacggctggagtagaatctgctgttctaagagggtttctcattttaggtaaagaaaacaag agatatggcccagcactaagcatcaatgaactaagcaaacttgcaaaaggggagaaagccaatgtactaattgggcaag gggacgtagtgttggtaatgaaacggaaacgtgactctagcatacttactgacagccagacagcgaccaaaaggattcg gatggccatcaattagtgttgaattgtttaaaaacgaccttgtttctact
```

2. Amino Acid Sequence of Mutant EIV PB2 Protein:
In bold is indicated the amino acid change N265S.

(SEQ ID NO: 2)
```
MERIKELRDLMLQSRTREILTKITVDHMAIIKKYTSGRQEKNPALRMKWMMAMKYPITADKRIME

MIPERNEQGQTLWSKINDAGSDRVMVSPLAVTWWNRNGPTTSTIHYPKVYKTYFEKVERLKHGTF

GPVHFRNQVKIRRRVDVNPGHADLSAKEAQDVIMEVVFPNEVGARILTSESQLTITKEKKEELQD

CKIAPLMVAYMLERELVRKTRFLPVAGGTSSVYIEVLHLTQGTCWEQMYTPGGEVRNDDIDQSLI

IAARSIVRRATVSADPLASLLEMCHSTQIGGIRMVDILKQNPTEEQAVDICKAAMGLRISSSFSF

GGFTFKRTSGSSVKREEEMLIGNLQTLKIRMHEGYEEFTMVGRRATAILRKATRRLIQLIVSGRD

EQSIAEAIIVAMVESQEDCMIKAVRGDLNEVNRANQRLNPMHQLLRHFQKDAKVLFQNWGIEPID

NVMGMIGILPDMIPSTEMSLRGVRVSKMGVDEYSSTERVVVSIDRFLRVRDQRGNILLSPEEVSE

TQGTEKLIIIYSSSMMWEINGPESVLVNTYQWIIRNWEIVKIQWSQDPTMLYNKIEFEPFQSLVP

RAIRSQYSGFVRTLFQQMRDVLGTFDTAQIIKLLPFAAAPPEQSRMQFSSLIVNVRGSGMRILVR

GNSPVFNYNKATKRLTVLGKDAGALTEDPDEGTAGVESAVLRGFLILGKENKRYGPALSINELSK

LAKGEKANVLIGQGDVVLVMKRKRDSSILTDSQTATKRIRMAIN
```

Mutated Segment 2 or PB1:
1. Mutated Nucleotide Sequence of Segment 2 (PB1):
In bold are indicated the nucleotide changes resulting in K391E, E581G, and A661T amino acid change in PB2 protein. AatI restriction site (denoted by underline) and HindIII restriction site (denoted by underline+italics) were introduced in the modified PB1 segment. Denoted in underline+bold are nucleotide mutated from the original PB1 sequence to remove a BamHI restriction site.

(SEQ ID NO: 3)
```
agcgaaagcaggcaaaccatttgaatggatgtcaatccgactctacttttcttaaaggtgccagcgcaaaatgctataa gcacaacattcccttatactggagatcctccctacagtcatggaacagggacaggatacaccatggatactgtcaacag aacacaccaatattcagaaaaagggaaatggacaacaaacactgagattggagcaccacaacttaatccaatcgatgga ccacttcctgaagacaatgaaccaagtgggtacgcccaaacagattgtgtattggaagcaatggctttccttgaagaat cccatcccggaatctttgaaaattcgtgtcttgaaacgatggaggtgattcagcagacaagagtggacaaactaacaca aggccgacaaacttatgattggaccttgaataggaatcaacctgccgcaacagcacttgctaatacgattgaagtattc agatcaaatggtctgacttccaatgaatcggggagattgatggacttcctcaaagatgtcatggagtccatgaacaagg aagaaatggaataacaacacacttccaacggaagagaagagtaagagacaacatgacaaagagaatggtaacacagag aaccatagggaagaagaaacaacgattaaacagaaagagctatctaatcagaacattaaccctaaacacaatgaccaag gacgctgagagagggaaattgaaacgacgagcaatcgctaccccagggatgcagataagagggtttgtatattttgttg aaacactagcccgaagaatatgtgaaaagcttgaacaatcaggattgccagttggcggtaatgagaaaaaggccaaact ggctaatgtcgtcagaaaaatgatgactaattcccaagacactgaactctccttcaccatcactggggacaataccaaa tggaatgaaaatcagaacccacgcatattcctggcaatgatcacatacataactagaaaccagccagaatggttcagaa atgttctaagcattgcaccgattatgttctcaaataaaatggcaagactggggaaggatatatgtttgaaagcaaaag tatgaaattgagaactcaaataccagcagaaatgctagcaagcattgacctgaaatatttcaatgattcaacaaaaag
```

-continued

```
aaaattgaagaaataaggcctcttctggttgacgggactgcttcactgagtcctggcatgatgatgggaatgttcaaca tgttgagcactgtgctgggtgtatccatattaaacctgggccagaggaaatacacaaagaccacatactggtgggatgg tctgcaatcatccgatgactttgctttgatagtgaatgcgcctaatcatgaaggaatacaagctggagtagacagattc tatagaacttgcaaactggtcgggatcaacatgagcaaaaagaagtcctacataaatagaactggaacattcgaattca caagcttttctaccggtatggttttgtagccaatttcagcatggaactacccagttttggggtttccggaataaatga atctgcagacatgagcattggagtgacagtcatcaaaaacaacatgataaataatgatctcggtcctgccacggcacaa atggcactccaactcttcattaaggattatcggtacacataccggtgccatagaggtgatacccagatacaaaccagaa gatcttttgagttgaagaagctttgggggcagactcgatcaaagactggtctactggtatcagatggggtccaaacct atataacatcagaaacctacacatcccggaagtctgtttaaaatgggagctaatggatgaagattataagggggaggcta tgcaatccattgaatcctttcgttagtcacaaagaaattgaatcagtcaacagtgcagtagtaatgtctgcgcatggcc ctgccaaaagcatggagtatgatgctgttactacaacacattcttggatacccaagaggaaccggtccatattgaacac aagccaaaggggaatactcgaagatgagcagatgtatcagaaatgctgcaacctgtttgaaaaattcttccccagcagc tcatacagaagaccagtcggaatttctagtatggttgaggccatggtgtccagggccgcattgatgcacgaattgact tcgaatctggacggataaagaaggatgagttcgctgagatcatgaagatctgttccaccattgaagagctcagacggca aaaatagtgaatttagcttgatcttcatgaaaaaatgccttgtttctact
```

2. Amino Acid Sequence of Mutant EIV PB1 Protein:
In bold are indicated the amino acid changes K391E, E581G and A661T.

```
                                            (SEQ ID NO: 4)
MDVNPTLLFLKVPAQNAISTTFPYTGDPPYSHGTGTGYTMDTVNRTHQYSEKGKWTTNTEIGAPQ

LNPIDGPLPEDNEPSGYAQTDCVLEAMAFLEESHPGIFENSCLETMEVIQQTRVDKLTQGRQTYD

WTLNRNQPAATALANTIEVFRSNGLTSNESGRLMDFLKDVMESMNKEEMEITTHFQRKRRVRDNM

TKRMVTQRTIGKKKQRLNRKSYLIRTLTLNTMTKDAERGKLKRRAIATPGMQIRGFVYFVETLAR

RICEKLEQSGLPVGGNEKKAKLANVVRKMMTNSQDTELSFTITGDNIKWNENQNPRIFLAMITYI

TRNQPEWFRNVLSIAPIMFSNKMARLGKGYMPESKSMKLRTQIPAEMLASIDLKYFNDSTKKKIE

EIRPLLVDGTASLSPGMMMGMFNMLSTVLGVSILNLGQRKYTKTTYWWDGLQSSDDFALIVNAPN

HEGIQAGVDRFYRTCKLVGINMSKKKSYINRTGTFEFTSFFYRYGFVANFSMELPSFGVSGINES

ADMSIGVTVIKNNMINNDLGPATAQMALQLFIKDYRYTYRCHRGDTQIQTRRSFELKKLWGQIRS

KTGLLVSDGGPNLYNIRNLHIPEVCLKWELMDEDYKGRLCNPLNPFVSHKEIESVNSAVVMSAHG

PAKSMEYDAVTTTHSWIPKRNRSILNTSQRGILEDEQMYQKCCNLFEKFFPSSSYRRPVGISSMV

EAMVSRARIDARTDFESGRIKKDEFAEIMKICSTIEELRRQK
```

Wildtype Segment 1 or PB2:
1. Nucleotide Sequence of Wildtype A/Equine/Ohio/1/2003 H3N8 Segment 1 (PB2):

```
                                            (SEQ ID NO: 5)
agcgaaagcaggtcaaatatattcaatatggagagaataaaagaactgagagatctgatgttacaatcccgcacccgcg agatactaacaaaaactactgtggaccacatggccataatcaagaaatacacatcaggaagacaagagaagaaccctgc acttaggatgaaatggatgatggcaatgaaatacccaatcacggcagataagaggataatggagatgattcctgagaga aatgaacagggacaaacccttggagcaaaacgaacgatgctggctcagaccgcgtaatggtatcacctctggcagtga catggtggaataggaatggaccaacaacaagcacaattcattatccaaaagtctacaaaacttattttgaaaaggttga aagattgaaacacggaacctttggccccgttcattttaggaatcaagtcaagataagacgaagagttgatgtaaaccct
```

-continued

```
ggtcacgcggacctcagtgccaaagaagcacaagatgtgatcatggaagttgttttcccaaatgaagtgggagccagaa ttctaacatcggaatcacaactaacaataaccaaagagaaaaaggaagaacttcaggactgcaaaattgctcccttgat ggtagcatacatgctagaaagagagttggtccgaaaaacaaggttcctcccagtagcaggcggaacaagcagtgtatac attgaagtgttgcatctgactcagggaacatgctgggagcaaatgtacaccccaggaggagaagttagaaacgatgata ttgatcaaagtttaattattgcagcacggaacatagtgagaagagcaacagtatcagcagatccactagcatccctact ggaaatgtgccacagtacacagattggtggaataaggatggtagacatccttaagcagaatccaacagaggaacaagct gtggatatgcaaagcagcaatgggattgagaattagctcatcattcagctttggtggattcaccttcaaaagaacaa gtggatcatcagtcaagagagaagaagaaatgcttacgggcaaccttcaaacattgaaaataagaatgcatgagggcta tgaagaattcacaatggtcggaagaagagcaacagctattctcagaaaggcaaccagaagattgattcaattgatagta agtgggagagatgaacaatcaattgctgaagcaataattgtagccatggtgttttcgcaagaagattgcatgataaaag cagttcgaggcgatttgaactttgttaatagagcaaatcagcgtttgaaccccatgcatcaactcttgaggcatttcca aaaagatgcaaaagtgcttttccaaaattggggaattgaacccatcgacaatgtaatggggatgattggaatattgcct gacatgaccccaagcaccgagatgtcattgagaggagtgagagtcagcaaaatgggagtggatgagtactccagcactg agagtggtggtgagcattgaccgttttttaagagttcgggatcaaagggggaaacatactactgtcccctgaagaagt cagtgaaacacaaggaacggaaaagctgacaataatttattcgtcatcaatgatgtgggagattaatggtcccgaatca gtgttggtcaatacttatcaatggatcatcaggaactgggaaattgtaaaaattcagtggtcacaggaccccacaatgt tatacaataagatagaatttgagccattccaatccctggtcctagggccaccagaagccaatacagcggtttcgtaag aaccctgtttcagcaaatgcgagatgtacttggaacatttgatactgctcaaataataaaactcctcccttttgccgct gctcctccggaacagagtaggatgcagttctcttctttgactgttaatgtaagaggttcgggaatgaggatacttgtaa gaggcaattccccagtgttcaactacaataaagccactaaaaggctcacagtcctcggaaaggatgcaggtgcgcttac tgaggacccagatgaaggtacggctggagtagaatctgctgttctaagagggtttctcattttaggtaaagaaaacaag agatatggcccagcactaagcatcaatgaactaagcaaacttgcaaaaggggagaaagccaatgtactaattgggcaag gggacgtagtgttggtaatgaaacggaaacgtgactctagcatacttactgacagccagacagcgaccaaaaggattcg gatggccatcaattagtgttgaattgtttaaaaacgaccttgtttctact
```

2. Amino Acid Sequence of Wildtype A/Equine/Ohio/1/2003 H3N8 PB2 Protein:

(SEQ ID NO: 6)
MERIKELRDLMLQSRTREILTKTTVDHMAIIKKYTSGRQEKNPALRMKWMMAMKYPITADKRIME

MIPERNEQGQTLWSKTNDAGSDRVMVSPLAVTWWNRNGPTTSTIHYPKVYKTYFEKVERLKHGTF

GPVHFRNQVKIRRRVDVNPGHADLSAKEAQDVIMEVVFPNEVGARILTSESQLTITKEKKEELQD

CKIAPLMVAYMLERELVRKTRFLPVAGGTSSVYIEVLHLTQGTCWEQMYTPGGEVRNDDIDQSLI

IAARNIVRRATVSADPLASLLEMCHSTQIGGIRMVDILKQNPTEEQAVDICKAAMGLRISSSFSF

GGFTFKRTSGSSVKREEEMLTGNLQTLKIRMHEGYEEFTMVGRRATAILRKATRRLIQLIVSGRD

EQSIAEATIVAMVESQEDCMIKAVRGDLNEVNRANQRLNPMHQLLRHFQKDAKVLFQNWGIEPID

NVMGMIGILPDMTPSTEMSLRGVRVSKMGVDEYSSTERVVVSIDRFLRVRDQRGNILLSPEEVSE

TQGTEKLTITYSSSMMWEINGPESVLVNTYQWIIRNWEIVKIQWSQDPTMLYNKIEFEPFQSLVP

RAIRSQYSGEVRTLFQQMRDVLGTFDTAQIIKLLPFAAAPPEQSRMQFSSLIVNVRGSGMRILVR

GNSPVFNYNKATKRLTVLGKDAGALTEDPDEGTAGVESAVLRGFLILGKENKRYGPALSINELSK

LAKGEKANVLIGQGDVVLVMKRKRDSSILTDSQTATKRIRMAIN

Wildtype Segment 2 or PB1:
1. Nucleotide Sequence of Wildtype A/Equine/Ohio/1/2003
H3N8 Segment 2 (PB1):

(SEQ ID NO: 7)

agcgaaagcaggcaaaccatttgaatggatgtcaatccgactctacttttcttaaaggtgccagcgcaaaatgctataa gcacaacattcccttatactggagatcctccctacagtcatggaacagggacaggatacaccatggatactgtcaacag aacacaccaatattcagaaaaagggaaatggacaacaaacactgagattggagcaccacaacttaatccaatcgatgga ccacttcctgaagacaatgaaccaagtgggtacgcccaaacagattgtgtattggaagcaatggctttccttgaagaat cccatcccggaatctttgaaaattcgtgtcttgaaacgatggaggtgattcagcagacaagagtggacaaactaacaca aggccgacaaacttatgattggaccttgaataggaatcaacctgccgcaacagcacttgctaatacgattgaagtattc agatcaaatggtctgacttccaatgaatcggggagattgatggacttcctcaaagatgtcatggagtccatgaacaagg aagaaatggaaataacaacacacttccaacggaagagaagagtaagagacaacatgacaaagagaatggtaacacagag aaccatagggaagaagaaacaacgattaaacagaaagagctatctaatcagaacattaaccctaaacacaatgaccaag gacgctgagagagggaaattgaaacgacgagcaatcgctacccagggatgcagataagagggtttgtatattttgttg aaacactagcccgaagaatatgtgaaaagcttgaacaatcaggattgccagttggcggtaatgagaaaaaggccaaact ggctaatgtcgtcagaaaaatgatgactaattcccaagacactgaactctccttcaccatcactggggacaataccaaa tggaatgaaaatcagaacccacgcatattcctggcaatgatcacatacataactagaaaccagccagaatggttcagaa atgttctaagcattgcaccgattatgttctcaaataaaatggcaagactggggaaaggatatatgtttgaaagcaaaag tatgaaattgagaactcaaataccagcagaaatgctagcaagcattgacctgaaatatttcaatgattcaacaaaaaag aaaattgaaaagatacgaccacttctggttgacgggactgcttcactgagtcctggcatgatgatgggaatgttcaaca tgttgagcactgtgctgggtgtatccatattaaacctgggccagaggaaatacacaaagaccacatactggtgggatgg tctgcaatcatccgatgactttgctttgatagtgaatgcgcctaatcatgaaggaatacaagctggagtagacagattc tatagaacttgcaaactggtcgggatcaacatgagcaaaaagaagtcctacataaatagaactggaacattcgaattca caagcttttctaccggtatggttttgtagccaatttcagcatggaactacccagttttggggtttccggaataaatga atctgcagacatgagcattggagtgacagtcatcaaaaacaacatgataaataatgatctcggtcctgccacggcacaa atggcactccaactcttcattaaggattatcggtacacataccggtgccatagaggtgatacccagatacaaaccagaa gatcttttgagttgaagaaactgtgggaacagactcgatcaaagactggtctactggtatcagatggggtccaaacct atataacatcagaaacctacacatcccggaagtctgtttaaaatgggagctaatggatgaagattataaggggaggcta tgcaatccattgaatcctttcgttagtcacaaagaaattgaatcagtcaacagtgcagtagtaatgtctgcgcatggcc ctgccaaaagcatggagtatgatgctgttgcaacaacacattcttggatccccaagaggaaccggtccatattgaacac aagccaaaggggaatactcgaagatgagcagatgtatcagaaatgctgcaacctgtttgaaaaattcttccccagcagc tcatacagaagaccagtcggaatttctagtatggttgaggccatggtgtccagggcccgcattgatgcacgaattgact tcgaatctggacggataaagaaggatgagttcgctgagatcatgaagatctgttccaccattgaagagctcagacggca aaaatagtgaatttagcttgatcttcatgaaaaaatgccttgtttctact 2. Amino Acid Sequence of Wildtype A/Equine/Ohio/1/2003
H3N8 PB1 Protein:

(SEQ ID NO: 8)
MDVNPILLFLKVPAQNAISTTFPYTGDPPYSHGTGTGYTMDTVNRTHQYSEKGKWTTNTEIGAPQ

LNPIDGPLPEDNEPSGYAQTDCVLEAMAFLEESHPGIFENSCLETMEVIQQTRVDKLIQGRQTYD

WTLNRNQPAATALANTIEVERSNGLTSNESGRLMDFLKDVMESMNKEEMEITTHFQRKRRVRDNM

TKRMVTQRTIGKKKQRLNRKSYLIRTLTLNTMTKDAERGKLKRRAIATPGMQIRGFVYFVETLAR

RICEKLEQSGLPVGGNEKKAKLANVVRKMMTNSQDTELSFTITGDNIKWNENQNPRIFLAMITYI

-continued

TRNQPEWFRNVLSIAPIMFSNKMARLGKGYMFESKSMKLRTQIPAEMLASIDLKYFNDSTKKKIE

RIRPLLVDGTASLSPGMMMGMFNMLSTVLGVSILNLGQRKYTKTTYWWDGLQSSDDFALIVNAPN

HEGIQAGVDRFYRTCKLVGINMSKKKSYINRTGTFEFTSFFYRYGFVANFSMELPSFGVSGINES

ADMSIGVTVIKNNMINNDLGPATAQMALQLFIKDYRYTYRCHRGDTQIQTRRSFELKKLWEQTRS

KTGLLVSDGGPNLYNIRNLHIPEVCLKWELMDEDYKGRLCNPLNPFVSHKEIESVNSAVVMSAHG

PAKSMEYDAVATTHSWIPKRNRSILNTSQRGILEDEQMYQKCCNLFEKFFPSSSYRRPVGISSMV

EAMVSRARIDARIDFESGRIKKDEFAEIMKICSTIEELRRQK

Segment 3 or PA:
1. Nucleotide Sequence of A/Equine/Ohio/1/2003 H3N8 Segment 3 (PA):

(SEQ ID NO: 9)
agcgaaagcaggtactgatccaaaatggaagactttgtgcgacagtgcttcaatccaatgatcgtcgagcttgcggaaa aggcaatgaaagaatatggagaggacccgaaaatcgaaacaaacaaatttgcagcaatatgcactcacttggaagtctg cttcatgtactcggatttccactttattaatgaactgggtgagtcagtggtcatagagtctggtgacccaaatgctctt ttgaaacacagatttgaaatcattgaggggagagatcgaacaatggcatggacagtagtaaacagcatctgcaacacca caagagctgaaaaacctaaatttcttccagatttatacgactataaggagaacagatttgttgaaattggtgtgacaag gagagaagttcacatatactacctggagaaggccaacaaaataaagtctgagaaaacacatatccacattttctcattt acaggagaggaaatggctacaaaagcggactatactcttgatgaagagagtagagccaggatcaagaccagactattca ctataagacaagaaatggccagtagaggcctctgggattcctttcgtcagtccgagagaggcgaagagacaattgaaga aagatttgaaatcacagggacgatgcgcaagcttgccaattacagtctcccaccgaacttctccagccttgaaaattt agagtctatgtggatggattcgaaccgaacggcttcattgagagtaagctttctcaaatgtccaaagaagtaaatgcca gaatcgaaccattttcaaagacaacaccccgaccactcaaaatgccaggtggtccaccctgccatcagcgatctaaatt cttgctaatggatgctctgaaactgagcattgaggacccaagtcacgaggagagggaataccactatatgatgcaatc aaatgcatgaaaactttctttggatggaaagagcccagtattgttaaaccacatgaaaagggtataaacccgaactatc tccaaacttggaagcaagtattagaagaaatacaagaccttgagaacgaagaaaggaccccaagaccaagaatatgaa aaaaacaagccaattgaaatgggcactaggtgaaaatatggcaccagagaaagtggattttgaggattgtaaagacatc agtgatttaaaacagtatgacagtgatgagccagaaacaaggtctcttgcaagttggattcaaagtgagttcaacaaag cttgtgagctgacagattcaagctggatagagctcgatgaaattggggaggatgtcgccccaatagaatacattgcgag catgaggagaaattattttactgctgagatttcccattgtagagcaacagaatatataatgaaaggagtgtacatcaac actgctctactcaatgcatcctgtgctgcgatggatgaatttcaattaattccgatgataagtaaatgcaggaccaaag aagggagaaggaaaacaaatttatatggattcataataaagggaagatcccatttaagaaatgatactgacgtggtgaa ctttgtaagtatggaattttctctcactgatccaagatttgagccacacaaatgggaaaaatactgcgttctagaaatt ggagacatgcttctaagaactgctgtaggtcaagtgtcaagacccatgttttgtatgtaaggacaaatggaacctcta aaattaaaatgaaatggggaatggaaatgaggcgctgcctccttcagtctctgcaacagattgaaagcatgatcgaagc tgagtcctcggtcaaagaaaaggacatgaccaaagaatttttttgagaacaaatcagagacatggcctataggagagtcc cccaaaggagtggaagagggctcaatcgggaaggtttgcaggaccttattagcaaaatctgtgtttaacagtttgtatg catctccacaactggaagggttttcagctgaatctaggaaattacttctcattgttcaggctcttagggataacctgga acctggaacatttgatattggggggttatatgaatcaattgaggagtgcctgattaatgatccctgggttttgcttaat gcatcttggttcaactcctcccttacacatgcactgaagtagttgtggcaatgctactatttgctatccatactgtcca aaaaagtaccttgtttctact 2. Amino Acid Sequence of A/Equine/Ohio/1/2003 H3N8 PA Protein:

(SEQ ID NO: 10)
MEDFVRQCFNPMIVELAEKAMKEYGEDPKIETNKFAAICTHLEVCFMYSDFHFINELGESVVIES

GDPNALLKHRFEIIEGRDRIMAWTVVNSICNITRAEKPKFLPDLYDYKENRFVEIGVIRREVHIY

YLEKANKIKSEKTHIHIFSFIGEEMATKADYILDEESRARIKTRLFTIRQEMASRGLWDSFRQSE

RGEETIEERFEITGIMRKLANYSLPPNFSSLENFRVYVDGFEPNGFIESKLSQMSKEVNARIEPF

SKTTPRPLKMPGGPPCHQRSKFLLMDALKLSIEDPSHEGEGIPLYDAIKCMKTFFGWKEPSIVKP

HEKGINPNYLQIWKQVLEEIQDLENEERTPKTKNMKKISQLKWALGENMAPEKVDFEDCKDISDL

KQYDSDEPETRSLASWIQSEFNKACELTDSSWIELDEIGEDVAPIEYIASMRRNYFTAEISHCRA

TEYIMKGVYINTALLNASCAAMDEFQLIPMISKCRIKEGRRKINLYGFIIKGRSHLRNDTDVVNF

VSMEFSLTDPREEPHKWEKYCVLEIGDMLLRTAVGQVSRPMFLYVRINGTSKIKMKWGMEMRRCL

LQSLQQIESMIEAESSVKEKDMIKEFFENKSETWPIGESPKGVEEGSIGKVCRILLAKSVFNSLY

ASPQLEGFSAESRKLLLIVQALRDNLEPGIFDIGGLYESIEECLINDPWVLLNASWENSFLTHAL

K

Segment 4 or HA:
1. Nucleotide Sequence of A/Equine/Ohio/1/2003 H3N8 Segment 4 (HA):

(SEQ ID NO: 11)
agcaaaagcaggggatatttctgtcaatcatgaagacaaccattatttttgatactactgacccattgggcctacagtca aaacccaatcagtggcaacaacacagccacattgtgtctgggacgccatgcagtagcaaatggaacattggtaaaaaca ataagtgatgatcaaattgaggtgacaaatgctacagaattagttcagagcatttcaacggggaaaatatgcaacaact catatagaattctagatggaagaaattgcacattaatagatgcaatgctaggagaccccactgtgacgcctttcagta tgagaattgggacctctcttatagaaagaagcagcgctttcagcaattgctacccatatgacatccctgactatgcatcg ctccgatccattgtagcatcctcaggaacattggaattcacagcagagggattcacatggacaggtgtcactcaaaacg gaataagtggagcctgcaaaagggatcagccgatagtttctttagccgactgaattggctaacaaaatctggaagctc ttaccccacattgaatgtgacaatgcctaacaataaaaatttcgacaagctatacatctgggggattcatcacccgagc tcaaatcaagagcagacaaaattgtacatccaagaatcaggacgagtaacagtctcaacaaaaagaagtcaacaaacaa taatccctaacatcggatctagaccgtgggtcagaggtcaatcaggcaggataagcatatactggaccattgtaaaacc tggagatatcctaatgataaacagtaatggcaacttagttgcaccgcggggatattttaaattgaaaacagggaaaagc tctgtaatgagatcagatgtacccatagaaatttgtgtgtctgaatgtattacaccaaatggaagcatctccaacgaca agccattccaaaatgtgaacaaagttacatatggaaatgccccaagtatatcaggcaaaacactttaaagctggccac tgggatgaggaatgtaccagaaaagcaaatcagaggaatcttcggagcaatagcgggattcatcgaaaacggctgggaa ggaatggttgatgggtggtatgggttccgatatcaaaactctgaaggaacagggcaagctgcagatctaaagagcactc aagcagccatcgaccagattaatggaaagttaaacagagtgattgaaagaaccaatgagaaattccatcaaatagagaa ggaattctcagaagtagaaggaagaattcaggacttggagaaatatgtgaagacaccaaaatagacctatggtcctac aatgcagaattgctggtggctctagaaaatcaacatacaattgacttaacagatgcagaaatgaataaattatttgaga agactagacgccagttaagagaaaacgcagaagacatgggaggtggatgtttcaagatttaccacaaatgtgataatgc atgcattggatcaataagaaatgggacatatgaccattacatatacagagatgaagcattaaacaaccgatttcagatc aaaggtgtagagttgaaatcaggctacaaagattggatactgtggatttcattcgccatatcatgcttcttaatttgcg ttgttctattgggtttcattatgtgggcttgccaaaaaggcaacatcagatgcaacatttgcatttgagtaaactgata gttaaaaacacccttgtttctact 2. Amino Acid Sequence of A/Equine/Ohio/1/2003 H3N8 HA Protein:

(SEQ ID NO: 12)
MKTTIILILLTHWAYSQNPISGNNTATLCLGRHAVANGTLVKTISDDQIEVTNATELVQSISTGK

ICNNSYRILDGRNCTLIDAMLGDPHCDAFQYENWDLFIERSSAFSNCYPYDIPDYASLRSIVASS

GILEFTAEGFTWIGVTQNGISGACKRGSADSFFSRLNWLIKSGSSYPTLNVIMPNNKNFDKLYIW

GIHHPSSNQEQTKLYIQESGRVIVSTKRSQQIIIPNIGSRPWVRGQSGRISIYWTIVKPGDILMI

NSNGNLVAPRGYFKLKIGKSSVMRSDVPIEICVSECITPNGSISNDKPFQNVNKVTYGKCPKYIR

QNTLKLATGMRNVPEKQIRGIFGAIAGFIENGWEGMVDGWYGFRYQNSEGTGQAADLKSTQAAID

QINGKLNRVIERTNEKFHQIEKEFSEVEGRIQDLEKYVEDTKIDLWSYNAELLVALENQHTIDLT

DAEMNKLFEKTRRQLRENAEDMGGGCFKIYHKCDNACIGSIRNGTYDHYIYRDEALNNRFQIKGV

ELKSGYKDWILWISFAISCFLICVVLLGFIMWACQKGNIRCNICI

Segment 5 or NP:
1. Nucleotide Sequence of A/Equine/Ohio/1/2003 H3N8 Segment 5 (NP):

(SEQ ID NO: 13)
agcaaaagcagggtagataatcactcactgagtgacatcaaagtcatggcgtctcaaggcaccaaacgatcctatgaac agatggaaactgatggggaacgccagaatgcaactgaaatcagagcatctgtcggaaggatggtgggaggaatcggccg gttttatgttcagatgtgtactgagcttaaactaaacgaccatgaagggcggctgattcagaacagcataacaatagaa aggatggtactttcggcattcgacgaaagaagaaacaagtatctcgaggagcatcccagtgctgggaaagaccctaaga aaacgggaggcccgatatacagaaggaaagatgggaaatggatgagggaactcatcctccatgataaagaagaaatcat gagaatctggcgtcaggccaacaatggtgaagacgctactgctggtcttactcatatgatgatctggcactccaatctc aatgacaccacataccaaagaacaagggctcttgttcggactgggatggatcccagaatgtgctctctgatgcaaggct caaccctcccacggagatctggagccgctggtgctgcagtaaaaggtgttggaacaatggtaatggaactcatcagaat gatcaaacgcggaataaatgatcggaatttctggagaggtgaaaatggtcgaagaaccagaattgcttatgaaagaatg tgcaatatcctcaaagggaaatttcagacagcagcacaacgggctatgatggaccaggtgagggaaggccgcaatcctg gaaacgctgagattgaggatctcattttcttggcacgatcagcacttattttgagaggatcagtagcccataaatcatg cctacctgcctgtgtttatggccttgcagtaaccagtgggtatgactttgagaaggaaggatactctctggttggaatt gatcctttcaaactactccagaacagtcaaattttcagtctaatcagaccaaaagaaaacccagcacacaagagccagt tggtgtggatggcatgccattctgcagcatttgaggacctgagagttttaaatttcattagaggaaccaaagtaatccc aagaggacagttaacaaccagaggagttcaaatagcttcaaatgaaaacatggagacaatagattctagcacacttgaa ctgagaagcaaatattgggcaataaggaccagaagcggaggaaacaccagtcaacagagagcatctgcaggacagtaa gtgtgcaacctactttctcagtacagagaaatcttccctttgagagagcaaccattatggctgcattcactggtaacac tgaagggaggacttccgacatgagaacggaaatcataaggatgatggaaaatgccaaatcagaagatgtgtctttccag gggcggggagtcttcgagctctcggacgaaaaggcaacgaacccgatcgtgccttcctttgacatgagcaatgaagggt cttatttcttcggagacaatgctgaggagtttgacaattaaagaaaaataccccttgtttctact 2. Amino Acid Sequence of A/Equine/Ohio/1/2003 H3N8 NP Protein:

(SEQ ID NO: 14)
MASQGTKRSYEQMEIDGERQNATEIRASVGRMVGGIGREYVQMCIELKLNDHEGRLIQNSITIER

MVLSAFDERRNKYLEEHPSAGKDPKKTGGPIYRRKDGKWMRELILHDKEEIMRIWRQANNGEDAT

AGLIHMMIWHSNLNDITYQRTRALVRTGMDPRMCSLMQGSTLPRRSGAAGAAVKGVGIMVMELIR

MIKRGINDRNFWRGENGRRTRIAYERMCNILKGKFQTAAQRAMMDQVREGRNPGNAEIEDLIFLA

RSALILRGSVAHKSCLPACVYGLAVISGYDFEKEGYSLVGIDPFKLLQNSQIFSLIRPKENPAHK

SQLVWMACHSAAFEDLRVLNFIRGTKVIPRGQLTIRGVQIASNENMETIDSSTLELRSKYWAIRT

RSGGNISQQRASAGQISVQPIFSVQRNLPFERATIMAAFIGNTEGRTSDMRTEIIRMMENAKSED

VSFQGRGVFELSDEKATNPIVPSFDMSNEGSYFFGDNAEEFDN

Segment 6 or NA:
1. Nucleotide Sequence of A/Equine/Ohio/1/2003 H3N8 Segment 6 (NA):

(SEQ ID NO: 15)

agcaaaagcaggagtttaaaatgaatccaaatcaaaagataatagcaattggatttgcatcattggggatattaatcat taatgtcattctccatgtagtcagcattatagtaacagtactggtcctcaataacaatagaacagatctgaactgcaaa gggacgatcataagagagtgcaatgaaacagtaagagtagaaaaaattactcaatggtataataccagtacaattaagt acatagagagaccttcaaatgaatactacatgaacaacactgaaccactttgtgaggcccaaggctttgcaccattttc caaagataatggaatacgaattgggtcgagaggccatgttttttgtgataagagaaccttttgtatcatgttcgccctca gaatgtagaacctttttcctcacacagggctcattactcaatgacaaacattctaacggcacagtaaaggaccgaagtc cgtataggactttgatgagtgtcagaataggcaatcacctaatgtatatcaagctaggtttgaatcggtagcatggtc agcaacagcatgccatgatggaaaaaaatggatgacagttggagtcacagggcccgacaatcaagcaattgcagtagtg aactatggaggtgttccggttgatattattaattcatgggcaggggatattttaagaacccaagaatcatcatgcacct gcattaaaggagactgttattgggtaatgactgatggaccggcaaataggcaagctaaatataggatattcaaagcaaa agatggaagagtaattggacagactgatataagtttcaatggggggacacatagaggagtgttcttgttaccccaatgaa gggaaggtggaatgcatatgcagggacaattggactggaacaaatagaccaattctggtaatatcttctgatctatcgt acacagttggatatttgtgtgctggcattcccactgacactcctaggggagaggatagtcaattcacaggctcatgtac aagtcctttgggaaataaaggatacggtgtaaaaggtttcgggtttcgacaaggaactgacgtatgggccggaaggaca attgtaggacttcaagatcaggattcgaaataataaaaatcaggaatggttggacacagaacagtaaagaccaaatca ggaggcaagtgattatcgatgacccaaattggtcaggatatagcggttcttcacattgccggttgaactaacaaaaaa gggatgtttggtcccctgtttctgggttgaaatgattagaggtaaacctgaagaaacaacaatatggacctctagcagc tccattgtgatgtgtggagtagatcataaaattgccagttggtcatggcacgatggagctattcttccctttgacatcg ataagatgtaatttacgaaaaaactccttgtttctact 2. Amino Acid Sequence of A/Equine/Ohio/1/2003 H3N8 NA Protein:

(SEQ ID NO: 16)

MNPNQKIIAIGFASLGILIINVILHVVSIIVIVLVLNNNRIDLNCKGTII

RECNETVRVEKITQWYNTSTIKYIERPSNEYYMNNTEPLCEAQGFAPFSK

DNGIRIGSRGHVFVIREPFVSCSPSECRIFFLIQGSLLNDKHSNGTVKDR

SPYRILMSVRIGQSPNVYQARFESVAWSATACHDGKKWMTVGVIGPDNQA

IAVVNYGGVPVDIINSWAGDILRIQESSCICIKGDCYWVMIDGPANRQAK

YRIFKAKDGRVIGQTDISFNGGHIEECSCYPNEGKVECICRDNWIGINRP

ILVISSDLSYTVGYLCAGIPTDTPRGEDSQFIGSCTSPLGNKGYGVKGFG

FRQGTDVWAGRTISRTSRSGFEIIKIRNGWTQNSKDQIRRQVIIDDPNWS

GYSGSFILPVELIKKGCLVPCFWVEMIRGKPEETTIWTSSSSIVMCGVDH

KIASWSWHDGAILPFDIDKM

Segment 7 or M:
1. Nucleotide Sequence of A/Equine/Ohio/1/2003 H3N8 Segment 7 (M):

(SEQ ID NO: 17)

agcaaaagcaggtagatatttaaagatgagtcttctaaccgaggtcgaaa cgtacgttctctctatcgtaccatcaggcccccctcaaagccgagatcgcg cagagacttgaagatgtctttgcagggaagaacaccgatcttgaggcact catggaatggctaaagacaagaccaatcctgtcacctctgactaaaggga ttttaggatttgtattcacgctcaccgtgcccagtgagcgaggactgcag cgtagacgctttgtccaaaatgcccttagtggaaacggagatccaaacaa -continued

```
catggacagagcagtaaaactgtacaggaagcttaaaagagaaataacat tccatggggcaaaagaggtggcactcagctattccactggtgcactagcc agctgcatgggactcatatacaacagaatgggaactgttacaaccgaagt ggcatttggcctggtatgcgccacatgtgaacagattgctgattccagc atcgatctcacaggcagatggtgacaacaaccaacccattaatcagacat gaaaacagaatggtattagccagtaccacggctaaagccatggaacagat ggcaggatcgagtgagcaggcagcagaggccatggaggttgctagtaggg ctaggcagatggtacaggcaatgagaaccattgggacccaccctagctcc agtgccggtttgaaagatgatctcattgaaaatttacaggcctaccagaa acggatgggagtgcaaatgcagcgattcaagtgatcctctcgttattgca gcaagtcattgggatcttgcacttgatattgtggattcttgatcgtct tttcttcaaattcatttatcgtcgccttaaatacgggttgaaaagaggc cttctacggaaggagtacctgagtctatgagggaagaatatcggcaggaa cagcagaatgctgtggatgttgacgatggtcattttgtcaacatagagct ggagtaaaaaactaccttgtttctact
```

2. Amino Acid Sequence of A/Equine/Ohio/1/2003 H3N8 M1 Protein:

(SEQ ID NO: 18)
MSLLTEVETYVLSIVPSGPLKAEIAQRLEDVFAGKNIDLEALMETNLKTR
PILSPLIKGILGFVFTLTVPSERGLQRRRFVQNALSGNGDPNNMDRAVKL
YRKLKREITFHGAKEVALSYSTGALASCMGLIYNRMGTVITEVAFGLVCA
TCEQIADSQHRSHRQMVITTNPLIRHENRMVLASTTAKAMEQMAGSSEQA
AEAMEVASRARQMVQAMRTIGTHPSSSAGLKDDLIENLQAYQKRMGVQMQ
RFK

3. Amino Acid Sequence of A/Equine/Ohio/1/2003 H3N8 M2 Protein:

(SEQ ID NO: 19)
MSLLTEVETPTRNGWECKCSDSSDPLVIAASIIGILHLILWILDRLFFKF
IYRRLKYGLKRGPSTEGVPESMREEYRQEQQNAVDVDDGHFVNIELE

Segment 8 or NS:
1. Nucleotide Sequence of A/Equine/Ohio/1/2003 H3N8 Segment 8 (NS):

(SEQ ID NO: 20)
```
agcaaaagcagggtgacaaaaacataatggattccaacactgtgtcaagc tttcaggtagactgttttctttggcatgtccgcaaacgattcgcagacca agaactgggtgatgccccattccttgaccggcttcgccgagaccagaagt ccctaaggggaagaggtagcactcttggtctggacatcgaaacagccact catgcaggaaagcagatagtggagcagattctggaaaaggaatcagatga ggcacttaaaatgaccattgcctctgttcctacttcacgctacttaactg acatgactcttgatgagatgtcaagagactggttcatgctcatgcccaag caaaaagtaacaggctcccatgtataagaatggaccaggcaatcatgga
```

-continued

```
taagaacatcatacttaaagcaaactttagtgtgattttcgaaaggctgg aaacactaatactacttagagccttcaccgaagaaggagcagtcgttggc gaaatttcaccattaccttctcttccaggacatactaatgaggatgtcaa aaatgcaattgggtcctcatcggaggacttaaatggaatgataatacgg ttagaatctctgaaactctacagagattcgcttggagaagcagtcatgag aatgggagaccttcattcccttcaaagcagaaatgaaaaatggagagaac aattaagccagaaatttgaagaaataagatggttgattgaagaagtgcga catagattgaaaaatacagaaaatagttttttgaacaaataacatttatgca agccttacaactattgcttgaagtagaacaagagataagaactttctcgt ttcagcttatttaatgataaaaaacaccttgtttctact
```

2. Amino Acid Sequence of A/Equine/Ohio/1/2003 H3N8 M1 Protein:

(SEQ ID NO: 21)
MDSNTVSSFQVDCFLWHVRKRFADQELGDAPFLDRLRRDQKSLRGRGSTL
GLDIETATHAGKQIVEQILEKESDEALKMTIASVPISRYLTDMILDEMSR
DWFMLMPKQKVIGSLCIRMDQAIMDKNIILKANFSVIFERLETLILLRAF
TEEGAVVGEISPLPSLPGHTNEDVKNAIGVLIGGLKWNDNTVRISETLQR
FAWRSSHENGRPSFPSKQK

3. Amino Acid Sequence of A/Equine/Ohio/1/2003 H3N8 M2 Protein:

(SEQ ID NO: 22)
MDSNITSSFQDILMRMSKMQLGSSSEDLNGMIIRLESLKLYRDSLGEAVM
RMGDLHSLQSRNEKTNREQLSQKFEEIRTNLIEEVRHRLKNTENSFEQIT
FMQALQLLLEVEQEIRTFSFQLI

Example 7: Segment 4 (HA) and Segment 6 (NA) Sequences of A/equine/Richmond/1/2007 H3N8

Nucleotide Sequence of Segment 4 (HA) of A/equine/Richmond/1/2007 H3N8

(SEQ ID NO: 23)
agcaaaagcagggga tatttctgtcaatcATGAAGACAACCATTATTTTT
ATTTTTATACTACTGACCCATTGGGCCTACAGTCAAAACCCAATCAGTAA
CAACAACACAGCCACATTGTGTCTGGGACACCATGCAGTAGCAAATGGAA
CATTAGTAAAAACAATAAGTGATGATCAAATTGAGGTGACAAATGCTACA
GAATTAGTTCAGAGCATTTCAATGGGAAAATATGCAACAACTCATATAG
AATTCTAGATGGAAGAAATTGCACATTAATAGATGCAATGCTAGGAGACC
CCCACTGTGACGTCTTTCAGTATGAGAATTGGGACCTCTTTATAGAAAGA
AGCAGCGCTTTCAGCAATTGCTACCCATATGACATCCCTGACTATGCATC
GCTCCGATCAATTGTAGCATCCTCAGGAACATTGGAATTCACAGCAGAGG
GATTCACATGGACAGGTGTCACTCAAAACGGAAGAAGTGGAGCCTGCAAA
AGGGGATCAGCCGATAGTTTCTTTAGCCGACTGAATTGGCTAACAAAATC
TGGAAACTCTTATCCCACATTGAATGTGACAATGCCTAACAATAAAAATT -continued

```
TCGACAAGCTATACATCTGGGGGATTCATCACCCGAGTTCAAATCAAGAG

CAGACAAAATTGTATATCCAAGAATCAGGACGAGTAACAGTCTCAACAAA

AAGAAGTCAACAAACAATAATCCCTAACATCGGATCTAGACCGTGGGTCA

GAGGTCAATCAGGCAGGATAAGCATATACTGGACCATTGTAAAACCTGGA

GATATCCTAATGATAAACAGTAATGGCAACTTAGTTGCACCGCGGGATA

TTTTAAATTGAAAACAGGGAAAAGCTCTGTAATGAGATCAGATGTACCCA

TAGACATTTGTGTGTCTGAATGTATTACACCAAATGGAAGCATCTCCAAC

GAAAAGCCATTCCAAAATGTAAACAAAGTTACATATGGAAAATGCCCCAA

ATATATCAGGCAAAACACTTTAAAGTTGGCCACTGGAATGAGAAATGTAC

CAGAAAAGCAAATCAGAGGAATCTTTGGAGCAATAGCGGGATTCATCGAA

AACGGCTGGGAAGGAATGGTTGATGGGTGGTATGGGTTCCGATACCAAAA

CTCTGAAGGAACAGGACAAGCTGCAGATCTAAAGAGCACTCAAACAGCCA

TCGACCAGATTAATGAAAAGTTAAACAGAGTGATTGAAAGAACCAATGAA

AAATTCCATCAGATAGAGAAGGAATTCTCAGAAGTAGAAGGAAGAATTCA

GGACTTGGAGAAATATGTGGAAGACACCAAAATAGACCTATGGTCCTACA

ATGCAGAATTGCTGGTGGCTCTAGAAAATCAACATACAATTGACTTAACA

GATGCAGAAATGAATAAATTATTCGAGAAGACTAGACGCCAGTTAAGAGA

AAACGCAGAAGACATGGGAGGTGGATGTTTCAAGATTTACCACAAATGTG

ATAATGCATGCATTGGATCAATAAGAAATGGGACATATGACCATTACATA

TACAGAGATGAAGCATTAAACAACCGATTTCAAATCAAAGGTGTTGAGTT

GAAATCAGGCTACAAAGATTGGATACTGTGGATTTCATTCGCCATATCAT

GCTTCTTAATTTGCGTTGTTCTATTGGGTTTTATTATGTGGGCTTGCCAA

AAAGGCAACATCAGATGCAACATTTGCATTTGAgtaaactgatagttaaa

Aacaccttgtttctact
```

Amino Acid Sequence of HA Protein of A/Equine/Richmond/1/2007 H3N8

(SEQ ID NO: 24)
```
MKTTIIFIFILLTHWAYSQNPISNNNTATLCLGHHAVANGTLVKTISDDQ

IEVTNATELVQSISMGKICNNSYRILDGRNCTLIDAMLGDPHCDVFQYEN

WDLFIERSSAFSNCYPYDIPDYASLRSIVASSGTLEFTAEGFTWTGVTQN

GRSGACKRGSADSFFSRLNWLTKSGNSYPTLNVTMPNNKNFDKLYIWGIH

HPSSNQEQTKLYIQESGRVIVSTKRSQQTIIPNIGSRPWVRGQSGRISIY

WTIVKPGDILMINSNGNLVAPRGYFKLKTGKSSVMRSDVPIDICVSECIT

PNGSISNEKPFQNVNKVTYGKCPKYIRQNTLKLATGMRNVPEKQIRGIFG

AIAGFIENGWEGMVDGWYGFRYQNSEGTGQAADLKSTQTAIDQINEKLNR

VIERTNEKEHQIEKEFSEVEGRIQDLEKYVEDTKIDLWSYNAELLVALEN

QHTIDLTDAEMNKLFEKTRRQLRENAEDMGGGCFKIYHKCDNACIGSIRN

GTYDHYIYRDEALNNREQIKGVELKSGYKDWILWISFAISCFLICVVLLG

FIMWACQKGNIRCNICI
```

Nucleotide Sequence of Segment 6 (NA) of A/Equine/Richmond/1/2007 H3N8

(SEQ ID NO: 25)
```
agcaaaagcaggagtttaaaATGAATCCAAATCAAAAGATAATAACAATT

GGATCTGCATCATTGGGGATATTAATCATTAACGTCATTCTCCATGTAGT

CAGCATTATAGTAACAGTACTGGTCCTCAATAACAATGAAACAGGTCTGA

ACTGCAAAGGGACGATCATAAGAGAGTACAATGAAACAGTAAGAGTAGAA

AAAATTACTCAATGGCATAATACCAGTGCAATTAAGTACATAGAGAGACC

TCCAAATGAATACTACATGAACAACACCGAACCACTTTGTGAGGCCCAAG

GCTTTGCACCATTTTCCAAAGATAATGGAATACGAATTGGGTCGAGAGGC

CATGTTTTTGTGATAAGAGAACCTTTTGTATCATGTTCGCCCTCAGAATG

TAGAACCTTTTTCCTCACACAGGGCTCATTACTCAATGACAAACATTCTA

ACGGCACAGTAAAGGATCGAAGTCCATATAGGACTTTGATGAGTGTCAAA

ATAGGGCAATCACCTAATGTGTATCAAGCTAGGTTTGAATCGGTGGCATG

GTCAGCAACAGCATGCCATGATGGAAAAAAATGGATGACAATTGGAGTCA

CAGGGCCCGACAATCAAGCAATTGCAGTAGTGAACTATGGGGGTGTTCCG

GTTGATATTATTAATTCATGGGCAGGGGACATCTTAAGAACCCAAGAATC

ATCATGCACCTGCATTAAAGGAAACTGTTATTGGGTAATGACTGATGGAC

CGGCAAATAGGCAAGCTAAATATAGAATATTCAAAGCAAAAGATGGAAGA

GTAATTGGACAGACTGATATAAGCTTCAATGGGGACACATAGAGGAGTG

TTCTTGTTACCCCAATGAAGGGAAGGTGGAATGCATATGCAGGGACAATT

GGACTGGAACAAATAGACCAATTCTGGTAATATCTTCTGATCTATCGTAC

ACAGTTGGATATTTGTGTGCTGGCATTCCCACTGACACTCCTAGGGGAGA

GGATAGTCAATTCACAGGCTCATGTACAAGTCCTTTGGGAAATAAAGGAT

ACGGTGTAAAAGGTTTCGGGTTTCGACAAGGAACTGACGTATGGGCCGGA

AGGACAATTAGTAGGACTTCGAGATCAGGATTCGAAATAATAAAAATCAG

GAATGGTTGGACACAGAACAGTAAAGACCAAATCAGGAGGCAAGTGATTA

TCGATGACCCAAATTGGTCAGGATATAGCGGTTCTTTCACATTGCCGATT

GAACTAACAAAAAAGGGATGTTTGGTCCCCTGTTTCTGGGTTGAAATGAT

TAGAGGTAAACCTGAAGAACAACAATATGGACCTCTAGCAGCTCCATTG

TGATGTGTGGAGTAGATCATAAAATTGCCAGTTGGTCATGGCACGATGGA

GCTATTCTTCCCTTTGACATCGATAAGATGTAAtttacgaaaaaactcct tgtttctact
```

Amino Acid Sequence of NA Protein of A/Equine/Richmond/1/2007 H3N8

(SEQ ID NO: 26)
```
MNPNQKIITIGSASLGILIINVILHVVSIIVTVLVLNNNETGLNCKGTII

REYNETVRVEKITQWHNTSAIKYIERPPNEYYMNNTEPLCEAQGFAPFSK

DNGIRIGSRGHVEVIREPFVSCSPSECRTFELTQGSLLNDKHSNGTVKDR

SPYRTLMSVKIGQSPNVYQARFESVAWSATACHDGKKWMTIGVTGPDNQA

IAVVNYGGVPVDIINSWAGDILRTQESSCICIKGNCYWVMTDGPANRQAK
```

YRIFKAKDGRVIGQTDISENGGHIEECSCYPNEGKVECICRDNWTGINRP

ILVISSDLSYTVGYLCAGIPTDTPRGEDSQFTGSCTSPLGNKGYGVKGEG

FRQGTDVWAGRTISRTSRSGFEIIKIRNGWTQNSKDQIRRQVIIDDPNWS

GYSGSFTLPIELIKKGCLVPCFWVEMIRGKPEETTIWTSSSSIVMCGVDH

KIASWSWHDGAILPFDIDKM

Example 8. Segment 4 (HA) and Segment 6 (NA) Sequences of Influenza A/equine/Texas/6/2017 H3N8

Nucleotide Sequence of Segment 4 (HA) of Influenza A/Equine/Texas/6/2017 H3N8

(SEQ ID NO: 27)
AGCGAAAGCAGGGGATATTTCTGTCAATCATGACGATAACCAT

TATTTTGATACTACTGACCCATTGGGCTTACAGTCAAAACCCAATCAATG

ACAACAACACAGCCACATTGTGTCTAGGACACCATGCAGTAGCAAATGGA

ACATTGGTAAAAACAATAAGTGATGATCAAATTGAGGTGACAAATGCTAC

AGAATTAGTTCAGAGCATTCCAATGGGGAAAATATGCAACAATTCGTATA

GAATTCTAGATGGAAAGGATTGCACATTAATAGATGCAATGCTAGGAGAC

CCCCACTGTGACGCCTTTCAGTATGAGAATTGGGACCTCTTTATAGAAAG

AAGCAGCGCCTTCAGCAATTGCTACCCATATGACATCCCTAACTATGCAT

CGCTCCGATCCATTGTAGCATCCTCAGGAACATTGGAATTCACAGCAGAG

GGATTCACATGGACAGGTGTCACTCAAAACGGAAGAAGCGGATCCTGCAA

AAGGGGATCAGCCGATAGTTTCTTTAGCCGACTGAATTGGCTAACAAAAT

CCGGAAGCTCTTACCCCACATTGAATGTGACAATGCCTAACAATAAAAAC

TTCGACAAGCTATACATCTGGGGGATCCATCACCCGAGCTCAACTCAAGA

GCAGACAAAATTGTATATCCAGGAATCAGGGCGAGTAACAGTCTCAACAA

AAAGAAGTCAACAAACAATAATCCCTAACATTGGGTCTAGACCATGGATC

AGAGGTCAATCAGGTAGGATAAGCATATACTGGACCATTGTAAAACCTGG

AGATATTCTAATGATAAACAGTAATGGCAACTTAGTTGCACCGCGGGGAT

ACTTTAAATTGAAAACAGGGAAAAGCTCTGTAATGAGATCAGATGTACCC

ATAGACATTTGTGTGTCTGAATGTATTACACCAAATGGAAGCATCTCCAA

CGACAAGCCATTCCAAAATGTGAACAAAGTTACATATGGAAAATGTCCCA

AGTATATCAGACAAAACACTTTAAAGCTGGCCACTGGGATGAGGAATGTA

CCAGAAAAGCAAATCAGAGGAATCTTCGGGGCAATAGCGGGATTCATCGA

AAACGGCTGGGAAGGAATGGTTGATGGATGGTATGGGTTCCGATACCAAA

ACTCTGAAGGAACAGGGCAAGCTGCAGATCTAAAGAGCACTCAAGCAGCC

ATCGACCAGATCAATGGAAAGTTAAACAGAGTGATTGAAAGAACAAATGA

GAATTCCATCAAATAGAGAAGGAATTCTCAGAAGTAGAAGGAAGAATTC

AGGACTTGGAGAAATATGTAGAAGACACCAAAATAGACCTATGGTCCTAC

AATGCAGAATTGCTGGTGGCTCTAGAAAATCAACATACAATTGACTTAAC

AGATGCAGAAATGAATAAATTGTTTGAGAGAACTAGACGCCTGTTAAGAG

AAAACGCAGAAGACATGGGAGGTGGATGTTTCAAGATTTACCACAAATGT

AATAATGCATGCATTGGATCAATAAGAAATGGGACATATGACCATTACAT

ATACAGAGATGAAGCATTAAACAACCGATTTCAGATCAAAGGTGTAGAGT

TGAAATCAGGCTACAAAGATTGGATACTCTGGATTTCATTCGCCATATCA

TGCTTCTTAATTTGCGTTGTTCTATTGGGTTTTATTATGTGGGCTTGCCA

AAAAGGCAACATCAGATGCAACATTTGCATTTGAGTAGATTAATAGTTAA

AAACACCCTTGTTTCTACT

Amino Acid Sequence of HA Protein of Influenza A/Equine/Texas/6/2017 H3N8

(SEQ ID NO: 28)
MTITIILILLTHWAYSQNPINDNNTATLCLGHHAVANGTLVKTISDD

QIEVTNATELVQSIPMGKICNNSYRILDGKDCTLIDAMLGDPHCDAFQYE

NWDLFIERSSAFSNCYPYDIPNYASLRSIVASSGTLEFTAEGFTWTGVTQ

NGRSGSCKRGSADSFFSRLNWLTKSGSSYPTLNVTMPNNKNFDKLYIWGI

HHPSSTQEQTKLYIQESGRVTVSTKRSQQTIIPNIGSRPWIRGQSGRISI

YWTIVKPGDILMINSNGNLVAPRGYFKLKTGKSSVMRSDVPIDICVSECT

TPNGSISNDKPFQNVNKVTYGKCPKYIRQNTLKLATGMRNVPEKQIRGIF

GAIAGFIENGWEGMVDGWYGFRYQNSEGTGQAADLKSTQAAIDQINGKLN

RVIERTNEKFHQIEKEFSEVEGRIQDLEKYVEDTKIDLWSYNAELLVALE

NQHTIDLTDAEMNKLFERTRRLLRENAEDMGGGCFKIYHKCNNACIGSIR

NGTYDHYIYRDEALNNRFQIKGVELKSGYKDWILWISFAISCFLICVVLL

GFIMWACQKGNIRCNICI

Nucleotide Sequence of Segment 6 (NA) of Influenza A/Equine/Texas/6/2017 H3N8

(SEQ ID NO: 29)
AGCAAAAGCAGGAGTTTAAAATGAATCCAAATCAAAAGATAAT

AGCAATTGGATTTACATCATTGGGGATATTAATCATTAGTGTCATTCTCC

ATGTAGTCAGCATTATAGTAACAGTACTGGCCCTAAATAACAACAGAACA

GATCTGAACTGCAAAGAGACGATCATAAGGGAGTACAATGAAACAGTAAG

AGTAGAAAAAATTACTCAATGGTATAATATCAGTACAATTAAGTACATAG

AGAAACCTTCAAATGAATACTATATGAACAACACTGAACCACTTTGTGAG

GCCCAAGGCTTTGCACCATTTTCCAAAGATAATGGAATACGAATTGGATC

GAGGGGCCATGTTTTTGTGATAAGAGAACCTTTTGTATCATGTTCGCCTT

CAGAATGTAGAACCTTTTTCCTCACACAGGGCTCATTACTCAATGACAAA

CATTCTAACGGCACAATAAAGGACCGAAGTCCGTATAGAACTCTGATGAG

TGTCAAAATAGGGCAATCACCTAATGTATATCAAGCTAGGTTTGAATCAG

TGGCATGGTCAGCAACAGCATGCCATGATGGAAAAAAATGGATGACGGTT

GGAGTCACAGGGCCTGACAACCAAGCAATTGCAGTAGTGAACTATGGGGG

TGTTCCGGTTGATATTATTAATTCATGGGCAGGGGATATTTTAAGAACCC

```
                                    -continued
AAGAATCGTCATGCACCTGCATCAAAGGAGATTGTTATTGGGTAATGACT

GATGGGCCGGCGAATAGGCAAGCCAAATATAAGATATTCAAAGCAAAAA

TGGAAAAGTAATTGGACAAACTGATATAAGTTTCAATGGAGGACACATAG

AGGAGTGTTCTTGTTACCCCAATGAAGGGAAGGTGGAATGCATATGCAGG

GACAATTGGACTGGAACAAATAGACCAATTTTGGTAATATCTTCTGATCT

ATCATACACAGTTGGATATTTGTGTGCTGGCATTCCCACTGACACTCCTA

GGGGAGAGGATAGTCAATTCACGGGCTCATGTACAAACCCTTTGGGAAAT

AAAGGATACGGTGTAAAAGGTTTCGGATTTCGACAAGGAACTGACGTATG

GGCCGGAAGGACAATTAGTAGAACTTCAAGATCAGGATTCGAAATAATAA

AAATCAGGAATGGTTGGACACAGAACAGTAAAGACCAAATAAGGAGGCAA

GTGATTATCGATGATCAAAATTGGTCAGGATATAGCGGTTCTTTCACATT

GCCGGTTGAACTAACAAAAAAAGAATGTTTGGTGCCCTGTTTCTGGGTTG

AAATGATTAGAGGTAAACCTGAAGAAAAAACAATATGGACCTCTAGCAGC

TCCATTGTGATGTGTGGAGTAGATCATAAAATTGCCAGTTGGTCATGGCA

CGATGGAGCTATTCTTCCCTTTGACATCGATAAGATGTAATTTACGAAAA

AACTCCTTGTTTCTACT
```

Amino Acid Sequence of NA Protein of Influenza A/equine/Texas/6/2017 H3N8

(SEQ ID NO: 30)
MNPNQKIIAIGFTSLGILIISVILHVVSIIVTVLALNNNRTDLNCKETII

REYNETVRVEKITQWYNISTIKYIEKPSNEYYMNNTEPLCEAQGFAPFSK

DNGIRIGSRGHVFVIREPFVSCSPSECRTFFLTQGSLLNDKHSNGTIKDR

SPYRTLMSVKIGQSPNVYQARFESVAWSATACHDGKKWMTVGVTGPDNQA

IAVVNYGGVPVDIINSWAGDILRTQESSCTCIKGDCYWVMTDGPANRQAK

YKIFKAKNGKVIGQTDISFNGGHIEECSCYPNEGKVECICRDNWTGTNRP

ILVISSDLSYTVGYLCAGIPTDTPRGEDSQFTGSCTNPLGNKGYGVKGFG

FRQGTDVWAGRTISRTSRSGFEIIKIRNGWTQNSKDQIRRQVIIDDQNWS

GYSGSFTLPVELTKKECLVPCFWVEMIRGKPEEKTIWTSSSSIVMCGVDH

KIASWSWHDGAILPFDIDKM

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A multivalent immunological composition comprising two or more equine live-attenuated influenza viruses (LAIV), comprising:
    a first LAIV expressing one or more antigens of a clade 1 H3N8 equine influenza virus; and
    a second LAIV expressing one or more antigens of a clade 2 H3N8 equine influenza virus;
    wherein each LAIV comprises one or more mutations in one or more of: segment 1 and segment 2 of the viral genome;
    wherein the first LAIV expresses HA, NA, or a combination thereof of A/equine/Texas/6/2017 H3N8.

2. The composition of claim 1, wherein the second LAIV expresses HA, NA, or a combination thereof of A/equine/Richmond/1/2007 H3N8.

3. The composition of claim 1 wherein the segment 1 comprises the nucleic acid sequence set forth in SEQ ID NO: 1.

4. The composition of claim 1, wherein the segment 2 comprises the nucleic acid sequence set forth in SEQ ID NO: 3.

5. The composition of claim 1, wherein at least one LAIV comprises one or more mutations in segment 1, which encodes mutant PB2.

6. The composition of claim 5, wherein mutant PB2 comprises a N265S point mutation, relative to SEQ ID NO: 6.

7. The composition of claim 5 mutant PB2 comprises the amino acid sequence set forth in SEQ ID NO: 2.

8. The composition of claim 1, wherein at least one LAIV comprises one or more mutations in segment 2, which encodes mutant PB1.

9. The composition of claim 8, wherein mutant PB1 comprises one or more of: K391E point mutation, relative to SEQ ID NO: 8, E581G point mutation, relative to SEQ ID NO: 8, and A661T point mutation, relative to SEQ ID NO: 8.

10. The composition of claim 8, wherein mutant PB1 comprises a K391E point mutation, relative to SEQ ID NO: 8, a E581G point mutation, relative to SEQ ID NO: 8, and an A661T point mutation, relative to SEQ ID NO: 8.

11. The composition of claim 8, wherein mutant PB1 comprises the amino acid sequence set forth in SEQ ID NO: 4.

12. The composition of claim 1, wherein each LAIV comprises one or more mutations in segment 1, which encodes mutant PB2; and one or more mutations in segment 2, which encodes mutant PB1.

13. The composition of claim 12, wherein mutant PB2 comprises a N265S point mutation, relative to SEQ ID NO: 6 and wherein mutant PB1 comprises a K391E point mutation, relative to SEQ ID NO: 8, a E581G point mutation, relative to SEQ ID NO: 8, and an A661T point mutation, relative to SEQ ID NO: 8.

14. The composition of claim 1, wherein the composition is used for the treatment of equine influenza in a subject.

15. The composition of claim 1, wherein segment 1 of each LAIV is derived from segment 1 of A/equine/Ohio/1/2003; and wherein segment 2 of each LAIV is derived from segment 2 of A/equine/Ohio/1/2003.

16. A method for inducing an immune response against a plurality of equine influenza viruses in a subject, the method comprising administering to the subject the immunological composition of claim 1.

17. The method of claim 16, wherein the subject does not have equine influenza, and wherein the method induces immunity against equine influenza.

18. The method of claim 16, wherein the subject is infected equine influenza, and wherein the method induces a therapeutic immune response.

19. The method of claim 16, wherein the immunological composition is administered intranasally, intratracheally, orally, intradermally, intramuscularly, intraperitoneally, intravenously, or subcutaneously.

20. The method of claim 16, wherein the subject is a horse.

* * * * *

SEQUENCE LISTING

```
<160> NUMBER OF SEQ ID NOS: 30

<210> SEQ ID NO 1
<211> LENGTH: 2341
<212> TYPE: DNA
<213> ORGANISM: Artificial Sequence
<220> FEATURE:
<223> OTHER INFORMATION: Chemically synthesized - mutant segment 1 based
      on A/equine/Ohio/1/2003 H3N8 EIV

<400> SEQUENCE: 1
agcgaaagca ggtcaaatat attcaatatg gagagaataa aagaactgag agatctgatg      60
ttacaatccc gcacccgcga gatactaaca aaaactactg tggaccacat ggccataatc     120
aagaaataca catcaggaag acaagagaag acccctgcac ttaggatgaa atggatgatg     180
gcaatgaaat acccaatcac ggcagataag aggataatgg agatgattcc tgagagaaat     240
gaacagggac aaacccttg gagcaaaacg aacgatgctg gctcagaccg cgtaatggta     300
tcacctctgg cagtgacatg gtggaatagg aatggaccaa caacaagcac aattcattat     360
ccaaaagtct acaaaactta ttttgaaaag gttgaaagat tgaaacacgg aaccttggc     420 cccgttcatt ttaggaatca agtcaagata agacgaagag ttgatgtaaa ccctggtcac     480
gcggacctca gtgccaaaga agcacaagat gtgatcatgg aagttgtttt cccaaatgaa     540
gtgggagcca gaattctaac atcggaatca caactaacaa taaccaaaga gaaaaggaa     600 gaacttcagg actgcaaaat tgctcccttg atggtagcat acatgctaga aagagagttg     660
gtccgaaaaa caaggttcct cccagtagca ggcgaacaa gcagtgtata cattgaagtg     720
ttgcatctga ctcagggaac atgctgggag caaatgtaca ccccaggagg agaagttaga     780
aacgatgata ttgatcaaag tttaattatt gcagcacgat cgatagtgag aagagcaaca     840
gtatcagcag atccactagc atccctactg gaaatgtgcc acagtacaca gattggtgga     900
```

```
ataaggatgg tagacatcct taagcagaat ccaacagagg aacaagctgt ggatatatgc    960
aaagcagcaa tgggattgag aattagctca tcattcagct tggtggatt caccttcaaa   1020 agaacaagtg gatcatcagt caagagagaa gaagaaatgc ttacgggcaa ccttcaaaca   1080
ttgaaaataa gaatgcatga gggctatgaa gaattcacaa tggtcggaag aagagcaaca   1140
gctattctca gaaaggcaac cagaagattg attcaattga tagtaagtgg gagagatgaa   1200
caatcaattg ctgaagcaat aattgtagcc atggtgtttt cgcaagaaga ttgcatgata   1260
aaagcagttc gaggcgattt gaactttgtt aatagagcaa atcagcgttt gaaccccatg   1320
catcaactct tgaggcattt ccaaaaagat gcaaaagtgc ttttccaaaa ttggggaatt   1380
gaacccatcg acaatgtaat ggggatgatt ggaatattgc ctgacatgac cccaagcacc   1440
gagatgtcat tgagaggagt gagagtcagc aaaatgggag tggatgagta ctccagcact   1500
gagagagtgg tggtgagcat tgaccgtttt ttaagagttc gggatcaaag gggaaacata   1560
ctactgtccc ctgaagaagt cagtgaaaca caaggaacgg aaaagctgac aataatttat   1620
tcgtcatcaa tgatgtggga gattaatggt cccgaatcag tgttggtcaa tacttatcaa   1680
tggatcatca ggaactggga aattgtaaaa attcagtggt cacaggaccc cacaatgtta   1740
tacaataaga tagaatttga gccattccaa tccctggtcc ctagggccac cagaagccaa   1800
tacagcggtt tcgtaagaac cctgtttcag caaatgcgag atgtacttgg aacatttgat   1860
actgctcaaa taataaaact cctccctttt gccgctgctc ctccggaaca gagtaggatg   1920
cagttctctt ctttgactgt taatgtaaga ggttcgggaa tgaggatact tgtaagaggc   1980
aattccccag tgttcaacta caataaagcc actaaaaggc tcacagtcct cggaaaggat   2040
gcaggtgcgc ttactgagga cccagatgaa ggtacggctg gagtagaatc tgctgttcta   2100
agagggtttc tcattttagg taaagaaaac aagagatatg gcccagcact aagcatcaat   2160
gaactaagca aacttgcaaa aggggagaaa gccaatgtac taattgggca aggggacgta   2220
gtgttggtaa tgaaacggaa acgtgactct agcatactta ctgacagcca gacagcgacc   2280
aaaaggattc ggatggccat caattagtgt tgaattgttt aaaaacgacc ttgtttctac   2340
t                                                                   2341
```

<210> SEQ ID NO 2
<211> LENGTH: 759
<212> TYPE: PRT
<213> ORGANISM: Artificial Sequence
<220> FEATURE:
<223> OTHER INFORMATION: Chemically synthesized - mutant PB2 based on
      A/equine/Ohio/1/2003 H3N8 EIV

<400> SEQUENCE: 2

```
Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95
```

```
Thr Trp Trp Asn Arg Asn Gly Pro Thr Thr Ser Thr Ile His Tyr Pro
            100                 105                 110
Lys Val Tyr Lys Thr Tyr Phe Glu Lys Val Glu Arg Leu Lys His Gly
            115                 120                 125
Thr Phe Gly Pro Val His Phe Arg Asn Gln Val Lys Ile Arg Arg Arg
    130                 135                 140
Val Asp Val Asn Pro Gly His Ala Asp Leu Ser Ala Lys Glu Ala Gln
145                 150                 155                 160
Asp Val Ile Met Glu Val Val Phe Pro Asn Glu Val Gly Ala Arg Ile
                165                 170                 175
Leu Thr Ser Glu Ser Gln Leu Thr Ile Thr Lys Glu Lys Lys Glu Glu
            180                 185                 190
Leu Gln Asp Cys Lys Ile Ala Pro Leu Met Val Ala Tyr Met Leu Glu
            195                 200                 205
Arg Glu Leu Val Arg Lys Thr Arg Phe Leu Pro Val Ala Gly Gly Thr
    210                 215                 220
Ser Ser Val Tyr Ile Glu Val Leu His Leu Thr Gln Gly Thr Cys Trp
225                 230                 235                 240
Glu Gln Met Tyr Thr Pro Gly Gly Glu Val Arg Asn Asp Asp Ile Asp
                245                 250                 255
Gln Ser Leu Ile Ile Ala Ala Arg Ser Ile Val Arg Arg Ala Thr Val
            260                 265                 270
Ser Ala Asp Pro Leu Ala Ser Leu Leu Glu Met Cys His Ser Thr Gln
    275                 280                 285
Ile Gly Gly Ile Arg Met Val Asp Ile Leu Lys Gln Asn Pro Thr Glu
290                 295                 300
Glu Gln Ala Val Asp Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
                325                 330                 335
Ser Val Lys Arg Glu Glu Met Leu Thr Gly Asn Leu Gln Thr Leu
            340                 345                 350
Lys Ile Arg Met His Glu Gly Tyr Glu Glu Phe Thr Met Val Gly Arg
            355                 360                 365
Arg Ala Thr Ala Ile Leu Arg Lys Ala Thr Arg Leu Ile Gln Leu
    370                 375                 380
Ile Val Ser Gly Arg Asp Glu Gln Ser Ile Ala Glu Ala Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
            435                 440                 445
Trp Gly Ile Glu Pro Ile Asp Asn Val Met Gly Met Ile Gly Ile Leu
    450                 455                 460
Pro Asp Met Thr Pro Ser Thr Glu Met Ser Leu Arg Gly Val Arg Val
465                 470                 475                 480
Ser Lys Met Gly Val Asp Glu Tyr Ser Ser Thr Glu Arg Val Val
                485                 490                 495
Ser Ile Asp Arg Phe Leu Arg Val Arg Asp Gln Arg Gly Asn Ile Leu
            500                 505                 510
```

| Leu | Ser | Pro | Glu | Glu | Val | Ser | Glu | Thr | Gln | Gly | Thr | Glu | Lys | Leu | Thr |
| | | 515 | | | | 520 | | | | | 525 | | | | |

| Ile | Ile | Tyr | Ser | Ser | Ser | Met | Met | Trp | Glu | Ile | Asn | Gly | Pro | Glu | Ser |
| 530 | | | | | 535 | | | | | 540 | | | | | |

| Val | Leu | Val | Asn | Thr | Tyr | Gln | Trp | Ile | Ile | Arg | Asn | Trp | Glu | Ile | Val |
| 545 | | | | 550 | | | | | 555 | | | | | 560 | |

| Lys | Ile | Gln | Trp | Ser | Gln | Asp | Pro | Thr | Met | Leu | Tyr | Asn | Lys | Ile | Glu |
| | | | | 565 | | | | 570 | | | | | 575 | | |

| Phe | Glu | Pro | Phe | Gln | Ser | Leu | Val | Pro | Arg | Ala | Thr | Arg | Ser | Gln | Tyr |
| | | | | 580 | | | | | 585 | | | | | 590 | |

| Ser | Gly | Phe | Val | Arg | Thr | Leu | Phe | Gln | Gln | Met | Arg | Asp | Val | Leu | Gly |
| | | 595 | | | | | 600 | | | | | 605 | | | |

| Thr | Phe | Asp | Thr | Ala | Gln | Ile | Ile | Lys | Leu | Leu | Pro | Phe | Ala | Ala | Ala |
| | | 610 | | | | | 615 | | | | | 620 | | | |

| Pro | Pro | Glu | Gln | Ser | Arg | Met | Gln | Phe | Ser | Ser | Leu | Thr | Val | Asn | Val |
| 625 | | | | | 630 | | | | | 635 | | | | | 640 |

| Arg | Gly | Ser | Gly | Met | Arg | Ile | Leu | Val | Arg | Gly | Asn | Ser | Pro | Val | Phe |
| | | | | 645 | | | | | 650 | | | | | 655 | |

| Asn | Tyr | Asn | Lys | Ala | Thr | Lys | Arg | Leu | Thr | Val | Leu | Gly | Lys | Asp | Ala |
| | | | 660 | | | | | 665 | | | | | 670 | | |

| Gly | Ala | Leu | Thr | Glu | Asp | Pro | Asp | Glu | Gly | Thr | Ala | Gly | Val | Glu | Ser |
| | | 675 | | | | | 680 | | | | | 685 | | | |

| Ala | Val | Leu | Arg | Gly | Phe | Leu | Ile | Leu | Gly | Lys | Glu | Asn | Lys | Arg | Tyr |
| | | 690 | | | | | 695 | | | | | 700 | | | |

| Gly | Pro | Ala | Leu | Ser | Ile | Asn | Glu | Leu | Ser | Lys | Leu | Ala | Lys | Gly | Glu |
| 705 | | | | | 710 | | | | | 715 | | | | | 720 |

| Lys | Ala | Asn | Val | Leu | Ile | Gly | Gln | Gly | Asp | Val | Val | Leu | Val | Met | Lys |
| | | | | 725 | | | | | 730 | | | | | 735 | |

| Arg | Lys | Arg | Asp | Ser | Ser | Ile | Leu | Thr | Asp | Ser | Gln | Thr | Ala | Thr | Lys |
| | | | 740 | | | | | 745 | | | | | 750 | | |

| Arg | Ile | Arg | Met | Ala | Ile | Asn |
| | | 755 | | | | |

```
<210> SEQ ID NO 3
<211> LENGTH: 2341
<212> TYPE: DNA
<213> ORGANISM: Artificial Sequence
<220> FEATURE:
<223> OTHER INFORMATION: Chemically synthesized - mutant segment 2 based
      on A/equine/Ohio/1/2003 H3N8 EIV

<400> SEQUENCE: 3
agcgaaagca ggcaaaccat ttgaatggat gtcaatccga ctctactttt cttaaaggtg      60
ccagcgcaaa atgctataag cacaacattc ccttatactg gagatcctcc ctacagtcat     120
ggaacaggga caggatacac catggatact gtcaacagaa cacaccaata ttcagaaaaa     180
gggaaatgga acaaacac tgagattgga gcaccacaac ttaatccaat cgatggacca     240
cttcctgaag acaatgaacc aagtgggtac gcccaaacag attgtgtatt ggaagcaatg     300
gctttccttg aagaatccca tcccggaatc tttgaaaatt cgtgtcttga acgatggag     360 gtgattcagc agacaagagt ggacaaacta acacaaggcc gacaaactta tgattggacc     420 ttgaataggaa atcaacctgc cgcaacagca cttgctaata cgattgaagt attcagatca     480
aatggtctga cttccaatga atcggggaga ttgatggact ccctcaaaga tgtcatggag     540
tccatgaaca aggaagaaat ggaaataaca acacacttcc aacggaagag aagagtaaga     600
```

| | | |
|---|---|---|
| gacaacatga caaagagaat ggtaacacag agaaccatag ggaagaagaa acaacgatta | 660 | |
| aacagaaaga gctatctaat cagaacatta accctaaaca caatgaccaa ggacgctgag | 720 | |
| agagggaaat tgaaacgacg agcaatcgct accccaggga tgcagataag agggtttgta | 780 | |
| tattttgttg aaacactagc ccgaagaata tgtgaaaagc ttgaacaatc aggattgcca | 840 | |
| gttggcggta atgagaaaaa ggccaaactg gctaatgtcg tcagaaaaat gatgactaat | 900 | |
| tcccaagaca ctgaactctc cttcaccatc actggggaca taccaaatg gaatgaaaat | 960 | |
| cagaacccac gcatattcct ggcaatgatc acatacataa ctagaaacca gccagaatgg | 1020 | |
| ttcagaaatg ttctaagcat tgcaccgatt atgttctcaa ataaaatggc aagactgggg | 1080 | |
| aaaggatata tgtttgaaag caaaagtatg aaattgagaa ctcaaatacc agcagaaatg | 1140 | |
| ctagcaagca ttgacctgaa atatttcaat gattcaacaa aaagaaaat tgaagaaata | 1200 | |
| aggcctcttc tggttgacgg gactgcttca ctgagtcctg gcatgatgat gggaatgttc | 1260 | |
| aacatgttga gcactgtgct gggtgtatcc atattaaacc tgggccagag gaaatacaca | 1320 | |
| aagaccacat actggtggga tggtctgcaa tcatccgatg actttgcttt gatagtgaat | 1380 | |
| gcgcctaatc atgaaggaat acaagctgga gtagacagat tctatagaac ttgcaaactg | 1440 | |
| gtcgggatca acatgagcaa aaagaagtcc tacataaata gaactggaac attcgaattc | 1500 | |
| acaagctttt tctaccggta tggtttttgta gccaatttca gcatggaact acccagtttt | 1560 | |
| ggggtttccg gaataaatga atctgcagac atgagcattg gagtgacagt catcaaaaac | 1620 | |
| aacatgataa ataatgatct cggtcctgcc acggcacaaa tggcactcca actcttcatt | 1680 | |
| aaggattatc ggtacacata ccggtgccat agaggtgata cccagataca aaccagaaga | 1740 | |
| tcttttgagt tgaagaagct ttgggggcag actcgatcaa agactggtct actggtatca | 1800 | |
| gatggggtc caaacctata taacatcaga aacctacaca tcccggaagt ctgtttaaaa | 1860 | |
| tgggagctaa tggatgaaga ttataagggg aggctatgca atccattgaa tcctttcgtt | 1920 | |
| agtcacaaag aaattgaatc agtcaacagt gcagtagtaa tgtctgcgca tggccctgcc | 1980 | |
| aaaagcatgg agtatgatgc tgttactaca acacattctt ggataccaa gaggaaccgg | 2040 | |
| tccatattga acacaagcca aagggaata ctcgaagatg agcagatgta tcagaaatgc | 2100 | |
| tgcaacctgt ttgaaaaatt cttccccagc agctcataca aagaccagt cggaatttct | 2160 | |
| agtatggttg aggccatggt gtccagggcc cgcattgatg cacgaattga cttcgaatct | 2220 | |
| ggacggataa agaaggatga gttcgctgag atcatgaaga tctgttccac cattgaagag | 2280 | |
| ctcagacggc aaaaatagtg aatttagctt gatcttcatg aaaaaatgcc ttgtttctac | 2340 | |
| t | 2341 | |

<210> SEQ ID NO 4
<211> LENGTH: 757
<212> TYPE: PRT
<213> ORGANISM: Artificial Sequence
<220> FEATURE:
<223> OTHER INFORMATION: Chemically synthesized - mutant PB1 based on
    A/equine/Ohio/1/2003 H3N8 EIV

<400> SEQUENCE: 4

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

```
Tyr Ser Glu Lys Gly Lys Trp Thr Thr Asn Thr Glu Ile Gly Ala Pro
     50                  55                  60

Gln Leu Asn Pro Ile Asp Gly Pro Leu Pro Glu Asp Asn Glu Pro Ser
 65              70                  75                      80

Gly Tyr Ala Gln Thr Asp Cys Val Leu Glu Ala Met Ala Phe Leu Glu
                 85                  90                  95

Glu Ser His Pro Gly Ile Phe Glu Asn Ser Cys Leu Glu Thr Met Glu
                100                 105                 110

Val Ile Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
        130                 135                 140

Asn Thr Ile Glu Val Phe Arg Ser Asn Gly Leu Thr Ser Asn Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
            195                 200                 205

Lys Gln Arg Leu Asn Arg Lys Ser Tyr Leu Ile Arg Thr Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Glu Ile Arg Pro Leu Leu Val Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460
```

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
            485                 490                 495

Tyr Arg Tyr Gly Phe Val Ala Asn Phe Ser Met Glu Leu Pro Ser Phe
        500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
        530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
            565                 570                 575

Lys Lys Leu Trp Gly Gln Thr Arg Ser Lys Thr Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
        610                 615                 620

Cys Asn Pro Leu Asn Pro Phe Val Ser His Lys Glu Ile Glu Ser Val
625                 630                 635                 640

Asn Ser Ala Val Val Met Ser Ala His Gly Pro Ala Lys Ser Met Glu
            645                 650                 655

Tyr Asp Ala Val Thr Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
            725                 730                 735

Lys Asp Glu Phe Ala Glu Ile Met Lys Ile Cys Ser Thr Ile Glu Glu
        740                 745                 750

Leu Arg Arg Gln Lys
        755

<210> SEQ ID NO 5
<211> LENGTH: 2341
<212> TYPE: DNA
<213> ORGANISM: Influenza A virus

<400> SEQUENCE: 5
agcgaaagca ggtcaaatat attcaatatg gagagaataa agaactgag agatctgatg      60 ttacaatccc gcacccgcga gatactaaca aaaactactg tggaccacat ggccataatc     120
aagaaataca catcaggaag acaagagaag aaccctgcac ttaggatgaa atggatgatg     180
gcaatgaaat acccaatcac ggcagataag aggataatgg agatgattcc tgagagaaat     240
gaacagggac aaacccttg gagcaaaacg aacgatgctg gctcagaccg cgtaatggta     300
tcacctctgg cagtgacatg gtggaatagg aatggaccaa caacaagcac aattcattat     360
ccaaaagtct acaaaactta ttttgaaaag gttgaaagat gaaacacgg aacctttggc     420

-continued

```
cccgttcatt ttaggaatca agtcaagata agacgaagag ttgatgtaaa ccctggtcac    480
gcggacctca gtgccaaaga agcacaagat gtgatcatgg aagttgtttt cccaaatgaa    540
gtgggagcca gaattctaac atcggaatca caactaacaa taaccaaaga gaaaaaggaa    600
gaacttcagg actgcaaaat tgctcccttg atggtagcat acatgctaga aagagagttg    660
gtccgaaaaa caaggttcct cccagtagca ggcggaacaa gcagtgtata cattgaagtg    720
ttgcatctga ctcagggaac atgctgggag caaatgtaca ccccaggagg agaagttaga    780
aacgatgata ttgatcaaag tttaattatt gcagcacgga acatagtgag aagagcaaca    840
gtatcagcag atccactagc atccctactg gaaatgtgcc acagtacaca gattggtgga    900
ataaggatgg tagacatcct taagcagaat ccaacagagg aacaagctgt ggatatatgc    960
aaagcagcaa tgggattgag aattagctca tcattcagct ttggtggatt caccttcaaa   1020
agaacaagtg gatcatcagt caagagagaa gaagaaatgc ttacgggcaa ccttcaaaca   1080
ttgaaaataa gaatgcatga gggctatgaa gaattcacaa tggtcggaag aagagcaaca   1140
gctattctca gaaaggcaac cagaagattg attcaattga tagtaagtgg gagagatgaa   1200
caatcaattg ctgaagcaat aattgtagcc atggtgtttt cgcaagaaga ttgcatgata   1260
aaagcagttc gaggcgattt gaactttgtt aatagagcaa atcagcgttt gaaccccatg   1320
catcaactct tgaggcattt ccaaaaagat gcaaaagtgc ttttccaaaa ttggggaatt   1380
gaacccatcg acaatgtaat ggggatgatt ggaatattgc ctgacatgac ccccaagcacc   1440 gagatgtcat tgagaggagt gagagtcagc aaaatgggag tggatgagta ctccagcact   1500
gagagagtgg tggtgagcat tgaccgtttt ttaagagttc gggatcaaag ggaaaacata   1560
ctactgtccc ctgaagaagt cagtgaaaca caaggaacgg aaaagctgac aataatttat   1620
tcgtcatcaa tgatgtggga gattaatggt cccgaatcag tgttggtcaa tacttatcaa   1680
tggatcatca ggaactggga aattgtaaaa attcagtggt cacaggaccc cacaatgtta   1740
tacaataaga tagaatttga gccattccaa tccctggtcc ctagggccac cagaagccaa   1800
tacagcggtt tcgtaagaac cctgtttcag caaatgcgag atgtacttgg aacatttgat   1860
actgctcaaa taataaaact cctccctttt gccgctgctc ctccggaaca gagtaggatg   1920
cagttctctt ctttgactgt taatgtaaga ggttcgggaa tgaggatact tgtaagaggc   1980
aattccccag tgttcaacta caataaagcc actaaaaggc tcacagtcct cggaaaggat   2040
gcaggtgcgc ttactgagga cccagatgaa ggtacggctg gagtagaatc tgctgttcta   2100
agagggtttc tcattttagg taaagaaaac aagagatatg gcccagcact aagcatcaat   2160
gaactaagca aacttgcaaa aggggagaaa gccaatgtac taattgggca aggggacgta   2220
gtgttggtaa tgaaacggaa acgtgactct agcatactta ctgacagcca gacagcgacc   2280
aaaaggattc ggatggccat caattagtgt tgaattgttt aaaaacgacc ttgtttctac   2340
t                                                                  2341
```

```
<210> SEQ ID NO 6
<211> LENGTH: 759
<212> TYPE: PRT
<213> ORGANISM: Influenza A virus

<400> SEQUENCE: 6

Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
            20                  25                  30
```

```
Lys Tyr Thr Ser Gly Arg Gln Glu Lys Asn Pro Ala Leu Arg Met Lys
             35                  40                  45

Trp Met Met Ala Met Lys Tyr Pro Ile Thr Ala Asp Lys Arg Ile Met
 50                  55                  60

Glu Met Ile Pro Glu Arg Asn Glu Gln Gly Gln Thr Leu Trp Ser Lys
 65                  70                  75                  80

Thr Asn Asp Ala Gly Ser Asp Arg Val Met Val Ser Pro Leu Ala Val
                 85                  90                  95

Thr Trp Trp Asn Arg Asn Gly Pro Thr Thr Ser Thr Ile His Tyr Pro
                100                 105                 110

Lys Val Tyr Lys Thr Tyr Phe Glu Lys Val Glu Arg Leu Lys His Gly
             115                 120                 125

Thr Phe Gly Pro Val His Phe Arg Asn Gln Val Lys Ile Arg Arg Arg
         130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                 165                 170                 175

Leu Thr Ser Glu Ser Gln Leu Thr Ile Thr Lys Glu Lys Lys Glu Glu
             180                 185                 190

Leu Gln Asp Cys Lys Ile Ala Pro Leu Met Val Ala Tyr Met Leu Glu
         195                 200                 205

Arg Glu Leu Val Arg Lys Thr Arg Phe Leu Pro Val Ala Gly Gly Thr
     210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                 245                 250                 255

Gln Ser Leu Ile Ile Ala Ala Arg Asn Ile Val Arg Arg Ala Thr Val
             260                 265                 270

Ser Ala Asp Pro Leu Ala Ser Leu Leu Glu Met Cys His Ser Thr Gln
         275                 280                 285

Ile Gly Gly Ile Arg Met Val Asp Ile Leu Lys Gln Asn Pro Thr Glu
     290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                 325                 330                 335

Ser Val Lys Arg Glu Glu Glu Met Leu Thr Gly Asn Leu Gln Thr Leu
             340                 345                 350

Lys Ile Arg Met His Glu Gly Tyr Glu Glu Phe Thr Met Val Gly Arg
         355                 360                 365

Arg Ala Thr Ala Ile Leu Arg Lys Ala Thr Arg Arg Leu Ile Gln Leu
     370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                 405                 410                 415

Asp Leu Asn Phe Val Asn Arg Ala Asn Gln Arg Leu Asn Pro Met His
             420                 425                 430

Gln Leu Leu Arg His Phe Gln Lys Asp Ala Lys Val Leu Phe Gln Asn
         435                 440                 445
```

```
Trp Gly Ile Glu Pro Ile Asp Asn Val Met Gly Met Ile Gly Ile Leu
        450                 455                 460
Pro Asp Met Thr Pro Ser Thr Glu Met Ser Leu Arg Gly Val Arg Val
465                 470                 475                 480
Ser Lys Met Gly Val Asp Glu Tyr Ser Ser Thr Glu Arg Val Val
                485                 490                 495
Ser Ile Asp Arg Phe Leu Arg Val Arg Asp Gln Arg Gly Asn Ile Leu
                500                 505                 510
Leu Ser Pro Glu Glu Val Ser Glu Thr Gln Gly Thr Glu Lys Leu Thr
            515                 520                 525
Ile Ile Tyr Ser Ser Ser Met Met Trp Glu Ile Asn Gly Pro Glu Ser
530                 535                 540
Val Leu Val Asn Thr Tyr Gln Trp Ile Ile Arg Asn Trp Glu Ile Val
545                 550                 555                 560
Lys Ile Gln Trp Ser Gln Asp Pro Thr Met Leu Tyr Asn Lys Ile Glu
                565                 570                 575
Phe Glu Pro Phe Gln Ser Leu Val Pro Arg Ala Thr Arg Ser Gln Tyr
                580                 585                 590
Ser Gly Phe Val Arg Thr Leu Phe Gln Gln Met Arg Asp Val Leu Gly
            595                 600                 605
Thr Phe Asp Thr Ala Gln Ile Ile Lys Leu Leu Pro Phe Ala Ala Ala
        610                 615                 620
Pro Pro Glu Gln Ser Arg Met Gln Phe Ser Ser Leu Thr Val Asn Val
625                 630                 635                 640
Arg Gly Ser Gly Met Arg Ile Leu Val Arg Gly Asn Ser Pro Val Phe
                645                 650                 655
Asn Tyr Asn Lys Ala Thr Lys Arg Leu Thr Val Leu Gly Lys Asp Ala
                660                 665                 670
Gly Ala Leu Thr Glu Asp Pro Asp Glu Gly Thr Ala Gly Val Glu Ser
            675                 680                 685
Ala Val Leu Arg Gly Phe Leu Ile Leu Gly Lys Glu Asn Lys Arg Tyr
        690                 695                 700
Gly Pro Ala Leu Ser Ile Asn Glu Leu Ser Lys Leu Ala Lys Gly Glu
705                 710                 715                 720
Lys Ala Asn Val Leu Ile Gly Gln Gly Asp Val Val Leu Val Met Lys
                725                 730                 735
Arg Lys Arg Asp Ser Ser Ile Leu Thr Asp Ser Gln Thr Ala Thr Lys
                740                 745                 750
Arg Ile Arg Met Ala Ile Asn
        755
```

<210> SEQ ID NO 7
<211> LENGTH: 2341
<212> TYPE: DNA
<213> ORGANISM: Influenza A virus

<400> SEQUENCE: 7

```
agcgaaagca ggcaaaccat ttgaatggat gtcaatccga ctctactttt cttaaaggtg    60
ccagcgcaaa atgctataag cacaacattc ccttatactg gagatcctcc ctacagtcat   120
ggaacaggga caggatacac catggatact gtcaacagaa cacaccaata ttcagaaaaa   180
gggaaatgga caacaaacac tgagattgga gcaccacaac ttaatccaat cgatggacca   240
cttcctgaag acaatgaacc aagtgggtac gcccaaacag attgtgtatt ggaagcaatg   300
gctttccttg aagaatccca tcccggaatc tttgaaaatt cgtgtcttga aacgatggag   360
```

```
gtgattcagc agacaagagt ggacaaacta acacaaggcc gacaaactta tgattggacc      420
ttgaatagga atcaacctgc cgcaacagca cttgctaata cgattgaagt attcagatca      480
aatggtctga cttccaatga atcggggaga ttgatggact cctcaaaga tgtcatggag      540 tccatgaaca aggaagaaat ggaataaca acacacttcc aacggaagag aagagtaaga      600
gacaacatga caaagagaat ggtaacacag agaaccatag ggaagaagaa acaacgatta      660
aacgaaaaga gctatctaat cagaacatta accctaaaca caatgaccaa ggacgctgag      720
agagggaaat tgaaacgacg agcaatcgct accccaggga tgcagataag agggtttgta      780
tattttgttg aaacactagc ccgaagaata tgtgaaaagc ttgaacaatc aggattgcca      840
gttggcggta atgagaaaaa ggccaaactg ctaatgtcg tcagaaaaat gatgactaat      900
tcccaagaca ctgaactctc cttcaccatc actggggaca taccaaatg gaatgaaaat      960 cagaacccac gcatattcct ggcaatgatc acatacataa ctagaaacca gccagaatgg     1020
ttcagaaatg ttctaagcat tgcaccgatt atgttctcaa ataaaatggc aagactgggg     1080
aaaggatata tgtttgaaag caaaagtatg aaattgagaa ctcaaatacc agcagaaatg     1140
ctagcaagca ttgacctgaa atatttcaat gattcaacaa aaagaaaat tgaaaagata     1200 cgaccacttc tggttgacgg gactgcttca ctgagtcctg gcatgatgat gggaatgttc     1260
aacatgttga gcactgtgct gggtgtatcc atattaaacc tgggccagag gaaatacaca     1320
aagaccacat actggtggga tggtctgcaa tcatccgatg actttgcttt gatagtgaat     1380
gcgcctaatc atgaaggaat acaagctgga gtagacagat tctatagaac ttgcaaactg     1440
gtcgggatca acatgagcaa aaagaagtcc tacataaata gaactggaac attcgaattc     1500
acaagctttt tctaccggta tggttttgta gccaatttca gcatggaact acccagtttt     1560
ggggtttccg gaataaatga atctgcagac atgagcattg gagtgacagt catcaaaaac     1620
aacatgataa ataatgatct cggtcctgcc acggcacaaa tggcactcca actcttcatt     1680
aaggattatc ggtacacata ccggtgccat agaggtgata cccagataca aaccagaaga     1740
tcttttgagt tgaagaaact gtgggaacag actcgatcaa agactggtct actggtatca     1800
gatgggggtc aaacctata taacatcaga aacctacaca tcccgaagt ctgtttaaaa     1860 tgggagctaa tggatgaaga ttataagggg aggctatgca atccattgaa tcctttcgtt     1920
agtcacaaag aaattgaatc agtcaacagt gcagtagtaa tgtctgcgca tggccctgcc     1980
aaaagcatgg agtatgatgc tgttgcaaca acacattctt ggatcccaa gaggaaccgg     2040 tccatattga acacaagcca aggggaata ctcgaagatg agcagatgta tcagaaatgc     2100
tgcaacctgt ttgaaaaatt cttccccagc agctcataca gaagaccagt cggaatttct     2160
agtatggttg aggccatggt gtccagggcc cgcattgatg cacgaattga cttcgaatct     2220
ggacggataa agaaggatga gttcgctgag atcatgaaga tctgttccac cattgaagag     2280
ctcagacggc aaaaatagtg aatttagctt gatcttcatg aaaaaatgcc ttgtttctac     2340
t                                                                    2341
```

<210> SEQ ID NO 8
<211> LENGTH: 757
<212> TYPE: PRT
<213> ORGANISM: Influenza A virus

<400> SEQUENCE: 8

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Tyr Ser His
            20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Ile Gly Ala Pro
 50                  55                  60

Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
            85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Gly Leu Thr Ser Asn Glu Ser
145                 150                 155                 160

Gly Arg Leu Met Asp Phe Leu Lys Asp Val Met Glu Ser Met Asn Lys
            165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
            195                 200                 205

Lys Gln Arg Leu Asn Arg Lys Ser Tyr Leu Ile Arg Thr Leu Thr Leu
            210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
            245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Ile Thr Gly
            290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
            325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
            355                 360                 365

Pro Ala Glu Met Leu Ala Ser Ile Asp Leu Lys Tyr Phe Asn Asp Ser
            370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Gly Met Phe Asn Met Leu Ser
            405                 410                 415

Thr Val Leu Gly Val Ser Ile Leu Asn Leu Gly Gln Arg Lys Tyr Thr
            420                 425                 430

```
Lys Thr Thr Tyr Trp Trp Asp Gly Leu Gln Ser Ser Asp Phe Ala
            435                 440                 445

Leu Ile Val Asn Ala Pro Asn His Glu Gly Ile Gln Ala Gly Val Asp
450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Thr Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Lys Gly Arg Leu
            610                 615                 620

Cys Asn Pro Leu Asn Pro Phe Val Ser His Lys Glu Ile Glu Ser Val
625                 630                 635                 640

Asn Ser Ala Val Val Met Ser Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
            675                 680                 685

Tyr Gln Lys Cys Cys Asn Leu Phe Glu Lys Phe Phe Pro Ser Ser Ser
690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
            740                 745                 750

Leu Arg Arg Gln Lys
        755

<210> SEQ ID NO 9
<211> LENGTH: 2233
<212> TYPE: DNA
<213> ORGANISM: Influenza A virus

<400> SEQUENCE: 9
agcgaaagca ggtactgatc caaaatggaa gactttgtgc gacagtgctt caatccaatg      60
atcgtcgagc ttgcggaaaa ggcaatgaaa gaatatggag aggacccgaa atcgaaaaca     120
aacaaatttg cagcaatatg cactcacttg gaagtctgct tcatgtactc ggatttccac     180
tttattaatg aactgggtga gtcagtggtc atagagtctg tgacccaaa tgctctttg      240
```

```
aaacacagat tgaaatcat tgaggggaga gatcgaacaa tggcatggac agtagtaaac    300
agcatctgca acaccacaag agctgaaaaa cctaaatttc ttccagattt atacgactat    360
aaggagaaca gatttgttga aattggtgtg acaaggagag aagttcacat atactacctg    420
gagaaggcca acaaaataaa gtctgagaaa acacatatcc acattttctc atttacagga    480
gaggaaatgg ctacaaaagc ggactatact cttgatgaag agagtagagc caggatcaag    540
accagactat tcactataag acaagaaatg gccagtagag gcctctggga ttcctttcgt    600
cagtccgaga gaggcgaaga gacaattgaa gaaagatttg aaatcacagg gacgatgcgc    660
aagcttgcca attacagtct cccaccgaac ttctccagcc ttgaaaattt tagagtctat    720
gtggatggat tcgaaccgaa cggcttcatt gagagtaagc tttctcaaat gtccaaagaa    780
gtaaatgcca gaatcgaacc atttttcaaag caacacccc gaccactcaa aatgccaggt    840
ggtccaccct gccatcagcg atctaaattc ttgctaatgg atgctctgaa actgagcatt    900
gaggacccaa gtcacgaggg agagggaata ccactatatg atgcaatcaa atgcatgaaa    960
actttctttg gatggaaaga gcccagtatt gttaaaccac atgaaaaggg tataaacccg   1020
aactatctcc aaacttggaa gcaagtatta agagaaatac aagaccttga gaacgaagaa   1080
aggaccccca gaccaagaa tatgaaaaaa acaagccaat gaaatgggc actaggtgaa   1140
aatatggcac agagaaagt ggattttgag gattgtaaag acatcagtga tttaaaacag   1200
tatgacagtg atgagccaga aacaaggtct cttgcaagtt ggattcaaag tgagttcaac   1260
aaagcttgtg agctgacaga ttcaagctgg atagagctcg atgaaattgg ggaggatgtc   1320
gccccaatag aatacattgc gagcatgagg agaaattatt ttactgctga gatttcccat   1380
tgtagagcaa cagaatatat aatgaaagga gtgtacatca acactgctct actcaatgca   1440
tcctgtgctg cgatggatga atttcaatta attccgatga taagtaaatg caggaccaaa   1500
gaagggagaa ggaaaacaaa tttatatgga ttcataataa agggaagatc ccatttaaga   1560
aatgatactg acgtggtgaa ctttgtaagt atggaatttt ctctcactga tccaagattt   1620
gagccacaca aatgggaaaa atactgcgtt ctagaaattg agacatgct tctaagaact   1680
gctgtaggtc aagtgtcaag acccatgttt tgtatgtaa ggacaaatgg aacctctaaa   1740
attaaaatga atggggaat ggaaatgagg cgctgcctcc ttcagtctct gcaacagatt   1800
gaaagcatga tcgaagctga gtcctcggtc aaagaaaagg acatgaccaa gaatttttt   1860
gagaacaaat cagagacatg gccatagga gagtccccca aaggagtgga agagggctca   1920
atcgggaagg tttgcaggac cttattagca aaatctgtgt ttaacagttt gtatgcatct   1980
ccacaactgg aagggttttc agctgaatct aggaaattac ttctcattgt tcaggctctt   2040
agggataacc tggaacctgg aacatttgat attggggggt tatatgaatc aattgaggag   2100
tgcctgatta atgatccctg ggttttgctt aatgcatctt ggttcaactc cttccttaca   2160
catgcactga gtagttgtg gcaatgctac tatttgctat ccatactgtc caaaaaagta   2220
ccttgtttct act                                                     2233
```

<210> SEQ ID NO 10
<211> LENGTH: 716
<212> TYPE: PRT
<213> ORGANISM: Influenza A virus

<400> SEQUENCE: 10

```
Met Glu Asp Phe Val Arg Gln Cys Phe Asn Pro Met Ile Val Glu Leu
1               5                   10                  15
```

```
Ala Glu Lys Ala Met Lys Glu Tyr Gly Asp Pro Lys Ile Glu Thr
            20                  25                  30

Asn Lys Phe Ala Ala Ile Cys Thr His Leu Glu Val Cys Phe Met Tyr
            35                  40                  45

Ser Asp Phe His Phe Ile Asn Glu Leu Gly Glu Ser Val Val Ile Glu
50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
            115                 120                 125

Ile Tyr Tyr Leu Glu Lys Ala Asn Lys Ile Lys Ser Glu Lys Thr His
            130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
            195                 200                 205

Gly Thr Met Arg Lys Leu Ala Asn Tyr Ser Leu Pro Pro Asn Phe Ser
210                 215                 220

Ser Leu Glu Asn Phe Arg Val Tyr Val Asp Gly Phe Glu Pro Asn Gly
225                 230                 235                 240

Phe Ile Glu Ser Lys Leu Ser Gln Met Ser Lys Glu Val Asn Ala Arg
                245                 250                 255

Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
            275                 280                 285

Lys Leu Ser Ile Glu Asp Pro Ser His Glu Gly Glu Gly Ile Pro Leu
290                 295                 300

Tyr Asp Ala Ile Lys Cys Met Lys Thr Phe Phe Gly Trp Lys Glu Pro
305                 310                 315                 320

Ser Ile Val Lys Pro His Glu Lys Gly Ile Asn Pro Asn Tyr Leu Gln
                325                 330                 335

Thr Trp Lys Gln Val Leu Glu Glu Ile Gln Asp Leu Glu Asn Glu Glu
            340                 345                 350

Arg Thr Pro Lys Thr Lys Asn Met Lys Lys Thr Ser Gln Leu Lys Trp
            355                 360                 365

Ala Leu Gly Glu Asn Met Ala Pro Glu Lys Val Asp Phe Glu Asp Cys
            370                 375                 380

Lys Asp Ile Ser Asp Leu Lys Gln Tyr Asp Ser Asp Glu Pro Glu Thr
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu Tyr Ile Ala Ser Met Arg Arg Asn Tyr Phe Thr Ala
```

435                 440                 445
Glu Ile Ser His Cys Arg Ala Thr Glu Tyr Ile Met Lys Gly Val Tyr
    450                 455                 460
Ile Asn Thr Ala Leu Leu Asn Ala Ser Cys Ala Ala Met Asp Glu Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
Asp Pro Arg Phe Glu Pro His Lys Trp Glu Lys Tyr Cys Val Leu Glu
    530                 535                 540
Ile Gly Asp Met Leu Leu Arg Thr Ala Val Gly Gln Val Ser Arg Pro
545                 550                 555                 560
Met Phe Leu Tyr Val Arg Thr Asn Gly Thr Ser Lys Ile Lys Met Lys
                565                 570                 575
Trp Gly Met Glu Met Arg Arg Cys Leu Leu Gln Ser Leu Gln Gln Ile
            580                 585                 590
Glu Ser Met Ile Glu Ala Glu Ser Val Lys Glu Lys Asp Met Thr
        595                 600                 605
Lys Glu Phe Phe Glu Asn Lys Ser Glu Thr Trp Pro Ile Gly Glu Ser
    610                 615                 620
Pro Lys Gly Val Glu Glu Gly Ser Ile Gly Lys Val Cys Arg Thr Leu
625                 630                 635                 640
Leu Ala Lys Ser Val Phe Asn Ser Leu Tyr Ala Ser Pro Gln Leu Glu
                645                 650                 655
Gly Phe Ser Ala Glu Ser Arg Lys Leu Leu Leu Ile Val Gln Ala Leu
            660                 665                 670
Arg Asp Asn Leu Glu Pro Gly Thr Phe Asp Ile Gly Gly Leu Tyr Glu
        675                 680                 685
Ser Ile Glu Glu Cys Leu Ile Asn Asp Pro Trp Val Leu Leu Asn Ala
    690                 695                 700
Ser Trp Phe Asn Ser Phe Leu Thr His Ala Leu Lys
705                 710                 715

<210> SEQ ID NO 11
<211> LENGTH: 1762
<212> TYPE: DNA
<213> ORGANISM: Influenza A virus

<400> SEQUENCE: 11
agcaaaagca gggatatttt ctgtcaatca tgaagacaac cattattttg atactactga      60
cccattgggc ctacagtcaa aacccaatca gtggcaacaa cacagccaca ttgtgtctgg     120
gacgccatgc agtagcaaat ggaacattgg taaaaacaat aagtgatgat caaattgagg     180
tgacaaatgc tacagaatta gttcagagca tttcaacggg aaaatatgc aacaactcat     240 atagaattct agatggaaga aattgcacat taatagatgc aatgctagga gaccccccact     300 gtgacgcctt tcagtatgag aattgggacc tctttataga aagaagcagc gctttcagca     360
attgctaccc atatgacatc cctgactatg catcgctccg atccattgta gcatcctcag     420
gaacattgga attcacagca gagggattca catggacagg tgtcactcaa aacggaataa     480
gtggagcctg caaaaggggga tcagccgata gtttctttag ccgactgaat tggctaacaa     540

```
aatctggaag ctcttacccc acattgaatg tgacaatgcc taacaataaa aatttcgaca    600
agctatacat ctgggggatt catcacccga gctcaaatca agagcagaca aaattgtaca    660
tccaagaatc aggacgagta acagtctcaa caaaaagaag tcaacaaaca ataatcccta    720
acatcggatc tagaccgtgg gtcagaggtc aatcaggcag ataagcata tactggacca    780
ttgtaaaacc tggagatatc ctaatgataa acagtaatgg caacttagtt gcaccgcggg    840
gatattttaa attgaaaaca gggaaaagct ctgtaatgag atcagatgta cccatagaaa    900
tttgtgtgtc tgaatgtatt acaccaaatg gaagcatctc caacgacaag ccattccaaa    960
atgtgaacaa agttacatat ggaaaatgcc ccaagtatat caggcaaaac actttaaagc    1020
tggccactgg gatgaggaat gtaccagaaa agcaaatcag aggaatcttc ggagcaatag    1080
cgggattcat cgaaaacggc tgggaaggaa tggttgatgg gtggtatggg ttccgatatc    1140
aaaactctga aggaacaggg caagctgcag atctaaagag cactcaagca gccatcgacc    1200
agattaatgg aaagttaaac agagtgattg aaagaaccaa tgagaaattc catcaaatag    1260
agaaggaatt ctcagaagta gaaggaagaa ttcaggactt ggagaaatat gtagaagaca    1320
ccaaaataga cctatggtcc tacaatgcag aattgctggt ggctctagaa aatcaacata    1380
caattgactt aacagatgca gaaatgaata aattatttga aagactaga cgccagttaa    1440
gagaaaacgc agaagacatg ggaggtggat gtttcaagat ttaccacaaa tgtgataatg    1500
catgcattgg atcaataaga aatgggacat atgaccatta catatacaga gatgaagcat    1560
taaacaaccg atttcagatc aaaggtgtag agttgaaatc aggctacaaa gattggatac    1620
tgtggatttc attcgccata tcatgcttct taatttgcgt tgttctattg ggtttcatta    1680
tgtgggcttg ccaaaaaggc aacatcagat gcaacatttg catttgagta aactgatagt    1740
taaaaacacc cttgtttcta ct                                             1762
```

<210> SEQ ID NO 12
<211> LENGTH: 565
<212> TYPE: PRT
<213> ORGANISM: Influenza A virus

<400> SEQUENCE: 12

```
Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly Arg
            20                  25                  30

His Ala Val Ala Asn Gly Thr Leu Val Lys Thr Ile Ser Asp Asp Gln
        35                  40                  45

Ile Glu Val Thr Asn Ala Thr Glu Leu Val Gln Ser Ile Ser Thr Gly
    50                  55                  60

Lys Ile Cys Asn Asn Ser Tyr Arg Ile Leu Asp Gly Arg Asn Cys Thr
65                  70                  75                  80

Leu Ile Asp Ala Met Leu Gly Asp Pro His Cys Asp Ala Phe Gln Tyr
                85                  90                  95

Glu Asn Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Ile Ser Gly Ala Cys Lys Arg Gly Ser Ala Asp
145                 150                 155                 160
```

```
Ser Phe Phe Ser Arg Leu Asn Trp Leu Thr Lys Ser Gly Ser Ser Tyr
            165                 170                 175

Pro Thr Leu Asn Val Thr Met Pro Asn Asn Lys Asn Phe Asp Lys Leu
        180                 185                 190

Tyr Ile Trp Gly Ile His His Pro Ser Ser Asn Gln Glu Gln Thr Lys
    195                 200                 205

Leu Tyr Ile Gln Glu Ser Gly Arg Val Thr Val Ser Thr Lys Arg Ser
210                 215                 220

Gln Gln Thr Ile Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
            245                 250                 255

Ile Leu Met Ile Asn Ser Asn Gly Asn Leu Val Ala Pro Arg Gly Tyr
        260                 265                 270

Phe Lys Leu Lys Thr Gly Lys Ser Ser Val Met Arg Ser Asp Val Pro
    275                 280                 285

Ile Glu Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
            325                 330                 335

Asn Val Pro Glu Lys Gln Ile Arg Gly Ile Phe Gly Ala Ile Ala Gly
        340                 345                 350

Phe Ile Glu Asn Gly Trp Glu Gly Met Val Asp Gly Trp Tyr Gly Phe
    355                 360                 365

Arg Tyr Gln Asn Ser Glu Gly Thr Gly Gln Ala Ala Asp Leu Lys Ser
370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
            405                 410                 415

Val Glu Gly Arg Ile Gln Asp Leu Glu Lys Tyr Val Glu Asp Thr Lys
        420                 425                 430

Ile Asp Leu Trp Ser Tyr Asn Ala Glu Leu Leu Val Ala Leu Glu Asn
    435                 440                 445

Gln His Thr Ile Asp Leu Thr Asp Ala Glu Met Asn Lys Leu Phe Glu
450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Gly Ser Ile
            485                 490                 495

Arg Asn Gly Thr Tyr Asp His Tyr Ile Tyr Arg Asp Glu Ala Leu Asn
        500                 505                 510

Asn Arg Phe Gln Ile Lys Gly Val Glu Leu Lys Ser Gly Tyr Lys Asp
    515                 520                 525

Trp Ile Leu Trp Ile Ser Phe Ala Ile Ser Cys Phe Leu Ile Cys Val
530                 535                 540

Val Leu Leu Gly Phe Ile Met Trp Ala Cys Gln Lys Gly Asn Ile Arg
545                 550                 555                 560

Cys Asn Ile Cys Ile
            565
```

<210> SEQ ID NO 13
<211> LENGTH: 1565
<212> TYPE: DNA
<213> ORGANISM: Influenza A virus

<400> SEQUENCE: 13

| | | | | | |
|---|---|---|---|---|---|
| agcaaaagca | gggtagataa | tcactcactg | agtgacatca | aagtcatggc | gtctcaaggc | 60 |
| accaaacgat | cctatgaaca | gatggaaact | gatggggaac | gccagaatgc | aactgaaatc | 120 |
| agagcatctg | tcggaaggat | ggtgggagga | atcggccggt | tttatgttca | gatgtgtact | 180 |
| gagcttaaac | taaacgacca | tgaagggcgg | ctgattcaga | acagcataac | aatagaaagg | 240 |
| atggtacttt | cggcattcga | cgaaagaaga | aacaagtatc | tcgaggagca | tcccagtgct | 300 |
| gggaagacc | ctaagaaaac | gggaggcccg | atatacagaa | ggaaagatgg | aaatggatg | 360 |
| agggaactca | tcctccatga | taagaagaa | atcatgagaa | tctggcgtca | ggccaacaat | 420 |
| ggtgaagacg | ctactgctgg | tcttactcat | atgatgatct | ggcactccaa | tctcaatgac | 480 |
| accacatacc | aaagaacaag | ggctcttgtt | cggactggga | tggatccag | aatgtgctct | 540 |
| ctgatgcaag | gctcaaccct | cccacggaga | tctggagccg | ctggtgctgc | agtaaaaggt | 600 |
| gttgaacaa | tggtaatgga | actcatcaga | atgatcaaac | gcggaataaa | tgatcggaat | 660 |
| ttctggagag | gtgaaaatgg | tcgaagaacc | agaattgctt | atgaaagaat | gtgcaatatc | 720 |
| ctcaaggga | aatttcagac | agcagcacaa | cgggctatga | tggaccaggt | gagggaaggc | 780 |
| cgcaatcctg | gaaacgctga | gattgaggat | ctcatttct | tggcacgatc | agcacttatt | 840 |
| ttgagaggat | cagtagccca | taatcatgc | ctacctgcct | gtgtttatgg | ccttgcagta | 900 |
| accagtgggt | atgactttga | gaggaagga | tactctctgg | ttggaattga | tcctttcaaa | 960 |
| ctactccaga | cagtcaaat | tttcagtcta | atcagaccaa | agaaaaccc | agcacacaag | 1020 |
| agccagttgg | tgtggatggc | atgccattct | gcagcatttg | aggacctgag | agtttaaat | 1080 |
| ttcattagag | gaaccaaagt | aatcccaaga | ggacagttaa | caaccagagg | agttcaaata | 1140 |
| gcttcaaatg | aaaacatgga | gacaatagat | tctagcacac | ttgaactgag | aagcaaatat | 1200 |
| tgggcaataa | ggaccagaag | cggaggaaac | accagtcaac | agagagcatc | tgcaggacag | 1260 |
| ataagtgtgc | aacctacttt | ctcagtacag | agaaatcttc | cctttgagag | agcaaccatt | 1320 |
| atggctgcat | tcactggtaa | cactgaaggg | aggacttccg | acatgagaac | ggaaatcata | 1380 |
| aggatgatgg | aaaatgccaa | atcagaagat | gtgtctttcc | aggggcgggg | agtcttcgag | 1440 |
| ctctcggacg | aaaaggcaac | gaacccgatc | gtgccttcct | ttgacatgag | caatgaaggg | 1500 |
| tcttatttct | tcggagacaa | tgctgaggag | tttgacaatt | aaagaaaaat | acccttgttt | 1560 |
| ctact | | | | | | 1565 |

<210> SEQ ID NO 14
<211> LENGTH: 498
<212> TYPE: PRT
<213> ORGANISM: Influenza A virus

<400> SEQUENCE: 14

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Val Gln Met Cys Thr Glu Leu Lys
        35                  40                  45

```
Leu Asn Asp His Glu Gly Arg Leu Ile Gln Asn Ser Ile Thr Ile Glu
 50                  55                  60

Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                 85                  90                  95

Tyr Arg Arg Lys Asp Gly Lys Trp Met Arg Glu Leu Ile Leu His Asp
                100                 105                 110

Lys Glu Glu Ile Met Arg Ile Trp Arg Gln Ala Asn Asn Gly Glu Asp
                115                 120                 125

Ala Thr Ala Gly Leu Thr His Met Met Ile Trp His Ser Asn Leu Asn
130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Ile Arg Met Ile Lys Arg Gly Ile Asn Asp Arg Asn Phe Trp Arg
                195                 200                 205

Gly Glu Asn Gly Arg Arg Thr Arg Ile Ala Tyr Glu Arg Met Cys Asn
                210                 215                 220

Ile Leu Lys Gly Lys Phe Gln Thr Ala Ala Gln Arg Ala Met Met Asp
225                 230                 235                 240

Gln Val Arg Glu Gly Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Leu Ala Val Thr Ser Gly
                275                 280                 285

Tyr Asp Phe Glu Lys Glu Gly Tyr Ser Leu Val Gly Ile Asp Pro Phe
                290                 295                 300

Lys Leu Leu Gln Asn Ser Gln Ile Phe Ser Leu Ile Arg Pro Lys Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Asn Phe Ile Arg Gly Thr Lys Val
                340                 345                 350

Ile Pro Arg Gly Gln Leu Thr Thr Arg Gly Val Gln Ile Ala Ser Asn
                355                 360                 365

Glu Asn Met Glu Thr Ile Asp Ser Ser Thr Leu Glu Leu Arg Ser Lys
                370                 375                 380

Tyr Trp Ala Ile Arg Thr Arg Ser Gly Gly Asn Thr Ser Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
                420                 425                 430

Thr Glu Gly Arg Thr Ser Asp Met Arg Thr Glu Ile Ile Arg Met Met
                435                 440                 445

Glu Asn Ala Lys Ser Glu Asp Val Ser Phe Gln Gly Arg Gly Val Phe
450                 455                 460

Glu Leu Ser Asp Glu Lys Ala Thr Asn Pro Ile Val Pro Ser Phe Asp
```

```
                465                 470                 475                 480
Met Ser Asn Glu Gly Ser Tyr Phe Phe Gly Asp Asn Ala Glu Glu Phe
                    485                 490                 495

Asp Asn

<210> SEQ ID NO 15
<211> LENGTH: 1460
<212> TYPE: DNA
<213> ORGANISM: Influenza A virus

<400> SEQUENCE: 15
agcaaaagca ggagtttaaa atgaatccaa atcaaaagat aatagcaatt ggatttgcat      60
cattggggat attaatcatt aatgtcattc tccatgtagt cagcattata gtaacagtac     120
tggtcctcaa taacaataga acagatctga actgcaaagg gacgatcata agagagtgca    180
atgaaacagt aagagtagaa aaaattactc aatggtataa taccagtaca attaagtaca    240
tagagagacc ttcaaatgaa tactacatga acaacactga accactttgt gaggcccaag    300
gctttgcacc attttccaaa gataatggaa tacgaattgg gtcgagaggc catgtttttg    360
tgataagaga accttttgta tcatgttcgc cctcagaatg tagaacctttt tcctcacac    420
agggctcatt actcaatgac aaacattcta acggcacagt aaaggaccga agtccgtata    480
ggactttgat gagtgtcaga ataggggcaat cacctaatgt atatcaagct aggttttgaat   540
cggtagcatg gtcagcaaca gcatgccatg atggaaaaaa atggatgaca gttggagtca    600
cagggcccga caatcaagca attgcagtag tgaactatgg aggtgttccg gttgatatta    660
ttaattcatg ggcagggat attttaagaa cccaagaatc atcatgcacc tgcattaaag    720
gagactgtta ttgggtaatg actgatggac cggcaaatag gcaagctaaa ataggatat   780
tcaaagcaaa agatggaaga gtaattggac agactgatat aagtttcaat ggggggacaca    840
tagaggagtg ttcttgttac cccaatgaag ggaaggtgga atgcatatgc agggacaatt    900
ggactggaac aaatagacca attctggtaa tatcttctga tctatcgtac acagttggat    960
atttgtgtgc tggcattccc actgacactc tagggggaga ggatagtcaa ttcacaggct    1020
catgtacaag tccctttgga aataaaggat acggtgtaaa aggtttcggg tttcgacaag    1080
gaactgacgt atgggccgga aggacaatta gtaggacttc aagatcagga ttcgaaataa    1140
taaaatcag gaatggttgg acacagaaca gtaaagacca aatcaggagg caagtgatta   1200
tcgatgaccc aaattggtca ggatatagcg gttctttcac attgccggtt gaactaacaa    1260
aaaagggatg tttggtcccc tgtttctggg ttgaaatgat tagaggtaaa cctgaagaaa    1320
caacaatatg gacctctagc agctccattg tgatgtgtgg agtagatcat aaaaattgcca    1380
gttggtcatg gcacgatgga gctattcttc cctttgacat cgataagatg taatttacga    1440
aaaaactcct tgtttctact                                                1460

<210> SEQ ID NO 16
<211> LENGTH: 470
<212> TYPE: PRT
<213> ORGANISM: Influenza A virus

<400> SEQUENCE: 16

Met Asn Pro Asn Gln Lys Ile Ile Ala Ile Gly Phe Ala Ser Leu Gly
1               5                   10                  15

Ile Leu Ile Ile Asn Val Ile Leu His Val Val Ser Ile Ile Val Thr
            20                  25                  30
```

-continued

```
Val Leu Val Leu Asn Asn Arg Thr Asp Leu Asn Cys Lys Gly Thr
            35                  40                  45

Ile Ile Arg Glu Cys Asn Glu Thr Val Arg Val Glu Lys Ile Thr Gln
50                  55                  60

Trp Tyr Asn Thr Ser Thr Ile Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Ser Glu Cys Arg
            115                 120                 125

Thr Phe Phe Leu Thr Gln Gly Ser Leu Leu Asn Asp Lys His Ser Asn
130                 135                 140

Gly Thr Val Lys Asp Arg Ser Pro Tyr Arg Thr Leu Met Ser Val Arg
145                 150                 155                 160

Ile Gly Gln Ser Pro Asn Val Tyr Gln Ala Arg Phe Glu Ser Val Ala
                165                 170                 175

Trp Ser Ala Thr Ala Cys His Asp Gly Lys Lys Trp Met Thr Val Gly
            180                 185                 190

Val Thr Gly Pro Asp Asn Gln Ala Ile Ala Val Val Asn Tyr Gly Gly
            195                 200                 205

Val Pro Val Asp Ile Ile Asn Ser Trp Ala Gly Asp Ile Leu Arg Thr
210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Lys Tyr Arg Ile Phe Lys Ala
                245                 250                 255

Lys Asp Gly Arg Val Ile Gly Gln Thr Asp Ile Ser Phe Asn Gly Gly
            260                 265                 270

His Ile Glu Glu Cys Ser Cys Tyr Pro Asn Glu Gly Lys Val Glu Cys
            275                 280                 285

Ile Cys Arg Asp Asn Trp Thr Gly Thr Asn Arg Pro Ile Leu Val Ile
290                 295                 300

Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
                325                 330                 335

Ser Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
            355                 360                 365

Ser Gly Phe Glu Ile Ile Lys Ile Arg Asn Gly Trp Thr Gln Asn Ser
370                 375                 380

Lys Asp Gln Ile Arg Arg Gln Val Ile Ile Asp Pro Asn Asn Trp Ser
385                 390                 395                 400

Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ile Val Met Cys Gly Val
            435                 440                 445

Asp His Lys Ile Ala Ser Trp Ser Trp His Asp Gly Ala Ile Leu Pro
```

```
                450          455           460
Phe Asp Ile Asp Lys Met
465             470

<210> SEQ ID NO 17
<211> LENGTH: 1027
<212> TYPE: DNA
<213> ORGANISM: Influenza A virus

<400> SEQUENCE: 17
agcaaaagca ggtagatatt taaagatgag tcttctaacc gaggtcgaaa cgtacgttct      60
ctctatcgta ccatcaggcc ccctcaaagc cgagatcgcg cagagacttg aagatgtctt    120
tgcagggaag aacaccgatc ttgaggcact catggaatgg ctaaagacaa gaccaatcct    180
gtcacctctg actaaaggga ttttaggatt tgtattcacg ctcaccgtgc ccagtgagcg    240
aggactgcag cgtagacgct ttgtccaaaa tgcccttagt ggaacggag atccaaacaa     300
catggacaga gcagtaaaac tgtacaggaa gcttaaaaga gaataacat tccatggggc     360
aaaagaggtg gcactcagct attccactgg tgcactagcc agctgcatgg gactcatata    420
caacagaatg gaactgttta caaccgaagt ggcatttggc ctggtatgcg ccacatgtga    480
acagattgct gattcccagc atcgatctca caggcagatg gtgacaacaa ccaacccatt    540
aatcagacat gaaaacagaa tggtattagc cagtaccacg gctaaagcca tggaacagat    600
ggcaggatcg agtgagcagg cagcagaggc catggaggtt gctagtaggg ctaggcagat    660
ggtacaggca atgagaacca ttgggaccca ccctagctcc agtgccggtt tgaaagatga    720
tctcattgaa aatttacagg cctaccagaa acggatggga gtgcaaatgc agcgattcaa    780
gtgatcctct cgttattgca gcaagtatca ttgggatctt gcacttgata ttgtggattc    840
ttgatcgtct tttcttcaaa ttcatttatc gtcgccttaa atacggggttg aaaagagggc    900
cttctacgga aggagtacct gagtctatga gggaagaata tcggcaggaa cagcagaatg    960
ctgtggatgt tgacgatggt catttgtca acatagagct ggagtaaaaa actaccttgt    1020
ttctact                                                              1027

<210> SEQ ID NO 18
<211> LENGTH: 252
<212> TYPE: PRT
<213> ORGANISM: Influenza A virus

<400> SEQUENCE: 18

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
```

```
            115                 120                 125
Gly Leu Ile Tyr Asn Arg Met Gly Thr Val Thr Glu Val Ala Phe
    130                 135                 140
Gly Leu Val Cys Ala Thr Cys Glu Gln Ile Ala Asp Ser Gln His Arg
145                 150                 155                 160
Ser His Arg Gln Met Val Thr Thr Asn Pro Leu Ile Arg His Glu
                165                 170                 175
Asn Arg Met Val Leu Ala Ser Thr Ala Lys Ala Met Glu Gln Met
            180                 185                 190
Ala Gly Ser Ser Glu Gln Ala Ala Glu Ala Met Glu Val Ala Ser Arg
                195                 200                 205
Ala Arg Gln Met Val Gln Ala Met Arg Thr Ile Gly Thr His Pro Ser
    210                 215                 220
Ser Ser Ala Gly Leu Lys Asp Asp Leu Ile Glu Asn Leu Gln Ala Tyr
225                 230                 235                 240
Gln Lys Arg Met Gly Val Gln Met Gln Arg Phe Lys
                245                 250

<210> SEQ ID NO 19
<211> LENGTH: 97
<212> TYPE: PRT
<213> ORGANISM: Influenza A virus

<400> SEQUENCE: 19

Met Ser Leu Leu Thr Glu Val Glu Thr Pro Thr Arg Asn Gly Trp Glu
1               5                   10                  15
Cys Lys Cys Ser Asp Ser Ser Asp Pro Leu Val Ile Ala Ala Ser Ile
                20                  25                  30
Ile Gly Ile Leu His Leu Ile Leu Trp Ile Leu Asp Arg Leu Phe Phe
            35                  40                  45
Lys Phe Ile Tyr Arg Arg Leu Lys Tyr Gly Leu Lys Arg Gly Pro Ser
    50                  55                  60
Thr Glu Gly Val Pro Glu Ser Met Arg Glu Glu Tyr Arg Gln Glu Gln
65                  70                  75                  80
Gln Asn Ala Val Asp Val Asp Asp Gly His Phe Val Asn Ile Glu Leu
                85                  90                  95
Glu

<210> SEQ ID NO 20
<211> LENGTH: 890
<212> TYPE: DNA
<213> ORGANISM: Influenza A virus

<400> SEQUENCE: 20
agcaaaagca gggtgacaaa acataatgg attccaacac tgtgtcaagc tttcaggtag     60
actgttttct ttggcatgtc cgcaaacgat tcgcagacca agaactgggt gatgccccat    120
tccttgaccg gcttcgccga gaccagaagt ccctaagggg aagaggtagc actcttggtc    180
tggacatcga aacagccact catgcaggaa agcagatagt ggagcagatt ctggaaaagg    240
aatcagatga ggcacttaaa atgaccattg cctctgttcc tacttcacgc tacttaactg    300
acatgactct tgatgagatg tcaagagact ggttcatgct catgcccaag caaaaagtaa    360
caggctccct atgtataaga atggaccagg caatcatgga taagaacatc atacttaaag    420
caaactttag tgtgattttc gaaaggctgg aaacactaat actcttaga gccttcaccg    480
aagaaggagc agtcgttggc gaaatttcac cattaccttc tcttccagga catactaatg    540
```

-continued

```
aggatgtcaa aaatgcaatt ggggtcctca tcggaggact taaatggaat gataatacgg    600
ttagaatctc tgaaactcta cagagattcg cttggagaag cagtcatgag aatgggagac    660
cttcattccc ttcaaagcag aaatgaaaaa tggagagaac aattaagcca gaaatttgaa    720
gaaataagat ggttgattga agaagtgcga catagattga aaaatacaga aaatagtttt    780
gaacaaataa catttatgca agccttacaa ctattgcttg aagtagaaca agagataaga    840
actttctcgt ttcagcttat ttaatgataa aaaacaccct tgtttctact              890
```

<210> SEQ ID NO 21
<211> LENGTH: 219
<212> TYPE: PRT
<213> ORGANISM: Influenza A virus

<400> SEQUENCE: 21

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr His Ala Gly Lys Gln Ile
    50                  55                  60

Val Glu Gln Ile Leu Glu Lys Glu Ser Asp Glu Ala Leu Lys Met Thr
65                  70                  75                  80

Ile Ala Ser Val Pro Thr Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
        195                 200                 205

Asn Gly Arg Pro Ser Phe Pro Ser Lys Gln Lys
    210                 215

<210> SEQ ID NO 22
<211> LENGTH: 121
<212> TYPE: PRT
<213> ORGANISM: Influenza A virus

<400> SEQUENCE: 22

Met Asp Ser Asn Thr Val Ser Ser Phe Gln Asp Ile Leu Met Arg Met
1               5                   10                  15

Ser Lys Met Gln Leu Gly Ser Ser Ser Glu Asp Leu Asn Gly Met Ile
            20                  25                  30

Ile Arg Leu Glu Ser Leu Lys Leu Tyr Arg Asp Ser Leu Gly Glu Ala
        35                  40                  45

Val Met Arg Met Gly Asp Leu His Ser Leu Gln Ser Arg Asn Glu Lys
 50                  55                  60

Trp Arg Glu Gln Leu Ser Gln Lys Phe Glu Glu Ile Arg Trp Leu Ile
 65                  70                  75                  80

Glu Glu Val Arg His Arg Leu Lys Asn Thr Glu Asn Ser Phe Glu Gln
                 85                  90                  95

Ile Thr Phe Met Gln Ala Leu Gln Leu Leu Leu Glu Val Glu Gln Glu
                100                 105                 110

Ile Arg Thr Phe Ser Phe Gln Leu Ile
                115                 120

<210> SEQ ID NO 23
<211> LENGTH: 1768
<212> TYPE: DNA
<213> ORGANISM: Influenza A virus

<400> SEQUENCE: 23
agcaaaagca gggatatttt ctgtcaatca tgaagacaac cattattttt attttatac        60 tactgaccca ttgggcctac agtcaaaacc caatcagtaa caacaacaca gccacattgt      120
gtctgggaca ccatgcagta gcaaatggaa cattagtaaa acaataagt gatgatcaaa       180 ttgaggtgac aaatgctaca gaattagttc agagcatttc aatggggaaa atatgcaaca      240
actcatatag aattctagat ggaagaaatt gcacattaat agatgcaatg ctaggagacc      300
cccactgtga cgtctttcag tatgagaatt gggacctctt tatagaaaga gcagcgctt       360 tcagcaattg ctaccatat gacatccctg actatgcatc gctccgatca attgtagcat       420
cctcaggaac attggaattc acagcagagg gattcacatg gacaggtgtc actcaaaacg      480
gaagaagtgg agcctgcaaa aggggatcag ccgatagttt cttagccga ctgaattggc       540 taacaaatc tggaaactct tatcccacat gaatgtgac aatgcctaac aataaaatt        600 tcgacaagct atacatctgg gggattcatc acccgagttc aaatcaagag cagacaaaat      660
tgtatatcca gaatcagga cgagtaacag tctcaacaaa aagaagtcaa caaacaataa      720
tccctaacat cggatctaga ccgtgggtca gaggtcaatc aggcaggata agcatatact      780
ggaccattgt aaaacctgga gatatcctaa tgataaacag taatgcaac ttagttgcac      840 cgcggggata ttttaaattg aaaacaggga aaagctctgt aatgagatca gatgtaccca     900
tagacatttg tgtgtctgaa tgtattacac caaatggaag catctccaac gaaaagccat     960
tccaaaatgt aaacaaagtt acatatgaa aatgccccaa atatatcagg caaaacactt     1020
taaagttggc cactggaatg agaaatgtac cagaaaagca aatcagagga atctttggag    1080
caatagcggg attcatcgaa aacgctggg aaggaatggt tgatgggtgg tatgggttcc    1140
gataccaaaa ctctgaagga acaggacaag ctgcagatct aaagagcact caaacagcca    1200
tcgaccagat taatgaaaag ttaaacagg tgattgaaag aaccaatgaa aaattccatc    1260
agatagagaa ggaattctca gaagtagaag gaagaattca ggacttggag aaatatgtgg    1320
aagacaccaa aatagaccta tggtcctaca atgcagaatt gctggtggct ctagaaaatc    1380
aacatacaat tgacttaaca gatgcagaaa tgaataaatt attcgagaag actagacgcc    1440
agttaagaga aaacgcagaa gacatgggag gtggatgttt caagatttac cacaaatgtg    1500
ataatgcatg cattggatca ataagaaatg ggacatatga ccattacata tacagagatg    1560
aagcattaaa caaccgattt caaatcaaag gtgttgagtt gaaatcaggc tacaaagatt    1620
ggatactgtg gatttcattc gccatatcat gcttcttaat ttgcgttgtt ctattgggtt    1680

```
ttattatgtg ggcttgccaa aaaggcaaca tcagatgcaa catttgcatt tgagtaaact      1740
gatagttaaa aacacccttg tttctact                                        1768
```

<210> SEQ ID NO 24
<211> LENGTH: 567
<212> TYPE: PRT
<213> ORGANISM: Influenza A virus

<400> SEQUENCE: 24

Met Lys Thr Thr Ile Ile Phe Ile Phe Ile Leu Leu Thr His Trp Ala
1               5                   10                  15

Tyr Ser Gln Asn Pro Ile Ser Asn Asn Asn Thr Ala Thr Leu Cys Leu
            20                  25                  30

Gly His His Ala Val Ala Asn Gly Thr Leu Val Lys Thr Ile Ser Asp
        35                  40                  45

Asp Gln Ile Glu Val Thr Asn Ala Thr Glu Leu Val Gln Ser Ile Ser
    50                  55                  60

Met Gly Lys Ile Cys Asn Asn Ser Tyr Arg Ile Leu Asp Gly Arg Asn
65                  70                  75                  80

Cys Thr Leu Ile Asp Ala Met Leu Gly Asp Pro His Cys Asp Val Phe
                85                  90                  95

Gln Tyr Glu Asn Trp Asp Leu Phe Ile Glu Arg Ser Ser Ala Phe Ser
            100                 105                 110

Asn Cys Tyr Pro Tyr Asp Ile Pro Asp Tyr Ala Ser Leu Arg Ser Ile
        115                 120                 125

Val Ala Ser Ser Gly Thr Leu Glu Phe Thr Ala Glu Gly Phe Thr Trp
    130                 135                 140

Thr Gly Val Thr Gln Asn Gly Arg Ser Gly Ala Cys Lys Arg Gly Ser
145                 150                 155                 160

Ala Asp Ser Phe Phe Ser Arg Leu Asn Trp Leu Thr Lys Ser Gly Asn
                165                 170                 175

Ser Tyr Pro Thr Leu Asn Val Thr Met Pro Asn Asn Lys Asn Phe Asp
            180                 185                 190

Lys Leu Tyr Ile Trp Gly Ile His His Pro Ser Ser Asn Gln Glu Gln
        195                 200                 205

Thr Lys Leu Tyr Ile Gln Glu Ser Gly Arg Val Thr Val Ser Thr Lys
    210                 215                 220

Arg Ser Gln Gln Thr Ile Ile Pro Asn Ile Gly Ser Arg Pro Trp Val
225                 230                 235                 240

Arg Gly Gln Ser Gly Arg Ile Ser Ile Tyr Trp Thr Ile Val Lys Pro
                245                 250                 255

Gly Asp Ile Leu Met Ile Asn Ser Asn Gly Asn Leu Val Ala Pro Arg
            260                 265                 270

Gly Tyr Phe Lys Leu Lys Thr Gly Lys Ser Ser Val Met Arg Ser Asp
        275                 280                 285

Val Pro Ile Asp Ile Cys Val Ser Glu Cys Ile Thr Pro Asn Gly Ser
    290                 295                 300

Ile Ser Asn Glu Lys Pro Phe Gln Asn Val Asn Lys Val Thr Tyr Gly
305                 310                 315                 320

Lys Cys Pro Lys Tyr Ile Arg Gln Asn Thr Leu Lys Leu Ala Thr Gly
                325                 330                 335

Met Arg Asn Val Pro Glu Lys Gln Ile Arg Gly Ile Phe Gly Ala Ile
            340                 345                 350

```
Ala Gly Phe Ile Glu Asn Gly Trp Glu Gly Met Val Asp Gly Trp Tyr
            355                 360                 365
Gly Phe Arg Tyr Gln Asn Ser Glu Gly Thr Gly Gln Ala Ala Asp Leu
    370                 375                 380
Lys Ser Thr Gln Thr Ala Ile Asp Gln Ile Asn Glu Lys Leu Asn Arg
385                 390                 395                 400
Val Ile Glu Arg Thr Asn Glu Lys Phe His Gln Ile Glu Lys Glu Phe
                405                 410                 415
Ser Glu Val Glu Gly Arg Ile Gln Asp Leu Glu Lys Tyr Val Glu Asp
            420                 425                 430
Thr Lys Ile Asp Leu Trp Ser Tyr Asn Ala Glu Leu Leu Val Ala Leu
        435                 440                 445
Glu Asn Gln His Thr Ile Asp Leu Thr Asp Ala Glu Met Asn Lys Leu
450                 455                 460
Phe Glu Lys Thr Arg Arg Gln Leu Arg Glu Asn Ala Glu Asp Met Gly
465                 470                 475                 480
Gly Gly Cys Phe Lys Ile Tyr His Lys Cys Asp Asn Ala Cys Ile Gly
                485                 490                 495
Ser Ile Arg Asn Gly Thr Tyr Asp His Tyr Ile Tyr Arg Asp Glu Ala
            500                 505                 510
Leu Asn Asn Arg Phe Gln Ile Lys Gly Val Glu Leu Lys Ser Gly Tyr
        515                 520                 525
Lys Asp Trp Ile Leu Trp Ile Ser Phe Ala Ile Ser Cys Phe Leu Ile
        530                 535                 540
Cys Val Val Leu Leu Gly Phe Ile Met Trp Ala Cys Gln Lys Gly Asn
545                 550                 555                 560
Ile Arg Cys Asn Ile Cys Ile
                565
```

<210> SEQ ID NO 25
<211> LENGTH: 1460
<212> TYPE: DNA
<213> ORGANISM: Influenza A virus

<400> SEQUENCE: 25

| | | | | | |
|---|---|---|---|---|---|
| agcaaaagca | ggagtttaaa | atgaatccaa | atcaaaagat | aataacaatt | ggatctgcat | 60 |
| cattggggat | attaatcatt | aacgtcattc | tccatgtagt | cagcattata | gtaacagtac | 120 |
| tggtcctcaa | taacaatgaa | acaggtctga | actgcaaagg | gacgatcata | agagagtaca | 180 |
| atgaaacagt | aagagtagaa | aaaattactc | aatggcataa | taccagtgca | attaagtaca | 240 |
| tagagagacc | tccaaatgaa | tactacatga | acaacaccga | accactttgt | gaggcccaag | 300 |
| gctttgcacc | attttccaaa | gataatggaa | tacgaattgg | gtcgagaggc | catgttttg | 360 |
| tgataagaga | acctttgta | tcatgttcgc | cctcagaatg | tagaaccttt | ttcctcacac | 420 |
| agggctcatt | actcaatgac | aaacattcta | acggcacagt | aaaggatcga | agtccatata | 480 |
| ggactttgat | gagtgtcaaa | ataggggcaat | cacctaatgt | gtatcaagct | aggtttgaat | 540 |
| cggtggcatg | gtcagcaaca | gcatgccatg | atggaaaaaa | atggatgaca | attggagtca | 600 |
| cagggcccga | caatcaagca | attgcagtag | tgaactatgg | gggtgttccg | gttgatatta | 660 |
| ttaattcatg | ggcaggggac | atcttaagaa | cccaagaatc | atcatgcacc | tgcattaaag | 720 |
| gaaactgtta | ttgggtaatg | actgatggac | cggcaaatag | gcaagctaaa | tatagaatat | 780 |
| tcaaagcaaa | agatgaaga | gtaattggac | agactgatat | aagcttcaat | gggacacac | 840 |
| tagaggagtg | ttcttgttac | cccaatgaag | ggaaggtgga | atgcatatgc | agggacaatt | 900 |

```
ggactggaac aaatagacca attctggtaa tatcttctga tctatcgtac acagttggat   960
atttgtgtgc tggcattccc actgacactc ctaggggaga ggatagtcaa ttcacaggct  1020
catgtacaag tcctttggga aataaaggat acggtgtaaa aggtttcggg tttcgacaag  1080
gaactgacgt atgggccgga aggacaatta gtaggacttc gagatcagga ttcgaaataa  1140
taaaaatcag gaatggttgg acacagaaca gtaaagacca atcaggagg caagtgatta   1200 tcgatgaccc aaattggtca ggatatagcg gttctttcac attgccgatt gaactaacaa  1260
aaaagggatg tttggtcccc tgtttctggg ttgaaatgat tagaggtaaa cctgaagaaa  1320
caacaatatg gacctctagc agctccattg tgatgtgtgg agtagatcat aaaattgcca  1380
gttggtcatg gcacgatgga gctattcttc cctttgacat cgataagatg taatttacga  1440
aaaaactcct tgtttctact                                              1460
```

<210> SEQ ID NO 26
<211> LENGTH: 470
<212> TYPE: PRT
<213> ORGANISM: Influenza A virus

<400> SEQUENCE: 26

```
Met Asn Pro Asn Gln Lys Ile Ile Thr Ile Gly Ser Ala Ser Leu Gly
1               5                   10                  15

Ile Leu Ile Ile Asn Val Ile Leu His Val Val Ser Ile Ile Val Thr
            20                  25                  30

Val Leu Val Leu Asn Asn Asn Glu Thr Gly Leu Asn Cys Lys Gly Thr
        35                  40                  45

Ile Ile Arg Glu Tyr Asn Glu Thr Val Arg Val Glu Lys Ile Thr Gln
    50                  55                  60

Trp His Asn Thr Ser Ala Ile Lys Tyr Ile Glu Arg Pro Pro Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Ser Glu Cys Arg
        115                 120                 125

Thr Phe Phe Leu Thr Gln Gly Ser Leu Leu Asn Asp Lys His Ser Asn
    130                 135                 140

Gly Thr Val Lys Asp Arg Ser Pro Tyr Arg Thr Leu Met Ser Val Lys
145                 150                 155                 160

Ile Gly Gln Ser Pro Asn Val Tyr Gln Ala Arg Phe Glu Ser Val Ala
                165                 170                 175

Trp Ser Ala Thr Ala Cys His Asp Gly Lys Lys Trp Met Thr Ile Gly
            180                 185                 190

Val Thr Gly Pro Asp Asn Gln Ala Ile Ala Val Asn Tyr Gly Gly
        195                 200                 205

Val Pro Val Asp Ile Ile Asn Ser Trp Ala Gly Asp Ile Leu Arg Thr
    210                 215                 220

Gln Glu Ser Ser Cys Thr Cys Ile Lys Gly Asn Cys Tyr Trp Val Met
225                 230                 235                 240

Thr Asp Gly Pro Ala Asn Arg Gln Ala Lys Tyr Arg Ile Phe Lys Ala
                245                 250                 255

Lys Asp Gly Arg Val Ile Gly Gln Thr Asp Ile Ser Phe Asn Gly Gly
            260                 265                 270
```

His Ile Glu Glu Cys Ser Cys Tyr Pro Asn Glu Gly Lys Val Glu Cys
        275                 280                 285

Ile Cys Arg Asp Asn Trp Thr Gly Thr Asn Arg Pro Ile Leu Val Ile
290                 295                 300

Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
                325                 330                 335

Ser Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
        355                 360                 365

Ser Gly Phe Glu Ile Ile Lys Ile Arg Asn Gly Trp Thr Gln Asn Ser
370                 375                 380

Lys Asp Gln Ile Arg Arg Gln Val Ile Ile Asp Asp Pro Asn Trp Ser
385                 390                 395                 400

Gly Tyr Ser Gly Ser Phe Thr Leu Pro Ile Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ile Val Met Cys Gly Val
        435                 440                 445

Asp His Lys Ile Ala Ser Trp Ser Trp His Asp Gly Ala Ile Leu Pro
450                 455                 460

Phe Asp Ile Asp Lys Met
465                 470

<210> SEQ ID NO 27
<211> LENGTH: 1762
<212> TYPE: DNA
<213> ORGANISM: Influenza A virus

<400> SEQUENCE: 27
agcgaaagca gggatatttt ctgtcaatca tgacgataac cattattttg atactactga      60
cccattgggc ttacagtcaa acccaatca atgacaacaa cacagccaca ttgtgtctag     120
gacaccatgc agtagcaaat ggaacattgg taaaaacaat aagtgatgat caaattgagg     180
tgacaaatgc tacagaatta gttcagagca ttccaatggg gaaaatatgc aacaattcgt     240
atagaattct agatggaaag gattgcacat taatagatgc aatgctagga dccccccact     300
gtgacgcctt tcagtatgag aattgggacc tcttttataga agaagcagc gccttcagca     360 attgctaccc atatgacatc cctaactatg catcgctccg atccattgta gcatcctcag     420
gaacattgga attcacagca gagggattca catggacagg tgtcactcaa aacggaagaa     480
gcggatcctg caaaaggggga tcagccgata gtttctttag ccgactgaat tggctaacaa     540
aatccggaag ctcttacccc acattgaatg tgacaatgcc taacaataaa acttcgaca     600 agctatacat ctgggggatc catcacccga gctcaactca agagcagaca aaattgtata     660
tccaggaatc agggcgagta acagtctcaa caaaaagaag tcaacaaaca ataatcccta     720
acattgggtc tagaccatgg atcagaggtc aatcaggtag gataagcata tactggacca     780
ttgtaaaacc tggagatatt ctaatgataa acagtaatgg caacttagtt gcaccgcggg     840
gatactttaa attgaaaaca gggaaaagct ctgtaatgag atcagatgta cccatagaca     900
tttgtgtgtc tgaatgtatt acaccaaatg gaagcatctc caacgacaag ccattccaaa     960

```
atgtgaacaa agttacatat ggaaaatgtc ccaagtatat cagacaaaac actttaaagc    1020
tggccactgg gatgaggaat gtaccagaaa agcaaatcag aggaatcttc ggggcaatag    1080
cgggattcat cgaaaacggc tgggaaggaa tggttgatgg atggtatggg ttccgatacc    1140
aaaactctga aggaacaggg caagctgcag atctaaagag cactcaagca gccatcgacc    1200
agatcaatgg aaagttaaac agagtgattg aaagaacaaa tgagaaattc atcaaatag     1260 agaaggaatt ctcagaagta aaggaagaa ttcaggactt ggagaaatat gtagaagaca    1320
ccaaaataga cctatggtcc tacaatgcag aattgctggt ggctctagaa atcaacata     1380 caattgactt aacagatgca gaaatgaata aattgtttga gaaactaga cgcctgttaa    1440 gagaaaacgc agaagacatg ggaggtggat gtttcaagat ttaccacaaa tgtaataatg    1500
catgcattgg atcaataaga aatgggacat atgaccatta catatacaga gatgaagcat    1560
taaacaaccg atttcagatc aaaggtgtag agttgaaatc aggctacaaa gattggatac    1620
tctggatttc attcgccata tcatgcttct taatttgcgt tgttctattg ggttttatta    1680
tgtgggcttg ccaaaaaggc aacatcagat gcaacatttg catttgagta gattaatagt    1740
taaaaacacc cttgtttcta ct                                              1762
```

<210> SEQ ID NO 28
<211> LENGTH: 565
<212> TYPE: PRT
<213> ORGANISM: Influenza A virus

<400> SEQUENCE: 28

```
Met Thr Ile Thr Ile Ile Leu Ile Leu Leu Thr His Trp Ala Tyr Ser
1               5                   10                  15

Gln Asn Pro Ile Asn Asp Asn Asn Thr Ala Thr Leu Cys Leu Gly His
            20                  25                  30

His Ala Val Ala Asn Gly Thr Leu Val Lys Thr Ile Ser Asp Asp Gln
        35                  40                  45

Ile Glu Val Thr Asn Ala Thr Glu Leu Val Gln Ser Ile Pro Met Gly
    50                  55                  60

Lys Ile Cys Asn Asn Ser Tyr Arg Ile Leu Asp Gly Lys Asp Cys Thr
65                  70                  75                  80

Leu Ile Asp Ala Met Leu Gly Asp Pro His Cys Asp Ala Phe Gln Tyr
                85                  90                  95

Glu Asn Trp Asp Leu Phe Ile Glu Arg Ser Ser Ala Phe Ser Asn Cys
            100                 105                 110

Tyr Pro Tyr Asp Ile Pro Asn Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ser Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Thr Gln Glu Gln Thr Lys
        195                 200                 205

Leu Tyr Ile Gln Glu Ser Gly Arg Val Thr Val Ser Thr Lys Arg Ser
    210                 215                 220
```

```
Gln Gln Thr Ile Ile Pro Asn Ile Gly Ser Arg Pro Trp Ile Arg Gly
225                 230                 235                 240

Gln Ser Gly Arg Ile Ser Ile Tyr Trp Thr Ile Val Lys Pro Gly Asp
            245                 250                 255

Ile Leu Met Ile Asn Ser Asn Gly Asn Leu Val Ala Pro Arg Gly Tyr
        260                 265                 270

Phe Lys Leu Lys Thr Gly Lys Ser Ser Val Met Arg Ser Asp Val Pro
    275                 280                 285

Ile Asp Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
            325                 330                 335

Asn Val Pro Glu Lys Gln Ile Arg Gly Ile Phe Gly Ala Ile Ala Gly
        340                 345                 350

Phe Ile Glu Asn Gly Trp Glu Gly Met Val Asp Gly Trp Tyr Gly Phe
    355                 360                 365

Arg Tyr Gln Asn Ser Glu Gly Thr Gly Gln Ala Ala Asp Leu Lys Ser
370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
            405                 410                 415

Val Glu Gly Arg Ile Gln Asp Leu Glu Lys Tyr Val Glu Asp Thr Lys
        420                 425                 430

Ile Asp Leu Trp Ser Tyr Asn Ala Glu Leu Leu Val Ala Leu Glu Asn
    435                 440                 445

Gln His Thr Ile Asp Leu Thr Asp Ala Glu Met Asn Lys Leu Phe Glu
450                 455                 460

Arg Thr Arg Arg Leu Leu Arg Glu Asn Ala Glu Asp Met Gly Gly Gly
465                 470                 475                 480

Cys Phe Lys Ile Tyr His Lys Cys Asn Asn Ala Cys Ile Gly Ser Ile
            485                 490                 495

Arg Asn Gly Thr Tyr Asp His Tyr Ile Tyr Arg Asp Glu Ala Leu Asn
        500                 505                 510

Asn Arg Phe Gln Ile Lys Gly Val Glu Leu Lys Ser Gly Tyr Lys Asp
    515                 520                 525

Trp Ile Leu Trp Ile Ser Phe Ala Ile Ser Cys Phe Leu Ile Cys Val
530                 535                 540

Val Leu Leu Gly Phe Ile Met Trp Ala Cys Gln Lys Gly Asn Ile Arg
545                 550                 555                 560

Cys Asn Ile Cys Ile
            565

<210> SEQ ID NO 29
<211> LENGTH: 1460
<212> TYPE: DNA
<213> ORGANISM: Influenza A virus

<400> SEQUENCE: 29
agcaaaagca ggagtttaaa atgaatccaa atcaaaagat aatagcaatt ggatttacat     60
cattggggat attaatcatt agtgtcattc tccatgtagt cagcattata gtaacagtac    120
tggccctaaa taacaacaga acagatctga actgcaaaga gacgatcata agggagtaca    180
```

-continued

```
atgaaacagt aagagtagaa aaaattactc aatggtataa tatcagtaca attaagtaca    240
tagagaaacc ttcaaatgaa tactatatga acaacactga accactttgt gaggcccaag    300
gctttgcacc attttccaaa gataatggaa tacgaattgg atcgaggggc catgtttttg    360
tgataagaga accttttgta tcatgttcgc cttcagaatg tagaaccttt ttcctcacac    420
agggctcatt actcaatgac aaacattcta acggcacaat aaaggaccga agtccgtata    480
gaactctgat gagtgtcaaa atagggcaat cacctaatgt atatcaagct aggtttgaat    540
cagtggcatg gtcagcaaca gcatgccatg atggaaaaaa atggatgacg gttggagtca    600
cagggcctga caaccaagca attgcagtag tgaactatgg gggtgttccg gttgatatta    660
ttaattcatg ggcaggggat attttaagaa cccaagaatc gtcatgcacc tgcatcaaag    720
gagattgtta ttgggtaatg actgatgggc cggcgaatag gcaagccaaa tataagatat    780
tcaaagcaaa aaatggaaaa gtaattggac aaactgatat aagtttcaat ggaggacaca    840
tagaggagtg ttcttgttac cccaatgaag ggaaggtgga atgcatatgc agggacaatt    900
ggactggaac aaatagacca attttggtaa tatcttctga tctatcatac acagttggat    960
atttgtgtgc tggcattccc actgacactc ctaggggaga ggatagtcaa ttcacgggct   1020
catgtacaaa ccctttggga aataaaggat acggtgtaaa aggtttcgga tttcgacaag   1080
gaactgacgt atgggccgga aggacaatta gtagaacttc aagatcagga ttcgaaataa   1140
taaaaatcag gaatggttgg acacagaaca gtaaagacca aataaggagg caagtgatta   1200
tcgatgatca aaattggtca ggatatagcg gttctttcac attgccggtt gaactaacaa   1260
aaaaagaatg tttggtgccc tgtttctggg ttgaaatgat tagaggtaaa cctgaagaaa   1320
aaacaatatg gacctctagc agctccattg tgatgtgtgg agtagatcat aaaattgcca   1380
gttggtcatg gcacgatgga gctattcttc cctttgacat cgataagatg taatttacga   1440
aaaaactcct tgtttctact                                                1460
```

<210> SEQ ID NO 30
<211> LENGTH: 470
<212> TYPE: PRT
<213> ORGANISM: Influenza A virus

<400> SEQUENCE: 30

```
Met Asn Pro Asn Gln Lys Ile Ile Ala Ile Gly Phe Thr Ser Leu Gly
1               5                   10                  15

Ile Leu Ile Ile Ser Val Ile Leu His Val Val Ser Ile Ile Val Thr
            20                  25                  30

Val Leu Ala Leu Asn Asn Asn Arg Thr Asp Leu Asn Cys Lys Glu Thr
        35                  40                  45

Ile Ile Arg Glu Tyr Asn Glu Thr Val Arg Val Glu Lys Ile Thr Gln
    50                  55                  60

Trp Tyr Asn Ile Ser Thr Ile Lys Tyr Ile Glu Lys Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Ser Glu Cys Arg
        115                 120                 125

Thr Phe Phe Leu Thr Gln Gly Ser Leu Leu Asn Asp Lys His Ser Asn
    130                 135                 140
```

-continued

```
Gly Thr Ile Lys Asp Arg Ser Pro Tyr Arg Thr Leu Met Ser Val Lys
145                 150                 155                 160

Ile Gly Gln Ser Pro Asn Val Tyr Gln Ala Arg Phe Glu Ser Val Ala
            165                 170                 175

Trp Ser Ala Thr Ala Cys His Asp Gly Lys Lys Trp Met Thr Val Gly
        180                 185                 190

Val Thr Gly Pro Asp Asn Gln Ala Ile Ala Val Val Asn Tyr Gly Gly
        195                 200                 205

Val Pro Val Asp Ile Ile Asn Ser Trp Ala Gly Asp Ile Leu Arg Thr
        210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Lys Tyr Lys Ile Phe Lys Ala
            245                 250                 255

Lys Asn Gly Lys Val Ile Gly Gln Thr Asp Ile Ser Phe Asn Gly Gly
            260                 265                 270

His Ile Glu Glu Cys Ser Cys Tyr Pro Asn Glu Gly Lys Val Glu Cys
        275                 280                 285

Ile Cys Arg Asp Asn Trp Thr Gly Thr Asn Arg Pro Ile Leu Val Ile
        290                 295                 300

Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
            325                 330                 335

Asn Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
            355                 360                 365

Ser Gly Phe Glu Ile Ile Lys Ile Arg Asn Gly Trp Thr Gln Asn Ser
370                 375                 380

Lys Asp Gln Ile Arg Arg Gln Val Ile Ile Asp Asp Gln Asn Trp Ser
385                 390                 395                 400

Gly Tyr Ser Gly Ser Phe Thr Leu Pro Val Glu Leu Thr Lys Lys Glu
            405                 410                 415

Cys Leu Val Pro Cys Phe Trp Val Glu Met Ile Arg Gly Lys Pro Glu
            420                 425                 430

Glu Lys Thr Ile Trp Thr Ser Ser Ser Ile Val Met Cys Gly Val
            435                 440                 445

Asp His Lys Ile Ala Ser Trp Ser Trp His Asp Gly Ala Ile Leu Pro
        450                 455                 460

Phe Asp Ile Asp Lys Met
465             470
```